US012649792B2

(12) United States Patent　　(10) Patent No.:　US 12,649,792 B2

Elias et al.　　(45) Date of Patent:　　Jun. 9, 2026

(54) BISPECIFIC ANTIBODIES AGAINST CHI3L1 AND PD1 WITH ENHANCED T CELL-MEDIATED CYTOTOXIC EFFECTS ON TUMOR CELLS

(71) Applicant: Brown University, Providence, RI (US)

(72) Inventors: Jack A. Elias, Providence, RI (US); Chun Geun Lee, Providence, CT (US); Suchitra Kamle, Providence, RI (US)

(73) Assignee: Brown University, Providence, RI (US)

( * ) Notice: Subject to any disclaimer, the term of this patent is extended or adjusted under 35 U.S.C. 154(b) by 1107 days.

(21) Appl. No.: 17/609,309

(22) PCT Filed: May 6, 2020

(86) PCT No.: PCT/US2020/031710

§ 371 (c)(1),
(2) Date: Nov. 5, 2021

(87) PCT Pub. No.: WO2020/227431

PCT Pub. Date: Nov. 12, 2020

(65) Prior Publication Data

US 2022/0213193 A1　　Jul. 7, 2022

Related U.S. Application Data

(60) Provisional application No. 62/898,324, filed on Sep. 10, 2019, provisional application No. 62/876,507, filed on Jul. 19, 2019, provisional application No. 62/843,931, filed on May 6, 2019.

(51) Int. Cl.

| | |
|---|---|
| *C07K 16/28* | (2006.01) |
| *A61K 39/00* | (2006.01) |
| *A61P 35/00* | (2006.01) |
| *C07K 16/40* | (2006.01) |

(52) U.S. Cl.

CPC .......... *C07K 16/2818* (2013.01); *A61P 35/00* (2018.01); *C07K 16/40* (2013.01); *A61K 2039/505* (2013.01); *C07K 2317/31* (2013.01); *C07K 2317/622* (2013.01); *C07K 2317/73* (2013.01); *C07K 2317/76* (2013.01); *C07K 2317/92* (2013.01)

(58) Field of Classification Search

CPC ................ A61P 35/00; C07K 2317/31; C07K 2317/622; C07K 2317/76

See application file for complete search history.

(56) References Cited

U.S. PATENT DOCUMENTS

| | | | |
|---|---|---|---|
| 4,135,884 A | 1/1979 | Shen | |
| 4,305,924 A | 12/1981 | Piasio et al. | |
| 4,444,880 A | 4/1984 | Tom | |
| 4,943,522 A | 7/1990 | Eisinger et al. | |
| 5,585,089 A | 12/1996 | Queen et al. | |
| 5,622,871 A | 4/1997 | May et al. | |
| 5,770,460 A | 6/1998 | Pawlak et al. | |
| 6,187,598 B1 | 2/2001 | May et al. | |
| 6,485,982 B1 | 11/2002 | Charlton | |
| 6,565,808 B2 | 5/2003 | Hudak et al. | |
| 6,808,710 B1 | 10/2004 | Wood et al. | |
| 6,809,687 B2 | 10/2004 | Yuanzhu | |
| 6,824,989 B1 | 11/2004 | Eisinger et al. | |
| 6,835,823 B2 | 12/2004 | Le et al. | |
| 7,427,605 B2 | 9/2008 | Davis et al. | |
| 8,172,901 B2 | 5/2012 | Altman et al. | |
| 8,329,660 B2 | 12/2012 | Kuchroo et al. | |
| 8,673,301 B2 | 3/2014 | Bonnichsen et al. | |
| 10,253,111 B2 * | 4/2019 | Elias ........................ A61P 35/04 |
| 10,752,700 B2 | 8/2020 | Elias et al. | |
| 10,766,968 B2 * | 9/2020 | Elias ..................... C07K 16/40 |
| 11,667,725 B2 | 6/2023 | Elias et al. | |
| 11,667,726 B2 | 6/2023 | Elias et al. | |
| 2002/0058037 A1 | 5/2002 | Noelle et al. | |
| 2004/0184954 A1 | 9/2004 | Guo et al. | |
| 2004/0197328 A1 | 10/2004 | Young et al. | |
| 2007/0190599 A1 | 8/2007 | Nakano et al. | |
| 2011/0009960 A1 | 1/2011 | Altman et al. | |
| 2011/0027270 A1 | 2/2011 | Garcia-Sastre et al. | |
| 2011/0167602 A1 | 7/2011 | Altman et al. | |
| 2012/0296352 A1 | 11/2012 | Altman et al. | |
| 2014/0127225 A1 | 5/2014 | Basi et al. | |

(Continued)

FOREIGN PATENT DOCUMENTS

| | | |
|---|---|---|
| CN | 103987405 A | 8/2014 |
| CN | 105092855 A | 11/2015 |

(Continued)

OTHER PUBLICATIONS

Islam and Khan, "Lung biopsy cells transcriptional landscape from COVID-19 patient stratified lung injury in SARS-COV-2 infection through impaired pulmonary surfactant metabolism" BioRxiv, May 8, 2020, https://doi.org/10.1101/2020.05.07.082297 (Year: 2020).*

Diao et al., "Reduction and Functional Exhaustion of T Cells in Patients with Coronavirus Disease 2019 (COVID-19)", MedRxiv, Feb. 20, 2020, https://doi.org/10.1101/2020.02.18.20024364 (Year: 2020).*

Libreros et al., "Induction of proinflammatory mediators by CHI3L1 is reduced by chitin treatment: decreased tumor metastasis in a breast cancer model", Int. J. Cancer, 2012, 131:377-386 (Year: 2012).*

Kim et al., "Regulation of chitinase-3-like-1 in T cell elicits Th1 and cytotoxic responses to inhibit lung metastasis", Nat Comm, 2018 , 9:503 (Year: 2018).*

(Continued)

*Primary Examiner* — Adam Weidner

(74) *Attorney, Agent, or Firm* — Banner & Witcoff, Ltd.

(57) ABSTRACT

Described herein are bispecific antibodies simultaneously targeting both CHI3L1 and the immune checkpoint molecule PD-1. These antibodies manifest enhanced synergistic cytotoxic effects compared to the effects of individual CHI3L1 and PD-1 antibodies, alone or in combination. Methods of treating a cancer by administering the bispecific antibodies described herein are also provided.

18 Claims, 8 Drawing Sheets

Specification includes a Sequence Listing.

(56) References Cited

U.S. PATENT DOCUMENTS

| | | | |
|---|---|---|---|
| 2015/0119555 A1 | 4/2015 | Jung et al. | |
| 2016/0145355 A1 | 5/2016 | Saha et al. | |
| 2016/0166520 A1 | 6/2016 | Elias et al. | |
| 2017/0037131 A1 | 2/2017 | Bernett et al. | |
| 2018/0092989 A1 | 4/2018 | Lyerly et al. | |
| 2018/0327501 A1 | 11/2018 | Wang et al. | |
| 2019/0002586 A1 | 1/2019 | Elias et al. | |
| 2019/0031785 A1* | 1/2019 | Schuetz | C07K 16/2878 |
| 2019/0062457 A1 | 2/2019 | Elias et al. | |
| 2019/0119405 A1 | 4/2019 | Elias et al. | |
| 2021/0369709 A1 | 12/2021 | Rukazenkov et al. | |
| 2021/0395377 A1 | 12/2021 | Elias et al. | |
| 2022/0213193 A1 | 7/2022 | Elias et al. | |
| 2022/0370608 A1 | 11/2022 | Penna et al. | |
| 2023/0046834 A1 | 2/2023 | Elias et al. | |
| 2023/0183323 A1 | 6/2023 | Elias et al. | |
| 2023/0406958 A1 | 12/2023 | Elias et al. | |
| 2024/0076407 A1 | 3/2024 | Elias et al. | |

FOREIGN PATENT DOCUMENTS

| | | | | |
|---|---|---|---|---|
| CN | 109575139 A | 4/2019 | | |
| JP | 2018525347 A | 9/2018 | | |
| WO | 9501995 A1 | 1/1995 | | |
| WO | 9623071 A2 | 8/1996 | | |
| WO | 9740068 A1 | 10/1997 | | |
| WO | 03063792 A2 | 8/2003 | | |
| WO | 2004106383 A1 | 12/2004 | | |
| WO | 2006089549 A1 | 8/2006 | | |
| WO | 2007027748 A2 | 3/2007 | | |
| WO | 2009092382 A1 | 7/2009 | | |
| WO | 2012051734 A1 | 4/2012 | | |
| WO | 2018129261 A1 | 7/2018 | | |
| WO | 2018188612 A1 | 10/2018 | | |
| WO | 2019009727 A1 | 1/2019 | | |
| WO | 2019036566 A1 | 2/2019 | | |
| WO | 2019040685 A1 | 2/2019 | | |
| WO | WO-2019042153 A1 * | 3/2019 | | A61K 39/395 |
| WO | WO-2019060675 A1 * | 3/2019 | | A61P 35/00 |
| WO | 2019062755 A1 | 4/2019 | | |
| WO | 2019070908 A1 | 4/2019 | | |
| WO | 2019090002 A1 | 5/2019 | | |
| WO | 2019157533 A1 | 8/2019 | | |
| WO | 2021102131 A1 | 5/2021 | | |

OTHER PUBLICATIONS

Koopmans et al., "A novel bispecific antibody for EGFR-directed blockade of the PD-1/PD-L1 immune checkpoint", Oncoimmunol, 2018, 7:8 (Year: 2018).*

Vivarella et al., "Immune-checkpoint inhibitors from cancer to COVID-19: A promising avenue for the treatment of patients with COVID-19", Int J Oncol, 2021, 58:145-157 (Year: 2021).*

Pezeshki & Rezaei, "Immune checkpoint inhibition in COVID-19: risks and benefits", Exp Opin Biol Ther, 2021, 21:9, 1173-1179 (Year: 2021).*

Kimura et al., "Identification of serum prognostic biomarkers of severe COVID-19 using a quantitative proteomic approach", Sci Rep , 2021, 11:20638 (Year: 2021).*

Freeman, G. J., et al., "Engagement of the PD-1 Immunoinhibitory Receptor by a Novel B7 Family Member Leads to Negative Regulation of Lymphocyte Activation", Journal of Experimental Medicine, vol. 192, No. 7, Oct. 2, 2000 1027-1034 (Year: 2000).*

Houston, D. R., et al., "Structure and Ligand-induced Conformational Change of the 39-kDa Glycoprotein from Human Articular Chondrocytes", 2003, J Biol Chem, 278:32, p. 30206-30212 (Year: 2003).*

Libreros, S., et al., "CHI3L1 plays a role in cancer through enhanced production of pro-inflammatory/pro-tumorigenic and angiogenic factors", Immunol Res (2013) 57:99-105 (Year: 2013).*

McDermott & Atkins, "PD-1 as a potential target in cancer therapy", Cancer Med, 2013; 2(5): 662-673 (Year: 2013).*

Schreiber et al., "3D-Epitope-Explorer (3DEX): Localization of Conformational Epitopes within Three-Dimensional Structures of Proteins", 2005, Journal of Computational Chemistry, 42-44:60596 (Year: 2005).*

Almagro and Fransson, "Humanization of antibodies", 2008, Fronteirs in Bioscience 13,1619-1633 (Year: 2008).*

Gershoni, J. M., et al., "Epitope Mapping The First Step in Developing Epitope-Based Vaccines", 2007, Biodrugs, 21(3): 145-156 (Year: 2007).*

Blythe, M. J. and Flower, D. R., "Benchmarking B cell epitope prediction: Underperformance of existing methods", 2005, Protein Science, 14:246-248 (Year: 2005).*

International Search Report and Written Opinion received in International Application No. PCT/US2020/031710, mailed on Sep. 9, 2020, 15 pages.

"International Search Report and Written Opinion received for Application No. PCT/US2023/081359, mailed on Jun. 13, 2024", 16 pages.

"Extended European Search Report and Search Opinion received for EP Patent Application No. 19882794.1, mailed Aug. 11, 2022", 8 pages.

"Extended European Search Report received for EP Patent Application No. 18736054.0, mailed on Nov. 13, 2020", Nov. 13, 2020, 14 pages.

"Extended European Search Report received for European Application No. EP20889751.2, mailed on Apr. 29, 2024", 10 pages.

"Extended European Search Report received in European Patent Application No. 18848101.4, mailed on Apr. 13, 2021", 10 pages.

"International Search Report and Written Opinion for PCT/US2019/060288 mailed Feb. 10, 2020", Feb. 10, 2020, 13 Pages.

"International Search Report and Written Opinion received for PCT Patent Application No. PCT/US2018/047633, mailed on Dec. 13, 2018", 13 pages.

"International Search Report and Written Opinion received for PCT Patent Application No. PCT/US2020/061267, mailed on Mar. 12, 2021", 12 pages.

"International Search Report and Written Opinion received for PCT Patent Application No. PCT/US2021/033085, mailed on Nov. 4, 2021", 14 pages.

"Invitation to Pay Additional Fees received for Application No. PCT/US2023/081359, mailed on Apr. 30, 2024", 3 pages.

"Partial Supplementary European Search Report received for EP Patent Application No. 18736054.0, mailed on Aug. 10, 2020", 15 pages.

"Partial Supplementary European Search Report received for European Patent Application No. 20889751.2, Mailed on Jan. 19, 2024", 11 pages.

Abaza , et al., "Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin", Journal of Protein Chemistry, vol. 11, No. 5, 1992, pp. 433-444.

Almagro , et al., "Humanization of antibodies", Frontiers in Bioscience, vol. 13, 2008, pp. 1619-1633.

Becerra-Flores , et al., "SARS-COV-2 Viral Spike G614 Mutation Exhibits Higher Case Fatality Rate", International Journal of Clinical Practice, vol. 74, 2020, pp. 1-4.

Brinkmann , et al., "The Making of Bispecific Antibodies", Monoclonal antibodies (MAbs), vol. 9, No. 2, Jan. 10, 2017, pp. 182-212.

Canet , et al., "Modeling Human Nonalcoholic Steatohepatitis-Associated Changes in Drug Transporter Expression Using Experimental Rodent Models", Drug Metabolism and Disposition vol. 42, No. 4,, Apr. 2014, pp. 586-595.

Carter , et al., "Engineering antibodies for imaging and therapy", Current Opinion in Biotechnology, 1997, pp. 449-454.

Chames , et al., "Therapeutic antibodies: successes, limitations and hopes for the future", British J. of Pharmacology, vol. 157, 2009, pp. 220-233.

Choi , et al., "High Serum YKL-40 is a Poor Prognostic Marker in Patients With Advanced Non-Small Cell Lung Cancer", Acta Oncologica, vol. 49, Issue 6, 2010, pp. 861-864.

(56)                 References Cited

OTHER PUBLICATIONS

Choi , et al., "Human Regulatory T Cells Kill Tumor Cells Through Granzyme-dependent Cytotoxicity Upon Retargeting With a Bispecific Antibody", Cancer Immunology Research, vol. 1, No. 3, 2013, pp. 163-167.

Chupp , et al., "A Chitinase-Like Protein in the Lung and Circulation of Patients with Severe Asthma", The New England Journal of Medicine, vol. 357, No. 20, 2007, pp. 2016-2027.

Colman, P.M. , "Effects of amino acid sequence changes on antibody-antigen interactions", Research in Immunology, vol. 145,, 1994, pp. 33-36.

Dixon , "Evaluation of the CASP2 docking section", Proteins, Suppl 1, 1997, pp. 198-204.

Farrell , et al., "Nonalcoholic Fatty Liver Disease: From Steatosis to Cirrhosis", Hepatology, vol. 43, Feb. 2006, pp. S99-S112.

Gura, T , "Systems for identifying new drugs are often faulty", Science, vol. 278, 1997, pp. 1041-1042.

Gussow, et al., "Humanization of Monoclonal Antibodies", Methods in Enzymology, vol. 203, 1991, pp. 99-121.

Junker , et al., "Expression of Ykl-40 by Peritumoral Macrophages in Human Small Cell Lung Cancer", Lung Cancer vol. 48, No. 2, 2005, pp. 223-231.

Kaiser, Jocelyn , "First Pass at Cancer Genome Reveals Complex Landscape", Science, vol. 313, 2006, p. 1370.

Kim , et al., "Suppression of metastasis through inhibition of chitinase 3-like 1 expression by miR-125a-3p-mediated up-regulation of USFI", Theranosti CS, vol. 8, No. 16, Jan. 1, 2018, pp. 4409-4428.

Kouklis , et al., "In vitro assembly properties of vimentin mutagenized at the-site tail motif", J Cell Science, vol. 106, No. 3, 1993, pp. 919-928.

Kumagai , et al., "Serum YKL-40 as a marker of liver fibrosis in patients with non-alcoholic fatty liver disease", Scientific Reports, vol. 6: 35282, 2016, 10 pages.

Kzhyshkowska, Julia , et al., "Role of chitinase-like proteins in cancer", Biological Chemistry, vol. 397, No. 3, Retrieved from the Internet: URL:http://dx.doi.org/10.1515/hsz-2015-0269>, Mar. 1, 2016, pp. 231-247.

Lazerow, et al., "Drug-Induced Liver Disease 2004", Curr. Opin. Gastroenterol., vol. 21, No. 3, May 2005, pp. 283-292.

Lee , et al., "Role of Breast Regression Protein 39 (BRP-39)/Chitinase 3-Like-1 in Th2 and IL-13-Induced Tissue Responses and Apoptosis", J. Exp. Med., vol. 206, No. 5, DOI: 10.1084/jem. 20081271, May 11, 2009, pp. 1149-1166.

Lensink , et al., "Docking and scoring protein complexes: CAPRI 3rd Edition", Proteins, vol. 69, 2007, pp. 704-718.

Li , et al., "SARS-CoV-2 Viremia is Associated with Distinct Proteomic Pathways and Predicts COVID-19 Outcomes", The Journal of clinical investigation, vol. 131, No. 13, e148635, 2021, pp. 1-12.

Lin , et al., "Chitinase-3-like protein 1 as a predictor for the progression or regression of liver fibrosis", Hepatoma Research, vol. 4, No. 8, Retrieved from the Internet: URL:https://oaepublishstorage. blob.core.windows.net/e99119d6-dd81-45ab-be20-ff7c28d369d2/2748.pdf, Aug. 18, 2018, 48 page.

Lorenz , et al., "Steroid and Lipid Conjugates of siRNAs to Enhance Cellular Uptake and Gene Silencing in Liver cells", Bioorganic & Medicinal Chemistry Letters, vol. 14, Issue 19, Oct. 4, 2004, pp. 4975-4977.

Lu , et al., "Fab-scFv Fusion Protein: An Efficient Approach to Production of Bispecific Antibody Fragments", Journal of Immunological Methods, vol. 267, No. 2, 2002, pp. 213-226.

Ma, et al., "CHI3L1 Enhances Melanoma Lung Metastasis via Regulation of T Cell Co-Stimulators and CTLA-4/B7 Axis", Frontiers in Immunology, vol. 13, Dec. 21, 2022, 16 pages.

Ma , et al., "RIG-Like Helicase Regulation of Chitinase 3-Like 1 Axis and Pulmonary Metastasis", Scientific Reports vol. 6, Article No. 26299, May 20, 2016, pp. 1-13.

Ma, et al., "Role of Chitinase 3-Like-1 and Semaphorin 7a in Pulmonary Melanoma Metastasis", Cancer Research, vol. 75, No. 3, Feb. 1, 2015, pp. 487-496.

Mariuzza , et al., "The Structural Basis of Antigen-Antibody Recognition", Annual review of Biophysics and Biophysical Chemistry, vol. 16, 1987, pp. 139-159.

Merchant , et al., "Monovalent antibody design and mechanism of action of onartuzumab, a MET antagonist with anti-tumor activity as a therapeutic agent", PNAS vol. 110, No. 32,, 2013, pp. E2987-E2996.

Palekar , et al., "Clinical Model for Distinguishing Nonalcoholic Steatohepatitis from Simple Steatosis in Patients with Nonalcoholic Fatty Liver Disease", Liver Int., vol. 26, No. 2, Mar. 2006, pp. 151-156.

"International Search Report and Written Opinion received for PCT Patent Application No. PCT/US2018/012494, mailed on May 2, 2018", 10 Pages.

Pitt , et al., "Resistance Mechanisms to Immune-Checkpoint Blockade in Cancer: Tumor-Intrinsic and -Extrinsic Factors", 2016, pp. 1255-1269.

Rudikoff , et al., "Single amino acid substitution altering antigen-binding specificity", PNAS, vol. 79, 1982, pp. 1979-1983.

Schreier , et al., "Allotypic differences in murine u genes", Nucleic Acids Research, vol. 14, No. 5, 1986, pp. 2381-2389.

Sohn , et al., "The Chitinase-like Proteins Breast RegressionProtein-39 and YKL-40 Regulate Hyperoxia-inducedAcute Lung Injury", American Journal of Respiratory and Critical Care Medicine, vol. 182, No. 7, Jun. 17, 2010, pp. 918-928.

Yanqi, YE , et al., "Synergistic Transcutaneous Immunotherapy Enhances Antitumor Immune Responses through Delivery of Checkpoint Inhibitors", ACS Nano, vol. 9, Retrieved from the Internet: URL:https://pubs.acs.org/doi/pdf/10.1021/acsnano.6b04989>, Sep. 6, 2016, pp. 8956-8963.

Steenbakkers , et al., "Localization of MHC Class II/Human Cartilage Glycoprotein-39 Complexes in Synovia of Rheumatoid Arthritis Patients Using Complex-Specific Monoclonal Antibodies", The Journal of Immunology, vol. 170, 2003, pp. 5719-5727.

Straub , et al., "Cassette mutagenesis of a potential substrate recognition region of cytochrome P450 2C2", Journal of Biological Chemistry, vol. 268, No. 29, 1993, pp. 21997-22003.

Sujith, Dassanayaka , et al., "Abstract 16699: Chitinase-3-like-1 Reduces Reparative Inflammatory Cells and Exacerbates Cardiac Dysfunction After Myocardial Infarction I Circulation", Circulation, Retrieved from the Internet: URL:https://www.ahajournals.org/doi/10.1161/circ.134.suppl_1.16699, [retrieved on Aug. 1, 2022], Mar. 29, 2018, pp. 1-6.

Tame, Jeremy R.H, "Scoring Functions: A View from the Bench", Journal of Computer—Aided Molecular Desugn, vol. 13, 1999, pp. 99-108.

Thom , et al., "Elevated Pretreatment Serum Concentration of YKL-40—An Independent Prognostic Biomarker for Poor Survival in Patients With Metastatic Nonsmall Cell Lung Cancer", Cancer, vol. 116, No. 17 DOI: 10.1002/cncr.25196, Sep. 1, 2010, pp. 4114-4121.

Tomar , et al., "Identification of SARS-CoV-2 E Channel Blockers from a Repurposed Drug Library", Pharmaceuticals, vol. 14, No. 604, Jun. 23, 2021, 10 pages.

Winkler , et al., "Changing The Antigen Binding Specificity by Single Point Mutations of an Anti-p24 {HIV-1} Antibody", The Journal of Immunology; vol. 165; Issue 8, 2000, pp. 4505-4514.

Xia, et al., "Inhibition of SARS-CoV-2 (previously 2019-nCoV) Infection by a Highly Potent Pan Coronavirus Fusion Inhibitor Targeting its Spike Protein that Harbors a High Capacity to Mediate Membrane Fusion", Cell Research, vol. 30, Mar. 30, 2020, pp. 343-355.

Yang, Zhou , et al., "Chitinase 3-Like 1 Suppresses Injury and Promotes Fibroproliferative Responses in Mammalian Lung Fibrosis", Science Translational Medicine, vol. 6, No. 240, Retrieved from the Internet: URL:https://www.ncbi.nlm.nih.gov/pmc/articles/PMC4340473/pdf/nihms-664146.pd, Jun. 11, 2014, 28 pages.

"Extended European Search Report received for EP Patent Application No. 20801507.3, mailed on Dec. 6, 2022", 10 pages.

(56) References Cited

OTHER PUBLICATIONS

Dahlén , et al., "Bispecific Antibodies in Cancer Immunotherapy", Therapeutic Advances in Vaccines and Immunotherapy, vol. 6, No. 1, 2018, pp. 3-17.

Faibish, M. , et al., "A YKL-40—Neutralizing Antibody Blocks Tumor Angiogenesis and Progression: A Potential Therapeutic Agent in Cancers", Molecular Cancer Therapeutics, vol. 10, No. 5, Feb. 25, 2011, pp. 742-751.

Hellmann , et al., "Nivolumab plus Ipilimumab in Advanced Non-Small-Cell Lung Cancer", The New England Journal of Medicine, Sep. 28, 2019, 4 pages.

Paz-Ares , et al., "Pembrolizumab plus Chemotherapy for Squamous Non-Small-Cell Lung Cancer", The New England Journal of Medicine, vol. 379, 2018, pp. 2040-2051.

Schoenfeld , et al., "Clinical and Molecular Correlates of PD-L1 Expression in Patients with Lung Adenocarcinomas", Annals of Oncology, vol. 31, No. 5, 2020, pp. 599-608.

* cited by examiner (B)

CHI3L1

ScFV-PD1

(A)

ScFV-PD1

CHI3L1

(C)

(B)

(A)

(B)

(A)

BISPECIFIC ANTIBODIES AGAINST CHI3L1 AND PD1 WITH ENHANCED T CELL-MEDIATED CYTOTOXIC EFFECTS ON TUMOR CELLS

CROSS REFERENCE TO RELATED APPLICATIONS

This application is a national phase filing under 35 U.S.C. § 371 of International Application No. PCT/US2020/031710 filed May 6, 2020, which claims priority from U.S. Provisional Patent Application No. 62/843,931 filed May 6, 2019, U.S. Provisional Patent Application No. 62/876,507 filed Jul. 19, 2019, and U.S. Provisional Patent Application No. 62/898,324 filed Sep. 10, 2019, the entire contents of which are hereby incorporated by reference herein.

STATEMENT REGARDING FEDERALLY SPONSORED RESEARCH OR DEVELOPMENT

This invention was developed with the following funding: NIH CADET Grant UH2 HL123876 awarded by the National Institutes of Health. The government has certain rights in this invention.

FIELD OF THE INVENTION

The embodiments of the present invention relate to bispecific antibodies simultaneously targeting both CHI3L1 and the immune checkpoint molecule PD-1. These bispecific antibodies manifest enhanced synergistic cytotoxic effects that are greater than the effects of the individual CHI3L1 and PD-1 antibodies, alone or in combination.

SEQUENCE LISTING

The instant application contains a Sequence Listing which has been submitted electronically in ASCII format and is hereby incorporated by reference in its entirety. Said ASCII copy, created on May 29 2020, is named 405505-591001WO SL.txt and is 31,227 bytes in size.

BACKGROUND OF THE INVENTION

Currently, immunotherapy against individual immune checkpoint inhibitor (ICPI) molecules is being effectively applied to patients with various malignancies including lung cancer and glioblastoma. Examples include antibodies against moieties like programed death receptor 1 (PD-1). However, only subsets of patients respond to these therapeutics. In addition, the responses that are seen are often not durable. As a result, intensive efforts are being directed worldwide to develop ways to enhance the effectiveness of ICPI immunotherapy using antibodies against immune checkpoint molecules including PD-1.

Accordingly, there is a need for more effective immunotherapy against individual immune checkpoint inhibitor molecules such as PD-1.

BRIEF SUMMARY OF THE INVENTION

Previous studies demonstrated that chitinase 3-like-1 (CHI3L1) plays a critical role in the pathogenesis of various cancers. Moreover, we have previously demonstrated that the combination of an anti-CHI3L1 antibody with an anti-PD-1 antibody provides synergistic effects in the treatment of cancer. Based on these findings, we hypothesized that the simultaneous targeting of CHI3L1 and PD-1 might have additional synergistic and or additive antitumor effects. To address these possibilities, bispecific antibodies were developed that simultaneously react with CHI3L1 and PD-1.

The embodiments of the present invention provide humanized bispecific antibodies simultaneously detect and neutralize both CHI3L1 and the immune checkpoint inhibitor PD-1. The bispecific antibodies comprise an antigen-binding portion of an anti-human PD-1 antibody and an antigen-binding portion of an anti-human CHI3L1 antibody.

In some embodiments, the bispecific antibodies comprise an anti-human PD-1 single chain variable fragment (ScFv-PD1) attached to the backbone of an anti-human CHI3L1 antibody. The ScFv-PD1 can be attached to either the CHI3L1 antibody heavy chain (CHI3L1-HC-PD1) or to the CHI3L1 antibody light chain (CHI3L1-LC-PD1).

In alternative embodiments, the bispecific antibodies comprise an anti-human CHI3L1 single chain variable fragment (ScFv-CHI3L1) attached to the backbone of an anti-human PD-1 antibody. The ScFv-CHI3L1 can be attached to either the PD-1 antibody heavy chain (PD-1-HC-CHI3L1) or to the PD-1 antibody light chain (PD-1-LC-CHI3L1).

In one embodiment, the antigen-binding portion of the anti-human CHI3L1 antibody comprises the complementarity determining regions (CDRs) of: (a) a light chain CDR1 having the amino acid sequence of SEQ ID NO: 4; (b) a light chain CDR2 having the amino acid sequence of SEQ ID NO: 5; (c) a light chain CDR3 having the amino acid sequence of SEQ ID NO: 6; (d) a heavy chain CDR1 having the amino acid sequence of SEQ ID NO: 1; (e) a heavy chain CDR2 having the amino acid sequence of SEQ ID NO: 2; and (f) a heavy chain CDR3 having the amino acid sequence of SEQ ID NO: 3. In one embodiment, the antigen-binding portion of the anti-human CHI3L1 antibody comprises a heavy chain sequence having the amino acid sequence of SEQ ID NO: 13. In one embodiment, the antigen-binding portion of the anti-human CHI3L1 antibody comprises a light chain sequence having the amino acid sequence of SEQ ID NO: 14.

In one embodiment, the antigen-binding portion of the anti-human PD-1 antibody comprises the amino acid sequence of SEQ ID NO: 35.

As described herein, the bispecific antibodies of the present invention had remarkable antitumor effects. These bispecific antibodies manifested enhance synergistic cytotoxic effects compared to the effects of individual CHI3L1 and PD-1 antibodies, alone or in combination. The bispecific antibodies of the present invention (i) enhance Jurkat T cell attachment to U87 cells; (ii) enhance the ability of Jurkat T cell to induce cytotoxic/apoptotic responses in U87 cells; (iii) enhance the accumulation of granzyme and perforin in Jurkat T cells that are in co-culture with U87 cells; and/or (iv) enhance the ability of Jurkat T cell to induce lactate dehydrogenase (LDH) release and cell cytotoxicity responses in U87 cells.

The embodiments of the present invention also provide pharmaceutical compositions comprising the bispecific antibodies of the present invention and a pharmaceutically acceptable carrier. In one embodiment, the pharmaceutical composition further comprises a chemotherapeutic agent.

The embodiments of the present invention also provide methods of treating cancer in a subject by administering a therapeutically-effective amount of the bispecific antibodies or pharmaceutical compositions of the present invention. In one embodiment, the cancer is malignant cancer. In one embodiment, the cancer is a primary cancer or a metastatic cancer. In one embodiment, the cancer is one of prostate cancer, colon cancer, rectal cancer, ovarian cancer, kidney cancer, breast cancer, glioblastoma, melanoma, malignant melanoma, or lung cancer. In one embodiment, the subject is subject determined to have an elevated level of CHI3L1. In one embodiment, the elevated CHI3L1 level is circulating CHI3L1. In one embodiment, the cancer expresses PD-L1.

The bispecific antibodies of the present invention target CHI3L1 and PD-1 and have antitumor cytotoxic effects that exceed the effects of anti-CHI3L1 and anti-PD-1 antibodies, alone or in combination.

Other implementations are also described and recited herein.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings:

FIG. 1B: CHI3L1-HCxScFv-HC-PD1-ScFv-LC-PD1 (CHI3L1-HC-PD1).

FIG. 2A shows the evaluation against recombinant human (rh) CHI3L1; FIG. 2B shows the evaluation against rhPD1; and FIG. 2C shows the evaluation against rhCHI3L1 and rhPD1 mixtures. There were no differences in the binding affinities to rhCHI3L1 or rhPD1 between CHI3L1-LC-PD1 and CHI3L1-HC-PD1 antibodies.

In FIG. 3A, CellBrite cytoplasmic membrane dye was used for fluorescent labelling of U87 (red) and Jurkat T cells (green). FIG. 3B shows phase contrast images, which were captured after 6 hrs of incubation with IgG control and indicated antibodies (5 mg/ml, each). Isotype, IgG control antibody; PD1, a-human PD1 antibody; CHI3L1, a-human CHI3L1 antibody; CHI3L1+ PD1, a-CHI3L1 antibody plus a-PD1 antibody together; CHI3L1xPD1, bispecific CHI3L1–PD1 antibody. FIG. 3C shows the number of Jurkat T cells attached to each U87 cell assessed via counted fluorescence microscopy (×20 of original magnification; 10 randomly selected areas were included for this evaluation). Values are mean±SEM. *p<0.05, **p<0.01 by t-test.

In FIG. 4A-B, CellBrite cytoplasmic membrane dye was used for fluorescent labelling of live cells (Green) and propidium iodide staining for dead cells (Red). After 6 hours of incubation, cells were treated with vehicle only (FIG. 4A) and IgG2b isotype control or indicated antibodies (5 mg/ml, each) (FIG. 4B) and fluorescent images were captured. In FIG. 4C, TUNEL stains and images were captured under bright-field microscope. FIG. 4D shows the quantitation of TUNEL positive apoptotic U87 cells. TUNEL positive apoptotic cells were counted under light microscope (×20 of original magnification) and expressed as % of total cells evaluated (10 microscopic fields were randomly selected and used for this evaluation). Values are mean±SEM. *p<0.05, **p<0.01 by t-test.

FIG. 5B shows the quantitation of Granzyme+cells. The number of granzyme+ cells were counted under fluorescence microscopy (×20 of original magnification; 10 randomly selected areas were included in this evaluation). Values are mean±SEM. *p<0.05 by t-test.

FIG. 6B shows the quantitation of perforin positive (+) cells. Average number of Perforin+cells per microscopic field were counted (×20 of original magnification). Isotype, IgG2b control antibody; PD1, anti-human PD1 antibody; CHI3L1, anti-human CHI3L1 antibody; CHI3L1+PD1, anti-CHI3L1 antibody plus anti-PD1 antibody together; CHI3L1xPD1, bispecific CHI3L1xPD1 antibody. x20 of original magnification. Values are mean±SEM. *p<0.05, **p<0.01 by t-test.

5
6

Figure 8:
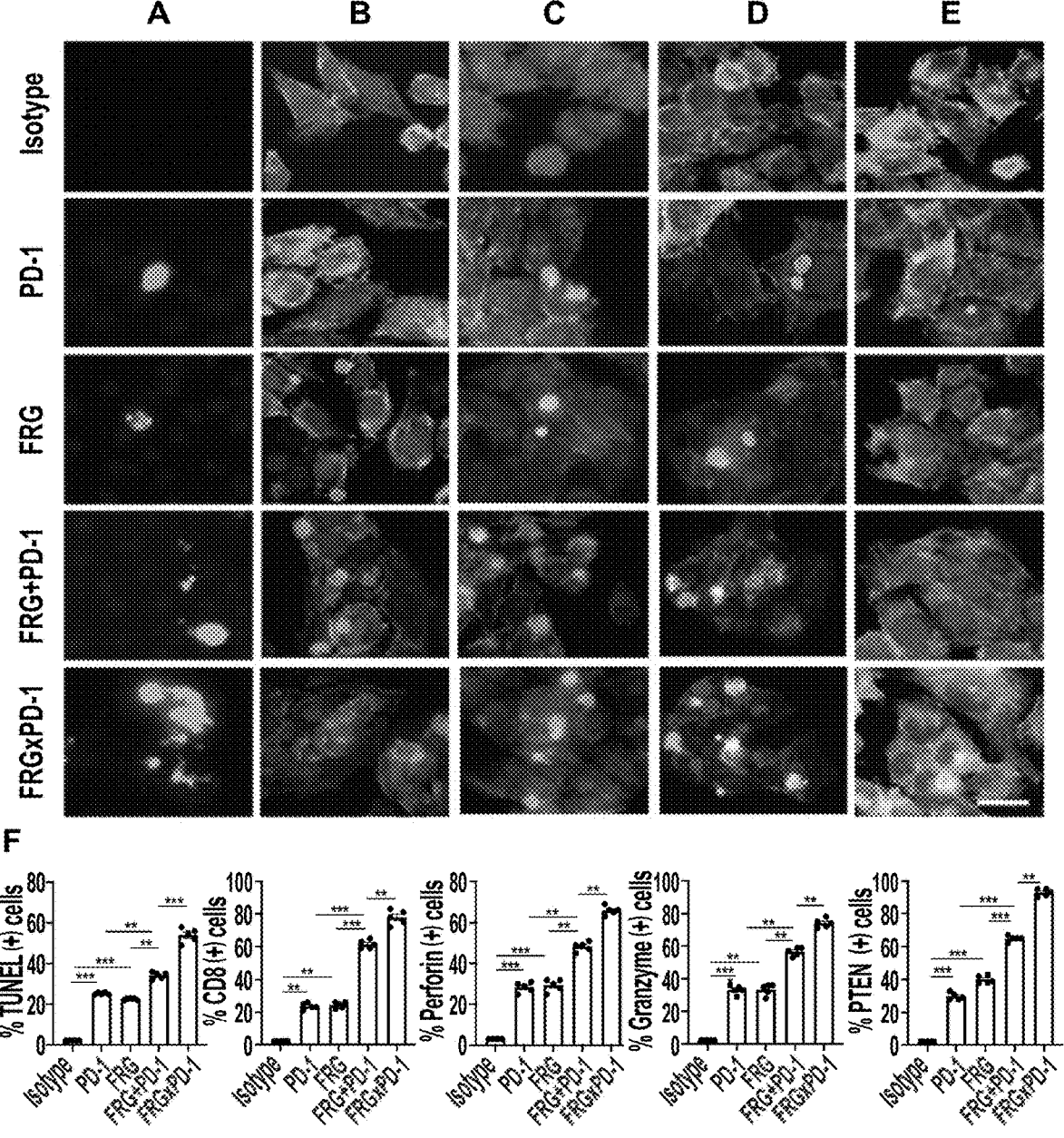

FIG. 8 shows that bispecific CHI3L1xPD1 antibody treatment induced synergistic CTL-mediated tumor cell death responses and tumor cell PTEN expression. (Column A) Representative demonstration and quantitation of apoptotic tumor cell death using in situ cell detection kit-fluorescein dUTP. TUNEL (+) cells stain green. (Columns B-D) Representative demonstration and quantification of Jurkat T cell expression of CD8 (Column B), perforin (Column C) and granzyme (Column D). Tumor cells are green and positive staining Jurkat cells are yellow-orange. (Column E) Representative demonstration and quantification of tumor cell PTEN. Tumor cells are green and PTEN is yellow-orange. (Row F) Quantification of the evaluations in Columns A-E. The % of TUNEL+tumor cells (Column A), % of Jurkat cells expressing CD8 (Column B), perforin (Column C) and granzyme (Column D) and % of tumor cells expressing PTEN (Column E) are illustrated. These evaluations were done using fluorescent microscopy (×20 of original magnification). In these quantifications, 10 randomly selected fields were evaluated. The values in panel F are the mean±SEM of the noted 4 evaluations. P<0.01. *P<0.001. Scale bar=10 μm, applies to all subpanels of A-E.

DETAILED DESCRIPTION OF THE INVENTION

It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The abbreviation, "e.g." is derived from the Latin exempli gratia, and is used herein to indicate a non-limiting example. Thus, the abbreviation "e.g." is synonymous with the term "for example."

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The term "statistically significant" or "significantly" refers to statistical significance and generally means a two standard deviation (2SD) or greater difference.

As used herein, the phrase "therapeutically effective amount", "effective amount" or "effective dose" refers to an amount that provides a therapeutic or aesthetic benefit in the treatment, prevention, or management of a tumor or malignancy, e.g., an amount that provides a statistically significant decrease in at least one symptom, sign, or marker of a tumor or malignancy. It will be appreciated that there will be many ways known in the art to determine the effective amount for a given application. For example, the pharmacological methods for dosage determination may be used in the therapeutic context. In the context of therapeutic or prophylactic applications, the amount of a composition administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions can also be administered in combination with one or more additional therapeutic compounds.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of a tumor or malignancy, delay or slowing of tumor growth and/or metastasis, and an increased lifespan as compared to that expected in the absence of treatment.

As used herein, the term "administering," refers to the placement of a bispecific antibody, as disclosed herein, into a subject by a method or route which results in at least partial delivery of the agent at a desired site. Pharmaceutical compositions comprising the compounds disclosed herein can be administered by any appropriate route which results in an effective treatment in the subject.

As used herein, the term "long-term" administration means that the therapeutic agent or drug is administered for a period of at least 12 weeks. This includes that the therapeutic agent or drug is administered such that it is effective over, or for, a period of at least 12 weeks and does not necessarily imply that the administration itself takes place for 12 weeks, e.g., if sustained release compositions or long acting therapeutic agent or drug is used. Thus, the subject is treated for a period of at least 12 weeks. In many cases, long-term administration is for at least 4, 5, 6, 7, 8, 9 months or more, or for at least 1, 2, 3, 5, 7 or 10 years, or more.

The administration of the compositions contemplated herein may be carried out in any convenient manner, including by aerosol inhalation, injection, ingestion, transfusion, implantation or transplantation. In a preferred embodiment, compositions are administered parenterally. The phrases "parenteral administration" and "administered parenterally" as used herein refers to modes of administration other than enteral and topical administration, usually by injection, and includes, without limitation, intravascular, intravenous, intramuscular, intraarterial, intrathecal, intracapsular, intraorbital, intratumoral, intracardiac, intradermal, intraperitoneal, transtracheal, subcutaneous, subcuticular, intraarticular, subcapsular, subarachnoid, intraspinal and intrasternal injection and infusion. In one embodiment, the compositions contemplated herein are administered to a subject by direct injection into a tumor, lymph node, or site of infection.

As used herein, the term "cancer" relates generally to a class of diseases or conditions in which abnormal cells divide without control and can invade nearby tissues. Cancer cells can also spread to other parts of the body through the blood and lymph systems. There are several main types of cancer. Carcinoma is a cancer that begins in the skin or in tissues that line or cover internal organs. Sarcoma is a cancer that begins in bone, cartilage, fat, muscle, blood vessels, or other connective or supportive tissue. Leukemia is a cancer that starts in blood-forming tissue such as the bone marrow, and causes large numbers of abnormal blood cells to be produced and enter the blood. Lymphoma and multiple myeloma are cancers that begin in the cells of the immune system. Central nervous system cancers are cancers that begin in the tissues of the brain and spinal cord.

In some embodiments of any of the aspects, the cancer is a primary cancer. In some embodiments of any of the aspects, the cancer is a malignant cancer. As used herein, the term "malignant" refers to a cancer in which a group of tumor cells display one or more of uncontrolled growth (i.e., division beyond normal limits), invasion (i.e., intrusion on and destruction of adjacent tissues), and metastasis (i.e., spread to other locations in the body via lymph or blood). As used herein, the term "metastasize" refers to the spread of cancer from one part of the body to another. A tumor formed by cells that have spread is called a "metastatic tumor" or a "metastasis." The metastatic tumor contains cells that are like those in the original (primary) tumor.

As used herein, the term "benign" or "non-malignant" refers to tumors that may grow larger but do not spread to other parts of the body. Benign tumors are self-limited and typically do not invade or metastasize.

A "cancer cell" or "tumor cell" refers to an individual cell of a cancerous growth or tissue. A tumor refers generally to a swelling or lesion formed by an abnormal growth of cells, which may be benign, pre-malignant, or malignant. Most cancer cells form tumors, but some, e.g., leukemia, do not necessarily form tumors. For those cancer cells that form tumors, the terms cancer (cell) and tumor (cell) are used interchangeably.

A subject that has a cancer or a tumor is a subject having objectively measurable cancer cells present in the subject's body. Included in this definition are malignant, actively proliferative cancers, as well as potentially dormant tumors or micrometastatses. Cancers which migrate from their original location and seed other vital organs can eventually lead to the death of the subject through the functional deterioration of the affected organs. Hemopoietic cancers, such as leukemia, are able to out-compete the normal hemopoietic compartments in a subject, thereby leading to hemopoietic failure (in the form of anemia, thrombocytopenia and neutropenia) ultimately causing death.

Examples of cancer include but are not limited to, carcinoma, lymphoma, blastoma, sarcoma, leukemia, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma (GBM); hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

A "cancer cell" is a cancerous, pre-cancerous, or transformed cell, either in vivo, ex vivo, or in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage independence, malignancy, loss of contact inhibition and density limitation of growth, growth factor or serum independence, tumor specific markers, invasiveness or metastasis, and tumor growth in suitable animal hosts such as nude mice.

A subject can be one who has been previously diagnosed with or identified as suffering from or having a condition in need of treatment (e.g., a cancer) or one or more complications related to such a condition, and optionally, but need not have already undergone treatment for a condition or the one or more complications related to the condition. Alternatively, a subject can also be one who has not been previously diagnosed as having a condition in need of treatment or one or more complications related to such a condition. For example, a subject can be one who exhibits one or more risk factors for a condition or one or more complications related to a condition or a subject who does not exhibit risk factors. A "subject in need" of treatment for a particular condition can be a subject having that condition, diagnosed as having that condition, or at risk of developing that condition. As explained further herein, in some embodiments, the subject is a subject determined to have an elevated level of CHI3L1. In some embodiments, the CHI3L1 is circulating CHI3L1. In some embodiments, the subject is afflicted with a cancer that expresses PD-L1.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

In some embodiments, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments, the polypeptide described herein can be a variant of a sequence described herein. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments, a nucleic acid encoding a polypeptide as described herein (e.g., an antibody or antibody reagent) is comprised by a vector. In some of the aspects described herein, a nucleic acid sequence encoding a given polypeptide as described herein, or any module thereof, is operably linked to a vector. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated." The terms "purified" or "substantially purified" refer to an isolated nucleic acid or polypeptide that is at least 95% by weight the subject nucleic acid or polypeptide, including, for example, at least 96%, at least 97%, at least 98%, at least 99% or more. In some embodiments, the antibody, antigen-binding portion thereof, or chimeric antigen receptor (CAR) described herein is isolated. In some embodiments, the antibody, antibody reagent, antigen-binding portion thereof, or CAR described herein is purified.

As used herein, "engineered" refers to the aspect of having been manipulated by the hand of man. For example, an antibody, antibody reagent, antigen-binding portion thereof, CAR or bispecific antibody is considered to be "engineered" when the sequence of the antibody, antibody reagent, antigen-binding portion thereof, CAR or bispecific antibody is manipulated by the hand of man to differ from the sequence of an antibody as it exists in nature. As is common practice and is understood by those in the art, progeny and copies of an engineered polynucleotide and/or polypeptide are typically still referred to as "engineered" even though the actual manipulation was performed on a prior entity.

As used herein, an "epitope" can be formed on a polypeptide both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin VH/VL pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics.

As used herein, the term "antibody" refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and antigen-binding portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding portion thereof, and/or bifunctional hybrid antibodies.

Each heavy chain is composed of a variable region of said heavy chain (abbreviated here as HCVR or VH) and a constant region of said heavy chain. The heavy chain constant region consists of three domains CH1, CH2 and CH3. Each light chain is composed of a variable region of said light chain (abbreviated here as LCVR or VL) and a constant region of said light chain. The light chain constant region consists of a CL domain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4. This structure is well known to those skilled in the art.

As used herein, the term "CDR" refers to the complementarity determining regions within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems. The system described by Kabat et al. (1987) and (1991) not only provides an unambiguous residue numbering system applicable to any variable region of an antibody, but also provides precise residue boundaries defining the three CDRs. These CDRs may be referred to as Kabat CDRs. Other boundaries defining CDRs overlapping with the Kabat CDRs have been described by Padlan et al. (1995), MacCallum et al. (1996), and Chothia et al. (1987) and (1989). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat defined CDRs.

The term "antigen-binding portion" of an antibody refers to one or more portions of an antibody as described herein, said portions) still having the binding affinities as defined above herein. Portions of a complete antibody have been shown to be able to carry out the antigen-binding function of an antibody. In accordance with the term "antigen-binding portion" of an antibody, examples of binding portions include (i) an Fab portion, i.e., a monovalent portion composed of the VL, VH, CL and CH1 domains; (ii) an F(ab')2 portion, i.e., a bivalent portion comprising two Fab portions linked to one another in the hinge region via a disulfide bridge; (iii) an Fd portion composed of the VH and CH1 domains; (iv) an Fv portion composed of the FL and VH domains of a single arm of an antibody; and (v) a dAb portion consisting of a VH domain or of VH, CH1, CH2, DH3, or VH, CH2, CH3 (dAbs, or single domain antibodies, comprising only Vdomains have also been shown to specifically bind to target epitopes). Although the two domains of the Fv portion, namely VL and VH, are encoded by separate genes, they may further be linked to one another using a synthetic linker, e.g., a poly-G4S amino acid sequence ('G4S' disclosed as SEQ ID NO: 29 in U.S. Pat. No. 10,253,111) ("G4S" disclosed as SEQ ID NO: 36 in instant application), and recombinant methods, making it possible to prepare them as a single protein chain in which the VL and VH regions combine in order to form monovalent molecules (known as single chain Fv (ScFv)). The term "antigen-binding portion" of an antibody is also intended to comprise such single chain antibodies. Other forms of single chain antibodies such as "diabodies" are likewise included here. Diabodies are bivalent, bispecific antibodies in which VH and VL domains are expressed on a single polypeptide chain, but using a linker which is too short for the two domains being able to combine on the same chain, thereby forcing said domains to pair with complementary domains of a different chain and to form two antigen-binding sites. An immunoglobulin constant domain refers to a heavy or light chain constant domain. Human IgG heavy chain and light chain constant domain amino acid sequences are known in the art.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments as well as complete antibodies.

An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

Furthermore, an antibody, antigen-binding portion thereof, or CAR as described herein may be part of a larger immunoadhesion molecule formed by covalent or noncovalent association of said antibody or antibody portion with one or more further proteins or peptides. Relevant to such immunoadhesion molecules are the use of the streptavidin core region in order to prepare a tetrameric scFv molecule and the use of a cysteine residue, a marker peptide and a C-terminal polyhistidinyl, e.g., hexahistidinyl tag ('hexahistidinyl tag' disclosed as SEQ ID NO: 30 in U.S. Pat. No. 10,253,111) ("hexahistidinyl tag" disclosed as SEQ ID NO: 37 in instant application) in order to produce bivalent and biotinylated scFv molecules.

In some embodiments, the antibody, antibody reagent, antigen-binding portion thereof, or CAR described herein can be an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, an anti-idiotypic antibody, a bispecific antibody, and a functionally active epitope-binding portion thereof.

In some embodiments, the antibody or antigen-binding portion thereof is a fully human antibody. In some embodiments, the antibody, antigen-binding portion thereof, is a humanized antibody or antibody reagent. In some embodiments, the antibody, antigen-binding portion thereof, is a fully humanized antibody or antibody reagent. In some embodiments, the antibody or antigen-binding portion thereof, is a chimeric antibody or antibody reagent. In some embodiments, the antibody, antigen-binding portion thereof, is a recombinant polypeptide. In some embodiments, the CAR comprises an extracellular domain that binds CHI3L1, wherein the extracellular domain comprises a humanized or chimeric antibody or antigen-binding portion thereof.

The term "human antibody" refers to antibodies whose variable and constant regions correspond to or are derived from immunoglobulin sequences of the human germ line, as described, for example, by Kabat et al. (1991). However, the human antibodies can contain amino acid residues not encoded by human germ line immunoglobulin sequences (for example mutations which have been introduced by random or site-specific mutagenesis in vitro or by somatic mutation in vivo), for example in the CDRs, and in particular in CDR3. Recombinant human antibodies as described herein have variable regions and may also contain constant regions derived from immunoglobulin sequences of the human germ line. See, Kabat, et al. (1991). According to particular embodiments, however, such recombinant human antibodies are subjected to in vitro mutagenesis (or to a somatic in vivo mutagenesis, if an animal is used which is transgenic due to human Ig sequences) so that the amino acid sequences of the VH and VL regions of the recombinant antibodies are sequences which although related to or derived from VH and VL sequences of the human germ line, do not naturally exist in vivo within the human antibody germ line repertoire. According to particular embodiments, recombinant antibodies of this kind are the result of selective mutagenesis or back mutation or of both. Preferably, mutagenesis leads to an affinity to the target which is greater, and/or an affinity to non-target structures which is smaller than that of the parent antibody. Generating a humanized antibody from the sequences and information provided herein can be practiced by those of ordinary skill in the art without undue experimentation. In one approach, there are four general steps employed to humanize a monoclonal antibody, see, e.g., U.S. Pat. Nos. 5,585,089; 6,835,823; 6,824,989. These are: (1) determining the nucleotide and predicted amino acid sequence of the starting antibody light and heavy variable domains; (2) designing the humanized antibody, i.e., deciding which antibody framework region to use during the humanizing process; (3) the actual humanizing methodologies/techniques; and (4) the transfection and expression of the humanized antibody.

In some embodiments, the bispecific antibody, antibody reagent, antigen-binding portion thereof, and/or CAR as described herein can be a variant of a sequence described herein, e.g., a conservative substitution variant of an antibody polypeptide. In some embodiments, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or portion thereof that retains activity, e.g., antigen-specific binding activity for the relevant target polypeptide, e.g., CHI3L1 or PD-1. A wide variety of PCR-based site-specific mutagenesis approaches are also known in the art and can be applied by the ordinarily skilled artisan.

Usually the CDR regions in humanized antibodies and human antibody variants are substantially identical, and more usually, identical to the corresponding CDR regions in the mouse or human antibody from which they were derived. In some embodiments, it is possible to make one or more conservative amino acid substitutions of CDR residues without appreciably affecting the binding affinity of the resulting humanized immunoglobulin or human antibody variant. In some embodiments, substitutions of CDR regions can enhance binding affinity.

The term "chimeric antibody" refers to antibodies which contain sequences for the variable region of the heavy and light chains from one species and constant region sequences from another species, such as antibodies having murine heavy and light chain variable regions linked to human constant regions. Humanized antibodies have variable region framework residues substantially from a human antibody (termed an acceptor antibody) and complementarity determining regions substantially from a non-human antibody, e.g., a mouse-antibody, (referred to as the donor immunoglobulin). The constant region(s), if present, are also substantially or entirely from a human immunoglobulin. The human variable domains are usually chosen from human antibodies whose framework sequences exhibit a high degree of sequence identity with the (murine) variable region domains from which the CDRs were derived. The heavy and light chain variable region framework residues can be substantially similar to a region of the same or different human antibody sequences. The human antibody sequences can be the sequences of naturally occurring human antibodies or can be consensus sequences of several human antibodies.

In addition, techniques developed for the production of "chimeric antibodies" by splicing genes from a mouse, or other species, antibody molecule of appropriate antigen specificity together with genes from a human antibody molecule of appropriate biological activity can be used. The variable segments of chimeric antibodies are typically linked to at least a portion of an immunoglobulin constant region (Fc), typically that of a human immunoglobulin. Human constant region DNA sequences can be isolated in accordance with well-known procedures from a variety of human cells, such as immortalized B-cells. The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Additionally, and as described herein, a recombinant humanized antibody can be further optimized to decrease potential immunogenicity, while maintaining functional activity, for therapy in humans. In this regard, functional activity means a polypeptide capable of displaying one or more known functional activities associated with a recombinant antibody, antigen-binding portion thereof, or CAR as described herein. Such functional activities include binding to cancer cells and/or anti-cancer activity. Additionally, a polypeptide having functional activity means the polypeptide exhibits activity similar, but not necessarily identical to, an activity of a reference antibody, antigen-binding portion thereof, or CAR as described herein, including mature forms, as measured in a particular assay, such as, for example, a biological assay, with or without dose dependency. In the case where dose dependency does exist, it need not be identical to that of the reference antibody, antigen-binding portion thereof, or CAR, but rather substantially similar to the dose-dependence in a given activity as compared to the reference antibody, antigen-binding portion thereof, or CAR as described herein (i.e., the candidate polypeptide will exhibit greater activity, or not more than about 25-fold less, about 10-fold less, or about 3-fold less activity relative to the antibodies, antigen-binding portions, and/or CARs described herein).

In some embodiments, the antibody reagents (e.g., antibodies or CARs) described herein are not naturally-occurring biomolecules. For example, a murine antibody raised against an antigen of human origin would not occur in nature absent human intervention and manipulation, e.g., manufacturing steps carried out by a human. Chimeric antibodies are also not naturally-occurring biomolecules, e.g., in that they comprise sequences obtained from multiple species and assembled into a recombinant molecule. In certain particular embodiments, the human antibody reagents described herein are not naturally-occurring biomolecules, e.g., fully human antibodies directed against a human antigen would be subject to negative selection in nature and are not naturally found in the human body.

In some embodiments, the antibody, antibody reagent, antigen-binding portion thereof, and/or CAR is an isolated polypeptide. In some embodiments, the antibody, antibody reagent, antigen-binding portion thereof, and/or CAR is a purified polypeptide. In some embodiments, the antibody, antibody reagent, antigen-binding portion thereof, and/or CAR is an engineered polypeptide.

"Avidity" is the measure of the strength of binding between an antigen-binding molecule (such as an antibody or antigen-binding portion thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or portion of an antibody as described herein) will bind to their cognate or specific antigen with a dissociation constant ($K_D$ of $10^{-5}$ to $10^{-12}$ moles/liter or less, such as $10^{-7}$ to $10^{-12}$ moles/liter or less, or $10^{-8}$ to $10^{-12}$ moles/liter (i.e., with an association constant ($K_A$) of $10^5$ to $10^{12}$ liter/moles or more, such as $10^7$ to $10^{12}$ liter/moles or $10^8$ to $10^{12}$ liter/moles). Any $K_D$ value greater than $10^{-4}$ mol/liter (or any $K_A$ value lower than $10^4$ M$^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction, the lower is its $K_D$. For example, a binding site on an antibody or portion thereof described herein will bind to the desired antigen with an affinity less than 500 nM, such as less than 200 nM, or less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of a peptide (e.g., an antibody, CAR, bispecific antibody or portion thereof) described herein to bind to a target, such as an antigen present on the cell-surface of a cancer cell, with a KD $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay. A polypeptide specifically bound to a target is not displaced by a non-similar competitor. In certain embodiments, an antibody, antigen-binding portion thereof, CAR or bispecific antibody is said to specifically bind an antigen when it preferentially recognizes its target antigen in a complex mixture of proteins and/or macromolecules.

In some embodiments, a bispecific antibody, antigen-binding portion thereof, or CAR, as described herein, binds to CHI3L1 and PD-1 with a dissociation constant ($K_D$) of $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. In some embodiments, a bispecific antibody, antigen-binding portion thereof, or CAR, as described herein, binds to CHI3L1 and PD-1 with a dissociation constant ($K_D$) of from about $10^{-5}$ M to $10^{-6}$ M. In some embodiments, a bispecific antibody, antigen-binding portion thereof, or CAR, as described herein, binds to CHI3L1 and PD-1 with a dissociation constant ($K_D$) of from about $10^{-6}$ M to $10^{-7}$ M. In some embodiments, a bispecific antibody, antigen-binding portion thereof, or CAR, as described herein, binds to CHI3L1 and PD-1 with a dissociation constant ($K_D$) of from about $10^{-7}$ M to $10^{-8}$ M. In some embodiments, a bispecific antibody, antigen-binding portion thereof, or CAR, as described herein, binds to CHI3L1 and PD-1 with a dissociation constant ($K_D$) of from about $10^{-8}$ M to $10^{-9}$ M. In some embodiments, a bispecific antibody, antigen-binding portion thereof, or CAR, as described herein, binds to CHI3L1 and PD-1 with a dissociation constant ($K_D$) of from about $10^{-9}$ M to $10^{-10}$ M. In some embodiments, a bispecific antibody, antigen-binding portion thereof, or CAR, as described herein, binds to CHI3L1 and PD-1 with a dissociation constant ($K_D$) of from about $10^{-10}$ M to $10^{-11}$ M. In some embodiments, a bispecific antibody, antigen-binding portion thereof, or CAR, as described herein, binds to CHI3L1 and PD-1 with a dissociation constant ($K_D$) of from about $10^{-11}$ M to $10^{-12}$ M. In some embodiments, a bispecific antibody, antigen-binding portion thereof, or CAR, as described herein, binds to CHI3L1 and/or PD-1 with a dissociation constant ($K_D$) of less than $10^{-12}$ M.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only and is not intended to limit the scope of the present invention, which is defined solely by the claims. Definitions of common terms in immunology and molecular biology can be found in THE MERCK MANUAL OF DIAGNOSIS AND THERAPY, 19th (2011); THE ENCYCLOPEDIA OF MOLECULAR CELL BIOLOGY AND MOLECULAR MEDICINE, (1999-2012); MOLECULAR BIOLOGY AND BIOTECHNOLOGY: A COMPREHENSIVE DESK REFERENCE, (1995); IMMUNOLOGY (2006); JANEWAY'S IMMUNOBIOLOGY (2014); LEWIN'S GENES XI (2014); MOLECULAR CLONING: A LABORATORY MANUAL, 4$^{th}$ ed. (2012); BASIC METHODS IN MOLECULAR BIOLOGY (2012); LABORATORY METHODS IN ENZYMOLOGY: DNA (2013); CURRENT PROTOCOLS IN MOLECULAR BIOLOGY (CPMB) (2014); CURRENT PROTOCOLS IN PROTEIN SCIENCE (CPPS) (2005); and CURRENT PROTOCOLS IN IMMUNOLOGY (CPI) (2003), the contents of which are all incorporated by reference herein in their entireties.

One of skill in the art can readily identify a chemotherapeutic agent of use. See, e.g., PHYSICIANS' CANCER CHEMOTHERAPY DRUG MANUAL (2014); Chapter 85 in HARRISON'S PRINCIPLES OF INTERNAL MEDICINE, 18$^{th}$ edition (2011); Chapters 28-29 in ABELOFFS CLINICAL ONCOLOGY, 5$^{th}$ edition (2013); and THE CANCER CHEMOTHERAPY HANDBOOK, 4$^{th}$ edition (2003).

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

Bispecific Antibodies of the Present Invention

Immunotherapy with anti-programmed death-1 (PD-1) or anti-PD-1 ligand 1 (PD-L1) antibodies has been approved for the treatment of several cancers because of impressive durable responses; however, overall, only a small percentage of patients currently benefit from PD-1 blockade therapy alone (Topalian et al., 2012; Herbst et al., 2014; Powles et al., 2014; Ansell et al., 2015; Garon et al., 2015; Postow et al., 2015; Robert et al., 2015a,b; Weber et al., 2015; Nghiem et al., 2016; Ribas et al., 2016). The combination of anti-PD-1/L1 antibodies with other immune modulating agents seems to be more active, but it adds significant toxicities (Wolchok et al., 2013; Larkin et al., 2015; Postow et al., 2015).

In our previous work, we demonstrated that inhibiting (a) CHI3L1 and/or CHI3L1 signaling and (b) at least one immune checkpoint protein, such as PD-1, provided synergistic effects in the treatment of cancer, e.g., lung cancer. See, e.g., U.S. Published Application No. 2019/0062457. When the anti-CHI3L1 antibody, FRG, was administered in combination with an anti-PD-1 antibody, synergism was observed, with the combination displaying improved efficacy in reducing B16F10 metastasis, thereby suggesting that the combination of CHI3L1 inhibition and inhibition of a checkpoint protein provides synergistic efficacy in the treatment of cancer. See Example 2 of U.S. Published Application No. 2019/0062457. It was hypothesized that a bispecific antibody that specifically bind both a CHI3L1 polypeptide and a PD-1 polypeptide and simultaneously detect and neutralize both CHI3L1 and the immune checkpoint inhibitor PD-1 could display an improved synergistic efficacy in the treatment of cancer.

Described herein are bispecific antibodies, antibody reagents, antigen-binding fragments thereof, or chimeric antigen receptors (CARs) that specifically bind both a CHI3L1 polypeptide and a PD-1 polypeptide and simultaneously detect and neutralize both CHI3L1 and the immune checkpoint inhibitor PD-1. Such bispecific antibodies, antigen binding portions thereof, etc., can permit, e.g., the diagnosis, prognosis, and/or treatment of cancer. In some embodiments, the technology described herein relates to chimeric antigen receptors (CARs) and CAR-T therapy for cancer. In some embodiments, the technology described herein relates to monoclonal antibody therapy for cancer. In some embodiments, the technology described herein relates to antibody-drug conjugates for the treatment of cancer.

Described herein are methods and compositions relating to bispecific anti-CHI3L1 and anti-PD-1 antibodies, antibody reagents, and antigen-binding fragments thereof which display superior properties, e.g., high sensitivity, high specificity, high binding affinity, neutralization activity ex vivo and in vivo. Methods of treatment, e.g., of treating cancer, by administering the compounds described herein are also provided.

The bispecific antibodies of the present invention comprise an antigen-binding portion of an anti-human PD-1 antibody and an antigen-binding portion of an anti-human CHI3L1 antibody. In some embodiments, the bispecific antibodies comprise an anti-human PD-1 single chain variable fragment (ScFv-PD1) attached to the backbone of an anti-human CHI3L1 antibody. In alternative embodiments, the bispecific antibodies comprise an anti-human CHI3L1 single chain variable fragment (ScFv-CHI3L1) attached to the backbone of an anti-human PD-1 antibody.

One of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retain the ability to specifically bind the target antigen (e.g., CHI3L1 and PD-1). Such conservatively modified variants are in addition to and do not exclude polymorphic variants, interspecies homologs, and alleles consistent with the disclosure.

Examples of substitution variants include conservative substitution of amino acids, e.g., in a $V_H$ or $V_L$, domain, that do not alter the sequence of a CDR. A conservative substitution in a sequence not comprised by a CDR can be a substitution relative to a wild-type or naturally-occurring sequence, e.g., human or murine framework and/or constant regions of an antibody sequence.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gin and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g., antigen-binding activity and specificity of a native or reference polypeptide is retained.

Amino acids can be grouped according to similarities in the properties of their side chains (BIOCHEMISTRY, $2^{nd}$ edition, (1975) at pp. 73-75): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gin (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gin; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gin or into H is; Asp into Glu; Cys into Ser; Gin into Asn; Glu into Asp; Gly into Ala or into Pro; His into Asn or into Gin; Ile into Leu or into Val; Leu into Ile or into Val; Lys into Arg, into Gin or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

A variant amino acid or DNA sequence preferably is at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g., BLASTp or BLASTn with default settings).

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required.

Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

In particular embodiments wherein an antibody, antigen-binding portion thereof, or CAR as described herein comprises at least one CDR which is not identical to the sequence of CHI3L1 and PD-1 CDR provided herein, the amino acid sequence of that at least one CDR can be selected by methods well known to one of skill in the art. For example, Fujii, 2004, "Antibody affinity maturation by random mutagenesis" in Methods in Molecular Biology: Antibody Engineering 248: 345-349 (incorporated by reference herein in its entirety), particularly at FIG. 2 and Section 3.3, describes methods of generating a library for any CDR of interest. This allows one of ordinary skill in the art to identify alternative CDRs, including conservative substitution variants of the specific CDR sequences described herein, which, when present in an antibody or antigen-binding portion thereof as described herein, will result in an antigen or antigen-binding portion thereof which will bind a cancer cell surface antigen. The method described in Fujii et al. also permits one of ordinary skill in the art to screen for a light chain sequence which will give the desired binding behavior when combined with a known heavy chain fragment and vice versa.

In some embodiments, a CAR comprises an extracellular domain comprising an anti-CHI3L1 antibody or antigen-binding portion thereof that binds one or more epitopes of a CHI3L1 polypeptide; a transmembrane domain, one or more intracellular co-stimulatory signaling domains, and a primary signaling domain. Exemplary anti-CHI3L1 and anti-PD-1 antibodies and antigen-binding portions thereof, as well as exemplary epitopes, are described elsewhere herein.

As used herein, "chimeric antigen receptor" or "CAR" refers to an artificially constructed hybrid polypeptide comprising an antigen-binding domain (e.g., an antigen-binding portion of an antibody (e.g., a scFv)), a transmembrane domain, and a T cell signaling and/or T cell activation domain. CARs have the ability to redirect T cell specificity and reactivity toward a selected target in a non-MHC-restricted manner, exploiting the antigen-binding properties of monoclonal antibodies. The non-MHC-restricted antigen recognition gives T cells expressing CARs the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fab's (instead of from an antibody, e.g., obtained from Fab libraries), in various embodiments, this scFv is fused to a transmembrane domain and then to an intracellular signaling domain. "First-generation" CARs include those that solely provide CD3zeta (CDζ) signals upon antigen binding, "Second-generation" CARs include those that provide both co-stimulation (e.g., CD28 or CD 137) and activation (CD3). "Third-generation" CARs include those that provide multiple costimulatory (e.g., CD28 and CD 137) domains and activation domains (e.g., CD3). In various embodiments, the CAR is selected to have high affinity or avidity for the antigen. Further discussion of CARs can be found, e.g., in Maus et al. (2014); Reardon et al. (2014); Hoyos et al. (2012); Byrd et al. (2014); Maher and Wilkie (2009); and Tamada et al. (2012), each of which is incorporated by reference herein in its entirety.

In some embodiments of any of the aspects, a CAR comprises an extracellular binding domain that comprises a humanized CHI3L1-specific or a humanized PD-1-specific binding domain; a transmembrane domain; one or more intracellular co-stimulatory signaling domains; and a primary signaling domain. As used herein, the terms, "binding domain," "extracellular domain," "extracellular binding domain," "antigen-specific binding domain," and "extracellular antigen specific binding domain," are used interchangeably and provide a CAR with the ability to specifically bind to the target antigen of interest, e.g., CHI3L1 and PD-1. The binding domain may be derived either from a natural, synthetic, semi-synthetic, or recombinant source.

In some embodiments, the CARs contemplated herein may comprise linker residues between the various domains, e.g., added for appropriate spacing and conformation of the molecule. In particular embodiments the linker is a variable region linking sequence. A "variable region linking sequence," is an amino acid sequence that connects the VH and VL domains and provides a spacer function compatible with interaction of the two sub-binding domains so that the resulting polypeptide retains a specific binding affinity to the same target molecule as an antibody that comprises the same light and heavy chain variable regions. CARs contemplated herein, can comprise one, two, three, four, or five or more linkers. In particular embodiments, the length of a linker is about 1 to about 25 amino acids, about 5 to about 20 amino acids, or about 10 to about 20 amino acids, or any intervening length of amino acids. In some embodiments, the linker is 1, 2, 3, 4, 5, 6, 7, 8, 9, 10, 11, 12, 13, 14, 15, 16, 17, 18, 19, 20, 21, 22, 23, 24, 25, or more amino acids long.

In particular embodiments, the binding domain of the CAR is followed by one or more "spacer domains," which refers to the region that moves the antigen binding domain away from the effector cell surface to enable proper cell/cell contact, antigen binding and activation. The hinge domain may be derived either from a natural, synthetic, semi-synthetic, or recombinant source. In certain embodiments, a spacer domain is a portion of an immunoglobulin, including, but not limited to, one or more heavy chain constant regions, e.g., CH2 and CH3. The spacer domain can include the amino acid sequence of a naturally occurring immunoglobulin hinge region or an altered immunoglobulin hinge region.

The binding domain of the CAR is generally followed by one or more "hinge domains," which plays a role in positioning the antigen binding domain away from the effector cell surface to enable proper cell/cell contact, antigen binding and activation. A CAR generally comprises one or more hinge domains between the binding domain and the transmembrane domain (TM). The hinge domain may be derived either from a natural, synthetic, semi-synthetic, or recombinant source. The hinge domain can include the amino acid sequence of a naturally occurring immunoglobulin hinge region or an altered immunoglobulin hinge region. Illustrative hinge domains suitable for use in the CARs described herein include the hinge region derived from the extracellular regions of type 1 membrane proteins such as CD8α, CD4, CD28 and CD7, which may be wild-type hinge regions from these molecules or may be altered. In another embodiment, the hinge domain comprises a CD8α hinge region.

The "transmembrane domain" is the portion of the CAR that fuses the extracellular binding portion and intracellular signaling domain and anchors the CAR to the plasma membrane of the immune effector cell. The TM domain may be derived either from a natural, synthetic, semi-synthetic, or recombinant source. The TM domain may be derived from (i.e., comprise at least the transmembrane region(s) of) the alpha, beta or zeta chain of the T cell receptor, CD3ε, CD3ζ, CD4, CD5, CD8α, CD9, CD 16, CD22, CD27, CD28, CD33, CD37, CD45, CD64, CD80, CD86, CD134, CD137, CD152, CD154, and PD1.

In some embodiments, CARs contemplated herein comprise an intracellular signaling domain. An "intracellular signaling domain," refers to the part of a CAR that participates in transducing the message of effective CAR binding to a target antigen into the interior of the immune effector cell to elicit effector cell function, e.g., activation, cytokine production, proliferation and cytotoxic activity, including the release of cytotoxic factors to the CAR-bound target cell, or other cellular responses elicited with antigen binding to the extracellular CAR domain. In some embodiments, a CAR contemplated herein comprises an intracellular signaling domain that comprises one or more "co-stimulatory signaling domain" and a "primary signaling domain."

Primary signaling domains regulate primary activation of the TCR complex either in a stimulatory way, or in an inhibitory way. Primary signaling domains that act in a stimulatory manner may contain signaling motifs which are known as immunoreceptor tyrosine-based activation motifs or ITAMs. Illustrative examples of ITAM containing primary signaling domains that are of particular use in the invention include those derived from TCRζ, FcRγ, FcRβ, CD3γ, CD3ζ, CD3ε, CD3ζ, CD22, CD79a, CD79b, and CD66d.

As used herein, the term, "co-stimulatory signaling domain," or "co-stimulatory domain", refers to an intracellular signaling domain of a co-stimulatory molecule. Co-stimulatory molecules are cell surface molecules other than antigen receptors or Fc receptors that provide a second signal required for efficient activation and function of T lymphocytes upon binding to antigen. Illustrative examples of such co-stimulatory molecules include CARD11, CD2, CD7, CD27, CD28, CD30, CD40, CD54 (ICAM), CD83, CD134 (OX40), CD137 (4-1 BB), CD150 (SLAMF1), CD152 (CTLA4), CD223 (LAG3), CD270 (HVEM), CD273 (PD-L2), CD274 (PD-L1), CD278 (ICOS), DAP10, LAT, NKD2C SLP76, TRIM, and ZAP70. In one embodiment, a CAR comprises one or more co-stimulatory signaling domains selected from the group consisting of CD28, CD137, and CD134, and a CD3 primary signaling domain.

In some embodiments, an antibody-drug conjugate is provided. In particular embodiments, an antibody-drug conjugate comprises an antibody, antibody reagent, or antigen-binding portion thereof as described herein. The drug can be, e.g., a chemotherapeutic molecule as described elsewhere herein. In some embodiments, the antibody-drug conjugate comprises a chemotherapeutic agent directly conjugated and/or bound to an antibody or antigen-binding portion thereof. In some embodiments, binding can be non-covalent, e.g., by hydrogen bonding, electrostatic, or van der Waals interactions; however, binding may also be covalent. By "conjugated" is meant the covalent linkage of at least two molecules. In some embodiments, the composition can be an antibody-drug conjugate.

In some embodiments, an antibody, antibody reagent, or antigen-binding portion thereof can be bound to and/or conjugated to multiple chemotherapeutic molecules. In some embodiments, an antibody-drug conjugate can be bound to and/or conjugated to multiple chemotherapeutic molecules. In some embodiments, the ratio of a given chemotherapeutic molecule to an antibody or antigen-binding portion thereof can be from about 1:1 to about 1,000:1, e.g., a single antibody reagent molecule can be linked to, conjugated to, etc. from about 1 to about 1,000 individual chemotherapeutic molecules.

In some embodiments, an antibody, or antigen-binding portion thereof, and the chemotherapeutic agent can be present in a scaffold material. Scaffold materials suitable for use in therapeutic compositions are known in the art and can include, but are not limited to, a nanoparticle; a matrix; a hydrogel; and a biomaterial, biocompatible, and/or biodegradable scaffold material. As used herein, the term "nanoparticle" refers to particles that are on the order of about $10^{-9}$ or one to several billionths of a meter. The term "nanoparticle" includes nanospheres; nanorods; nanoshells; and nanoprisms; these nanoparticles may be part of a nanonetwork.

The term "nanoparticles" also encompasses liposomes and lipid particles having the size of a nanoparticle. As used herein, the term "matrix" refers to a 3-dimensional structure comprising the components of a composition described herein (e.g., an antibody or antigen-binding portion thereof). Non-limiting examples of matrix structures include foams; hydrogels; electrospun fibers; gels; fiber mats; sponges; 3-dimensional scaffolds; non-woven mats; woven materials; knit materials; fiber bundles; and fibers and other material formats. See, e.g., Rockwood et al. (2011) and U.S. Patent Publications 2011/0167602; 2011/0009960; 2012/0296352; and U.S. Pat. No. 8,172,901; each of which is incorporated by reference herein in its entirety. The structure of the matrix can be selected by one of skill in the art depending upon the intended application of the composition, e.g., electrospun matrices can have greater surface area than foams.

In some embodiments, the scaffold is a hydrogel. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel. In general, hydrogels are superabsorbent. Hydrogels have many desirable properties for biomedical applications. For example, they can be made nontoxic and compatible with tissue, and they are highly permeable to water, ions, and small molecules. Hydrogels are superabsorbent (they can contain over 99% water) and can be comprised of natural (e.g., silk) or synthetic polymers, e.g., PEG.

As used herein, "biomaterial" refers to a material that is biocompatible and biodegradable. As used herein, the term "biocompatible" refers to substances that are not toxic to cells. In some embodiments, a substance is considered to be "biocompatible" if its addition to cells in vitro results in less than or equal to approximately 20% cell death. In some embodiments, a substance is considered to be "biocompatible" if its addition to cells in vivo does not induce inflammation and/or other adverse effects in vivo. As used herein, the term "biodegradable" refers to substances that are degraded under physiological conditions. In some embodiments, a biodegradable substance is a substance that is broken down by cellular machinery. In some embodiments, a biodegradable substance is a substance that is broken down by chemical processes.

As used herein, the term "nucleic acid" or "nucleic acid sequence" refers to a polymeric molecule incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. In some embodiments, the nucleic acid can be a cDNA, e.g., a nucleic acid lacking introns.

Nucleic acid molecules encoding amino acid sequence variants of antibodies are prepared by a variety of methods known in the art. These methods include, but are not limited to preparation by oligonucleotide-mediated (or site-directed) mutagenesis, PCR mutagenesis, and cassette mutagenesis of an earlier prepared variant or a non-variant version of the antibody. A nucleic acid sequence encoding at least one antibody, portion or polypeptide as described herein can be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations can be used to construct nucleic acid sequences which encode a monoclonal antibody molecule, antibody reagent, antigen binding region thereof, or CAR.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression as peptides or antibody portions in recoverable amounts. The precise nature of the regulatory regions needed for gene expression may vary from organism to organism, as is well known in the analogous art.

In some embodiments, a nucleic acid encoding an antibody, antibody reagent, antigen-binding portion thereof, or CAR as described herein is comprised by a vector. In some of the aspects described herein, a nucleic acid sequence encoding an antibody, antibody reagent, antigen-binding portion thereof, or CAR as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g., 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding an antibody, antigen-binding portion thereof, or CAR as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In one aspect of any of the embodiments, described herein is a cell comprising an antibody, antibody reagent, antigen-binding portion thereof, or CAR as described herein, or a nucleic acid encoding such an antibody, antibody reagent, antigen-binding portion thereof, or CAR.

The expression of an antibody, antibody reagent, antigen-binding portion thereof, or CAR as described herein can occur in either prokaryotic or eukaryotic cells. Suitable hosts include bacterial or eukaryotic hosts, including yeast, insects, fungi, bird and mammalian cells either in vivo, or in situ, or host cells of mammalian, insect, bird or yeast origin. The mammalian cell or tissue can be of human, primate, hamster, rabbit, rodent, cow, pig, sheep, horse, goat, dog or cat origin, but any other mammalian cell may be used. Further, by use of, for example, the yeast ubiquitin hydrolase system, in vivo synthesis of ubiquitin-transmembrane polypeptide fusion proteins can be accomplished. The fusion proteins so produced can be processed in vivo or purified and processed in vitro, allowing synthesis of an antibody or portion thereof as described herein with a specified amino terminus sequence. Moreover, problems associated with retention of initiation codon-derived methionine residues in direct yeast (or bacterial) expression maybe avoided. Any of a series of yeast gene expression systems incorporating promoter and termination elements from the actively expressed genes coding for glycolytic enzymes produced in large quantities when yeast are grown in mediums rich in glucose can be utilized to obtain recombinant antibodies or antigen-binding portions thereof as described herein. Known glycolytic genes can also provide very efficient transcriptional control signals. For example, the promoter and terminator signals of the phosphoglycerate kinase gene can be utilized.

Production of antibodies or antigen-binding portions thereof as described herein in insects can be achieved. For example, by infecting the insect host with a baculovirus engineered to express a transmembrane polypeptide by methods known to those of ordinary skill in the art.

In some embodiments, the introduced nucleotide sequence is incorporated into a plasmid or viral vector capable of autonomous replication in the recipient host. Any of a wide variety of vectors can be employed for this purpose and are known and available to those or ordinary skill in the art. Factors of importance in selecting a particular plasmid or viral vector include: the ease with which recipient cells that contain the vector may be recognized and selected from those recipient cells which do not contain the vector; the number of copies of the vector which are desired in a particular host; and whether it is desirable to be able to "shuttle" the vector between host cells of different species.

Example prokaryotic vectors known in the art include plasmids such as those capable of replication in *E. coli*, for example. Other gene expression elements useful for the expression of cDNA encoding antibodies, antigen-binding portions thereof, or CARs include, but are not limited to (a) viral transcription promoters and their enhancer elements, such as the SV40 early promoter, Rous sarcoma virus LTR, and Moloney murine leukemia virus; (b) splice regions and polyadenylation sites such as those derived from the SV40 late region, and (c) polyadenylation sites such as in SV40. Immunoglobulin cDNA genes can be expressed, e.g., using as expression elements the SV40 early promoter and its enhancer, the mouse immunoglobulin H chain promoter enhancers, SV40 late region mRNA splicing, rabbit S-globin intervening sequence, immunoglobulin and rabbit S-globin polyadenylation sites, and SV40 polyadenylation elements.

For immunoglobulin genes comprised of part cDNA, part genomic DNA, the transcriptional promoter can be human cytomegalovirus, the promoter enhancers can be cytomegalovirus and mouse/human immunoglobulin, and mRNA splicing and polyadenylation regions can be the native chromosomal immunoglobulin sequences.

In some embodiments, for expression of cDNA genes in rodent cells, the transcriptional promoter is a viral LTR sequence, the transcriptional promoter enhancers are either or both the mouse immunoglobulin heavy chain enhancer and the viral LTR enhancer, the splice region contains an intron of greater than 31 bp, and the polyadenylation and transcription termination regions are derived from the native chromosomal sequence corresponding to the immunoglobulin chain being synthesized. In other embodiments, cDNA sequences encoding other proteins are combined with the above-recited expression elements to achieve expression of the proteins in mammalian cells.

A gene is assembled in, or inserted into, an expression vector. Recipient cells capable of expressing the chimeric immunoglobulin chain gene product are then transfected singly with an antibody, antigen-binding portion thereof, or CAR, or chimeric H or chimeric L chain-encoding gene, or are co-transfected with a chimeric H and a chimeric L chain gene. The transfected recipient cells are cultured under conditions that permit expression of the incorporated genes and the expressed immunoglobulin chains or intact antibodies or fragments are recovered from the culture.

In some embodiments, the genes encoding the antibody, antigen-binding portion thereof, CAR, or chimeric H and L chains, or portions thereof are assembled in separate expression vectors that are then used to co-transfect a recipient cell. Each vector can contain two selectable genes, a first selectable gene designed for selection in a bacterial system and a second selectable gene designed for selection in a eukaryotic system, wherein each vector has a different pair of genes. This strategy results in vectors which first direct the production, and permit amplification, of the genes in a bacterial system. The genes so produced and amplified in a bacterial host are subsequently used to co-transfect a eukaryotic cell, and allow selection of a co-transfected cell carrying the desired transfected genes. Non-limiting examples of selectable genes for use in a bacterial system are the gene that confers resistance to ampicillin and the gene that confers resistance to chloramphenicol. Selectable genes for use in eukaryotic transfectants include the xanthine guanine phosphoribosyl transferase gene (designated gpt) and the phosphotransferase gene from Tn5 (designated neo). Alternatively the genes can be assembled on the same expression vector.

For transfection of the expression vectors and production of the antibodies, antibody reagents, antigen-binding portions thereof, or CARs described herein, the recipient cell line can be a myeloma cell. Myeloma cells can synthesize, assemble and secrete immunoglobulins encoded by transfected immunoglobulin genes and possess the mechanism for glycosylation of the immunoglobulin. For example, in some embodiments, the recipient cell is the recombinant Ig-producing myeloma cell SP2/0 (ATCC #CRL 8287). SP2/0 cells produce only immunoglobulin encoded by the transfected genes. Myeloma cells can be grown in culture or in the peritoneal cavity of a mouse, where secreted immunoglobulin can be obtained from ascites fluid. Other suitable recipient cells include lymphoid cells such as B lymphocytes of human or non-human origin, hybridoma cells of human or non-human origin, or interspecies heterohybridoma cells.

An expression vector carrying a chimeric, humanized, or composite human antibody construct, antibody, antigen-binding portion thereof, and/or CAR as described herein can be introduced into an appropriate host cell by any of a variety of suitable means, including such biochemical means as transformation, transfection, conjugation, protoplast fusion, calcium phosphate-precipitation, and application with polycations such as diethylaminoethyl (DEAE) dextran, and such mechanical means as electroporation, direct microinjection, and microprojectile bombardment, as known to one of ordinary skill in the art.

Traditionally, monoclonal antibodies have been produced as native molecules in murine hybridoma lines. In addition to that technology, the methods and compositions described herein provide for recombinant DNA expression of monoclonal antibodies. This allows the production of humanized antibodies as well as a spectrum of antibody derivatives and fusion proteins in a host species of choice. The production of antibodies in bacteria, yeast, transgenic animals and chicken eggs are also alternatives for hybridoma-based production systems. The main advantages of transgenic animals are potential high yields from renewable sources.

In one aspect, a cell comprising an isolated antibody, antigen-binding portion thereof, or CAR as described herein is provided. In some embodiments, the isolated antibody, antigen-binding portion thereof, or CAR as described herein is expressed on the cell surface. In some embodiments, the cell comprises a nucleic acid encoding an isolated antibody, antigen-binding portion thereof, or CAR as described herein.

In some embodiments, the cell is an immune cell. As used herein, "immune cell" refers to a cell that plays a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes. In some embodiments, the cell is a T cell; a NK cell; a NKT cell; lymphocytes, such as B cells and T cells; and myeloid cells, such as monocytes, macrophages, eosinophils, mast cells, basophils, and granulocytes.

In particular embodiments, a cell (e.g., an immune cell) is transduced with a retroviral vector, e.g., a lentiviral vector, encoding a CAR. For example, an immune effector cell is transduced with a vector encoding a CAR that comprises an anti-CHI3L1/anti-PD-1 antibody or antigen binding portion thereof that binds a CHI3L1 and PD-1 polypeptides, with an intracellular signaling domain of CD3ζ, CD28, 4-1BB, Ox40, or any combinations thereof. Thus, these transduced cells can elicit a CAR-mediated cytotoxic response.

Retroviruses are a common tool for gene delivery. In particular embodiments, a retrovirus is used to deliver a polynucleotide encoding a chimeric antigen receptor (CAR) to a cell. As used herein, the term "retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include, but are not limited to: Moloney murine leukemia virus (M-MuLV), Moloney murine sarcoma virus (MoMSV), Harvey murine sarcoma virus (Ha-MuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred. In particular embodiments, a lentivirus is used to deliver a polynucleotide comprising a CAR to a cell.

Retroviral vectors and more particularly lentiviral vectors may be used in practicing particular embodiments of the present invention. Accordingly, the term "retrovirus" or "retroviral vector", as used herein is meant to include "lentivirus" and "lentiviral vectors" respectively.

CHI3L1 Antigen-Binding Portion

As used herein, "CHI3L1," "chintinase-3-like protein 1," or "YKL-40" refers to a ~40 kDa glycoprotein secreted by at least macrophages, chondrocytes, neutrophils, synovial cells, and some cancer cells. CHI3L1 does not have chitinase activity, is a Th2 promoting cytokine, has been linked to the AKT anti-apoptotic signaling pathway and induces the migration of astrocytes. The sequences of CHI3L1 expression products are known for a number of species, e.g., human CHI3L1 (NCBI Gene ID No: 1116) mRNA (NCBI Ref Seq: NM_001276.1 and NCBI Ref Seq: NM_001276.2) and polypeptide (NCBI Ref Seq: NP_001267.1 and NCBI Ref Seq: NP_001267.2).

In some of the embodiments, the CHI3L1 antigen-binding portion of the bispecific antibodies of the present invention include one or more of the heavy chain CDRs having the amino acid sequences of SEQ ID NOs: 1-3 and/or one or more of the light chain CDRs having the amino acid sequences of SEQ ID NOs: 4-6 disclosed in U.S. Pat. No. 10,253,111 and reproduced below in Table 1.

TABLE 1

| Sequences of variable complementarity determining regions (CDRs) of the FRG antibody | | |
| --- | --- | --- |
| Heavy Chain CDRs | | |
| CDR1 | GYTFTNYG | SEQ ID NO: 1 |
| (DNA) | (GGGTATACCTTCACAAACTATGGA) | SEQ ID NO: 7 |
| CDR2 | INTYTGEP | SEQ ID NO: 2 |
| (DNA) | (ATAAATACCTACACTGGAGAGCCA) | SEQ ID NO: 8 |
| CDR3 | ARLGYGKFYVMDY | SEQ ID NO: 3 |
| (DNA) | (GCAAGATTGGGATATGGTAAATTCT ATGTTATGGACTAC) | SEQ ID NO: 9 |
| Light Chain CDRs | | |
| CDR1 | QSLVHSNGNTY | SEQ ID NO: 4 |
| (DNA) | (CAGAGCCTTGTACACAGTAATGGAA ACACCTAT) | SEQ ID NO: 10 |
| CDR2 | KVS | SEQ ID NO: 5 |
| (DNA) | (AAAGTTTCC) | SEQ ID NO: 11 |
| CDR3 | SQSTHVTWT | SEQ ID NO: 6 |
| (DNA) | (TCTCAAAGTACACATGTTACGTGGA CG) | SEQ ID NO: 12 |

In some embodiments of any of the aspects, the bispecific antibody, antibody reagent, antigen-binding portion thereof, or CAR that specifically binds an CHI3L1 polypeptide binds specifically to an epitope selected from SEQ ID NOs: 13-24 disclosed in U.S. Pat. No. 10,253,111. In some embodiments of any of the aspects, the bispecific antibody, antibody reagent, antigen-binding portion thereof, or CAR that specifically binds a CHI3L1 polypeptide binds specifically to the epitope of SEQ ID NO: 13 disclosed in U.S. Pat. No. 10,253,111.

In some of the embodiments, the backbone of an anti-human CHI3L1 antibody comprises a conservative substitution relative to the heavy chain sequence having the amino acid sequence of SEQ ID NO: 36 or the light chain sequence having the amino acid sequence of SED ID NO: 38 disclosed in U.S. Pat. No. 10,253,111, wherein the conservative substitution is in a sequence not comprised by a CDR. In an alternative embodiment, the backbone of an anti-human CHI3L1 antibody comprises the heavy chain sequence of the FRG antibody having the amino sequence of SEQ ID NO: 36 or the light chain sequence of the FRG antibody having the amino acid sequence of SED ID NO: 38 disclosed in U.S. Pat. No. 10,253,111, both of which are provided below as SED ID NO: 13 and SED ID NO: 14, respectively.

TABLE 2

```
FRG Heavy Chain Sequence
QIQLVQSGPELKKPGETVKISCKASGYTFTNYGMNWVKQAPGKGLKW
MGWINTYTGEPTYADDFKGRFAFSLETSASTAYLQINNLRNEDMSTY
FCARLGYGKFYVMDYWGQGTSVTVSS (SEQ ID NO: 13)

FRG Light Chain Sequence
DVVMTQTPLSLPVSLGDQASISCRSSQSLVHSNGNTYLHWYLQKPGQ
SPKLLIYKVSNRFSGVPDRFSGSGSGTDFTLKISRVEAEDLGVYFCS
QSTHVTWTFGGGTKLEIK (SEQ ID NO: 14)
```

In other alternative embodiments, the CHI3L1 antigen-binding portion of the bispecific antibodies of the present invention include one or more of the heavy chain CDRs having the amino acid sequences of SEQ ID NOs: 1-12 and/or one or more of the light chain CDRs having the amino acid sequences of SEQ ID NOs: 13-20 disclosed in Table 3. See, e.g., International Published Application WO 2019060675.

TABLE 3

Heavy Chain CDRs

```
QIQLVQSGSELKKPGASVKISCKASGYTFTNYGMNWVRQAPGQGLEWMGWINTYTGEPTYADDFKGRFVFS
     LDTSVSTAYLQISSLKAEDTSVYFCARLGYGKFYVMDYWGQGTSVTVSS (SEQ ID NO: 15)

QIQLVQSGSELKKPGASVKISCKASGYTFTNYGMNWVRQAPGQGLEWMGWINTYTGEPTYAQGFTGRFVFS
     LDTSVSTAYLQISSLKAEDTSVYFCARLGYGKFYVMDYWGQGTSVTVSS (SEQ ID NO: 16)

QIQLVQSGPELKKPGASVKISCKASGYTFTNYGMNWVRQAPGQGLKWMGWINTYTGEPTYADDFTGRFVFS
     LDTSVSTAYLQISSLKAEDTSVYFCARLGYGKFYVMDYWGQGTSVTVSS (SEQ ID NO: 17)

QIQLVQSGSELKKPGASVKISCKASGYTFTNYGMNWVRQAPGQGLKWMGWINTYTGEPTYADDFKGRFVFS
     LDTSVSTAYLQISSLKAEDTSVYFCARLGYGKFYVMDYWGQGTSVTVSS (SEQ ID NO: 18)

QIQLVQSGPELKKPGASVKISCKASGYTFTNYGMNWVKQAPGQGLKWMGWINTYTGEPTYAQGFTGRFVFS
     LDTSVSTAYLQISSLKAEDTSTYFCARLGYGKFYVMDYWGQGTSVTVSS (SEQ ID NO: 19)

QIQLVQSGPELKKPGASVKISCKASGYTFTSYAMNWVKQAPGQGLKWMGWINTYTGEPTYADDFKGRFVFS
     LDTSVSTAYLQISSLKAEDTSVYFCARLGYGKFYVMDYWGQGTSVTVSS (SEQ ID NO: 20)

QIQLVQSGHEVKQPGASVKISCKASGYTFTNYGMNWVPQAPGQGLEWMGWINTYTGEPTYADDFKGRFVFS
     LDTSASTAYLQISSLKAEDMSMYFCARLGYGKFYVMDYWGQGTSVTVSS (SEQ ID NO: 21)

QIQLVQSGHEVKQPGASVKISCKASGYTFTNYGMNWVPQAPGQGLEWMGWINTYTGEPTYAQGFTGRFVFS
     LDTSASTAYLQISSLKAEDMSMYFCARLGYGKFYVMDYWGQGTSVTVSS (SEQ ID NO: 22)

QIQLVQSGHEVKQPGASVKISCKASGYTFTNYGMNWVKQAPGQGLKWMGWINTYTGEPTYADDFTGRFVFS
     LDTSASTAYLQISSLKAEDMSMYFCARLGYGKFYVMDYWGQGTSVTVSS (SEQ ID NO: 23)

QIQLVQSGPEVKQPGASVKISCKASGYTFTNYGMNWVPQAPGQGLKWMGWINTYTGEPTYADDFTGRFVFS
     LDTSASTAYLQISSLKAEDMSMYFCARLGYGKFYVMDYWGQGTSVTVSS (SEQ ID NO: 24)

QIQLVQSGPEVKQPGASVKISCKASGYTFTNYGMNWVKQAPGQGLKWMGWINTYTGEPTYAQGFTGRFVFS
     LDTSASTAYLQISSLKAEDMSTYFCARLGYGKFYVMDYWGQGTSVTVSS (SEQ ID NO: 25)

QIQLVQSGPEVKQPGASVKISCKASGYSFTTYGMNWVKQAPGQGLEWMGWINTYTGEPTYADDFKGRFVFS
     LDTSASTAYLQISSLKAEDMSTYFCARLGYGKFYVMDYWGQGTSVTVSS (SEQ ID NO: 26)
```

Light Chain CDRs

```
DVVMTQSPLSLPVTLGQPASISCRSSQSLVHSNGNTYLNWYQQRPGQSPRLLIYKVSNRFSGVPDRFSGSG
     SGTDFTLKISRVEAEDVGVYFCSQSTHVTWTFGGGTKLEIK (SEQ ID NO: 27)

DVVMTQSPLSLPVTLGQPASISCRSSQSLVHSDGNTYLHWYQQRPGQSPRLLIYKVSNRFSGVPDRFSGSG
     SGTDFTLKISRVEAEDVGVYFCSQSTHVTWTFGGGTKLEIK (SEQ ID NO: 28)

DVVMTQSPLSLPVTLGQPASISCRSSQSLVHSNGNTYLHWYQQRPGQSPRLLIYKVSNRDSGVPDRFSGSG
     SGTDFTLKISRVEAEDVGVYFCSQSTHVTWTFGGGTKLEIK (SEQ ID NO: 29)

DVVMTQSPLSLPVTLGQPASISCRSSQSLVHSNGNTYLHWFQQRPGQSPRLLIYKVSNRFSGVPDRFSGSG
     SGTDFTLKISRVEAEDVGVYFCSQSTHVTWTFGGGTKLEIK (SEQ ID NO: 30)

DIVMTQTPLSLSVTPGQPASISCKSSQSLVHSNGNTYLHWYLQKPGQSPQLLIYKVSNRFSGVPDRFSGSG
     SGTDFTLKISRVEAEDVGVYYCSQSTHVTWTFGGGTKLEIK (SEQ ID NO: 31)

DVVMTQSPLSLPVTLGQPASISCRSSQSLVHSNGNTYLHWFQQRPGQSPRRLIYKVSNRFSGVPDRFSGSG
     SGTDFTLKISRVEAEDVGVYYCSQSTHVTWTFGGGTKLEIK (SEQ ID NO: 32)

DVVMTQSPLSLPVTLGQPASISCRSSQSLVHSNGNTYLHWFLQRPGQSPRLLIYKVSNRFSGVPDRFSGSG
     SGTDFTLKISRVEAEDVGVYYCSQSTHVTWTFGGGTKLEIK (SEQ ID NO: 33)

DVVMTQSPLSLPVTLGQPASISCRSSQSLVHSNGNTYLHWYQQRPGQSPRLLIYKVSNRFSGVPDRFSGSG
     SGTDFTLKISRVEAEDVGVYYCSQSTHVTWTFGGGTKLEIK (SEQ ID NO: 34)
```

PD-1 Antigen-Binding Portion

Examples of anti-PD-1 antibodies are disclosed in U.S. Pat. No. 10,344,090 (Yuan et al.); U.S. Pat. No. 10,323,091 (van Dijk et al.); U.S. Pat. No. 10, 316,089 (Baruah et al.); U.S. Pat. No. 10,280,224 (Wang et al.); U.S. Pat. No. 10,239,942 (Amirina et al.); U.S. Pat. No. 10,221,244 (Wong et al.); U.S. Pat. No. 10,155,037 (Abdiche et al.); and in U.S. Published Application Nos. 2011/0123550 (Shibayama et al.); 2016/0376367 (Yuan et al.); 2017/0210806 (Liu).

The antigen-binding portion of any anti-PD-1 antibodies can be used in the bispecific antibodies of the present invention. In some embodiments, bispecific antibodies that detects and neutralizes CHI3L1 and PD1 comprise a PD-1 single chain variable fragment (scFv-PD1) and linkers (shown in bold, underline) are provided in Table 4.

TABLE 4

| Linker | Variable HC |
|---|---|
| VEGGSGGSGGSGGSGGVDQVQLVQSGAEVKKPGASVKVSCKASGY | |
| TFTNYYMYWVRQAPGQGLEWMGGINPSNGGTNFNEKFKNRVTLTT | |
| DSSTTTAYMELKSLQFDDTAVYYCARRDYRFDMGFDYWGQGTLVT | |
| Linker | Variable LC |
| VSSGGGGSGGGGSGGGGSGGGGSEIVLTQSPGTLSLSPGERATLS | |
| CRASKGVSTSGYSYLHWYQQKPGQAPRLLIYLASYLESGVPDRFS | |
| GSGSGTDFTLTISRLEPEDFAVYYCQHSRDLPLTFGGGTKVEIK | |

(SEQ ID NO: 35)

Pharmaceutical Compositions

In one aspect of any of the embodiments, described herein is a composition comprising a bispecific antibody, antibody reagent, antigen-binding portion thereof, or CAR as described herein or a nucleic acid encoding an antibody, antibody reagent, antigen-binding portion thereof, or CAR as described herein or a cell as described herein. In some embodiments, the composition is a pharmaceutical composition. As used herein, the term "pharmaceutical composition" refers to the active agent in combination with a pharmaceutically acceptable carrier accepted for use in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance or maintain the effectiveness of the active ingredient. The therapeutic composition as described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Examples of such additional liquid phases are glycerin, vegetable oils such as cottonseed oil, and water-oil emulsions. The amount of an active agent used in the invention that will be effective in the treatment of a particular disorder or condition will depend on the nature of the disorder or condition, and can be determined by standard clinical techniques.

In some embodiments, the composition comprising an antibody, antibody reagent, antigen-binding portion thereof, or CAR as described herein or a nucleic acid encoding an antibody, antibody reagent, antigen-binding portion thereof, or CAR as described herein can be a lyophilisate.

In some embodiments, the technology described herein relates to a syringe or catheter, including an organ-specific catheter (e.g., renal catheter, biliary catheter, cardiac catheter, etc.), comprising a therapeutically effective amount of a composition described herein.

In one aspect, described herein is a method of inhibiting or killing a CHI3L1+/PD-1+ cell, the method comprising contacting the cell with an isolated bispecific antibody, antibody reagent, antigen-binding portion thereof, or CAR as described herein, a nucleic acid encoding such polypeptides, a cell comprising such a polypeptide or nucleic acid, or a composition comprising such a polypeptide or nucleic acid. Inhibiting a CHI3L1+/PD-1+ cell can comprise inhibiting the metabolic activity, metastasis, and/or proliferation of the cell. Assays for measuring metabolic activity, metastasis (e.g., migration assays) and proliferation are well known in the art. Similarly, assays for measuring killing of CHI3L1+/PD-1+ cells, e.g., cell viability assays are well known in the art.

As used herein, a "CHI3L1+/PD-1+" cell is a cell expressing an increased level of CHI3L1+ and PD-1+, e.g., as compared to a healthy cell of the same type or an average level of CHI3L1+/PD-1+ found in healthy cells of the same type.

In some embodiments of any of the aspects described herein, a subject administered a composition described herein can be a subject determined to have an elevated level of CHI3L1 or a level of CHI3L1 that is increased compared to a prior assessment of the level in that subject. In some embodiments of any of the aspects, the elevated level of CHI3L1 is the level of circulating CHI3L1. In some embodiments of any of the aspects described herein, a subject administered a composition described herein can be a subject determined to have cancer cells which are CHI3L1+.

In some embodiments of any of the aspects described herein, the method comprising administering a composition as described herein can further comprise a first step of identifying a subject having an elevated level of CHI3L1. In some embodiments of any of the aspects, the elevated level of CHI3L1 is the level of circulating CHI3L1. In some embodiments of any of the aspects described herein, the method comprising administering a composition as described herein can further comprise a first step of identifying a subject having cancer cells which are CHI3L1+.

As used herein, a "CHI3L1+" cell is a cell expressing an increased level of CHI3L1+, e.g., as compared to a healthy cell of the same type or an average level of CHI3L1 found in healthy cells of the same type. In some embodiments of any of the aspects, an increased level of CHI3L1 can be a level which is at least 1.5× the level found in a reference, e.g., 1.5×, 2×, 3×, 4×, 5× or greater than the reference level.

In one aspect, the technology described herein relates to a method comprising administering an antibody, antibody reagent, antigen-binding portion thereof, or CAR as described herein or a nucleic acid encoding an antibody, antibody reagent, antigen-binding portion thereof, or CAR as described herein to a subject. In some embodiments, the subject is in need of treatment for a cancer and/or malignancy. In some embodiments, the subject is in need of treatment for: prostate cancer, colon cancer, rectal cancer, ovarian cancer, kidney cancer, breast cancer, glioblastoma, melanoma, malignant melanoma, and lung cancer. In some embodiments, the method is a method of treating a subject. In some embodiments, the method is a method of treating a cancer in a subject.

In one aspect, the technology described herein relates to a method comprising administering a bispecific antibody, antibody reagent, antigen-binding portion thereof, or CAR as described herein or a nucleic acid encoding a bispecific antibody, antibody reagent, antigen-binding portion thereof, or CAR as described herein to a subject.

In one aspect, described herein is a method of treating cancer in a subject in need thereof, the method comprising administering a cell as described herein, e.g., a cell comprising a bispecific antibody, antibody reagent, antigen-binding portion thereof, or CAR as described herein. In some embodiments, the cell is an immune cell.

In one aspect, described herein is a method of treating cancer in a subject in need thereof, the method comprising administering a nucleic acid as described herein or an immune cell comprising the nucleic acid to the subject, wherein the subject's immune cells are caused to express the polypeptide encoded by the nucleic acid. In some embodiments, the immune cell is a T cell. Nucleic acids can be targeted to particular cell types by, e.g., use of a cell-type specific promoter and/or a composition that selectively binds to the desired cell type. For example, conjugation of a nucleic acid to an aptamer can permit targeted delivery. See, e.g., McNamara, et al. (2006). In an alternative embodiment, the nucleic acid can be delivered using drug delivery systems such as a nanoparticle, a dendrimer, a polymer, liposomes, or a cationic delivery system. Positively charged cationic delivery systems facilitate binding of a nucleic acid molecule (negatively charged) and also enhance interactions at the negatively charged cell membrane to permit efficient uptake of a nucleic acid by the cell. Cationic lipids, dendrimers, or polymers, can either be bound to a nucleic acid, or induced to form a vesicle or micelle (see, e.g., Kim, et al.

(2008)) that encases a nucleic acid. The formation of vesicles or micelles further prevents degradation of the nucleic acid when administered systemically. Methods for making and administering cationic-inhibitory nucleic acid complexes are well within the abilities of one skilled in the art. Some non-limiting examples of drug delivery systems useful for systemic delivery of nucleic acids include DOTAP Oligofectamine, "solid nucleic acid lipid particles", cardiolipin, polyethyleneimine, Arg-Gly-Asp (RGD) peptides, and polyamidoamines. In some embodiments, a nucleic acid forms a complex with cyclodextrin for systemic administration. Methods for administration and pharmaceutical compositions of nucleic acids and cyclodextrins can be found in U.S. Pat. No. 7,427,605, which is herein incorporated by reference in its entirety. Targeted delivery of nucleic acids is described, for example in Ikeda and Taira (2006); Soutschek et al. (2004); and Lorenze et al. (2004); each of which is incorporated by reference herein in its entirety. By way of example, the nucleic acid can be targeted to immune cells by encapsulating the inhibitor in a liposome comprising ligands of receptors expressed on immune cells, e.g., TCRs. In some embodiments, the liposome can comprise aptamers specific for immune cells.

In some embodiments, the methods described herein relate to CAR-T cell therapy. CAR-T cell and related therapies relate to adoptive cell transfer of immune cells (e.g., T cells) expressing a CAR that binds specifically to a targeted cell type (e.g., cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express the CAR. Further discussion of CAR-T therapies can be found, e.g., in Maus et al. (2014); Reardon et al. Neuro-Oncology 2014 16:1441-1458; Hoyos et al. (2012); Byrd et al. (2014); Maher and Wilkie (2009); and Tamada et al. Clin Cancer Res 2012 18:6436-6445; each of which is incorporated by reference herein in its entirety.

It can generally be stated that a pharmaceutical composition comprising the cells, e.g., T cells or immune cells, described herein may be administered at a dosage of $10^2$ to $10^{10}$ cells/kg body weight, preferably $10^5$ to $10^6$ cells/kg body weight, including all integer values within those ranges. The number of cells will depend upon the ultimate use for which the composition is intended as will the type of cells included therein. For uses provided herein, the cells are generally in a volume of a liter or less, can be 500 mL or less, even 250 mL or 100 mL or less. Hence the density of the desired cells is typically greater than $10^6$ cells/mL and generally is greater than $10^7$ cells/mL, generally $10^8$ cells/mL or greater. The clinically relevant number of immune cells can be apportioned into multiple infusions that cumulatively equal or exceed $10^5$, $10^6$, $10^7$, $10^8$, $10^9$, $10^{10}$, $10^{11}$, or $10^{12}$ cells. In some aspects of the present invention, particularly since all the infused cells will be redirected to a particular target antigen, lower numbers of cells, in the range of $10^6$/kilogram ($10^6$-$10^{11}$ per patient) may be administered. CAR expressing cell compositions may be administered multiple times at dosages within these ranges. The cells may be allogeneic, syngeneic, xenogeneic, or autologous to the patient undergoing therapy. If desired, the treatment may also include administration of mitogens (e.g., PHA) or lymphokines, cytokines, and/or chemokines (e.g., IFN-γ, IL-2, IL-12, TNF-alpha, IL-18, and TNF-beta, GM-CSF, IL-4, IL-13, Flt3-L, RANTES, MIP1a, etc.) as described herein to enhance induction of the immune response. In some embodiments, the dosage can be from about $1 \times 10^5$ cells to about $1 \times 10^8$ cells per kg of body weight. In some embodiments, the dosage can be from about $1 \times 10^6$ cells to about $1 \times 10^7$ cells per kg of body weight. In some embodiments, the dosage can be about $1 \times 10^6$ cells per kg of body weight. In some embodiments, one dose of cells can be administered. In some embodiments, the dose of cells can be repeated, e.g., once, twice, or more. In some embodiments, the dose of cells can be administered on, e.g., a daily, weekly, or monthly basis.

The dosage ranges for the agent depend upon the potency, and encompass amounts large enough to produce the desired effect e.g., slowing of tumor growth or a reduction in tumor size. The dosage should not be so large as to cause unacceptable adverse side effects. Generally, the dosage will vary with the age, condition, and sex of the patient and can be determined by one of skill in the art. The dosage can also be adjusted by the individual physician in the event of any complication. In some embodiments, the dosage ranges from 0.001 mg/kg body weight to 0.5 mg/kg body weight. In some embodiments, the dose range is from 5 μg/kg body weight to 100 μg/kg body weight. Alternatively, the dose range can be titrated to maintain serum levels between 1 μg/mL and 1000 μg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

Administration of the doses recited above can be repeated. In some embodiments, the doses are given once a day, or multiple times a day, for example but not limited to three times a day. In some embodiments, the doses recited above are administered daily for several weeks or months. The duration of treatment depends upon the subject's clinical progress and responsiveness to therapy.

In some embodiments, the dose can be from about 2 mg/kg to about 15 mg/kg. In some embodiments, the dose can be about 2 mg/kg. In some embodiments, the dose can be about 4 mg/kg. In some embodiments, the dose can be about 5 mg/kg. In some embodiments, the dose can be about 6 mg/kg. In some embodiments, the dose can be about 8 mg/kg. In some embodiments, the dose can be about 10 mg/kg. In some embodiments, the dose can be about 15 mg/kg. In some embodiments, the dose can be from about 100 mg/m² to about 700 mg/m². In some embodiments, the dose can be about 250 mg/m². In some embodiments, the dose can be about 375 mg/m². In some embodiments, the dose can be about 400 mg/m². In some embodiments, the dose can be about 500 mg/m².

In some embodiments, the dose can be administered intravenously. In some embodiments, the intravenous administration can be an infusion occurring over a period of from about 10 minute to about 3 hours. In some embodiments, the intravenous administration can be an infusion occurring over a period of from about 30 minutes to about 90 minutes.

In some embodiments the dose can be administered about weekly. In some embodiments, the dose can be administered weekly. In some embodiments, the dose can be administered weekly for from about 12 weeks to about 18 weeks. In some embodiments, the dose can be administered about every two weeks. In some embodiments the dose can be administered about every three weeks. In some embodiments, the dose can be from about 2 mg/kg to about 15 mg/kg administered about every two weeks. In some embodiments, the dose can be from about 2 mg/kg to about 15 mg/kg administered about every three weeks. In some embodiments, the dose can be from about 2 mg/kg to about 15 mg/kg administered intravenously about every two weeks. In some embodiments, the dose can be from about 2 mg/kg to about 15 mg/kg administered intravenously about every three weeks. In some embodiments, the dose can be from about 200 mg/m² to about 400 mg/m² administered intravenously about every week. In some embodiments, the dose can be from about 200 mg/m² to about 400 mg/m² administered intravenously about every two weeks. In some embodiments, the dose can be from about 200 mg/m² to about 400 mg/m² administered intravenously about every three weeks. In some embodiments, a total of from about 2 to about 10 doses are administered. In some embodiments, a total of four doses are administered. In some embodiments, a total of five doses are administered. In some embodiments, a total of six doses are administered. In some embodiments, a total of seven doses are administered. In some embodiments, a total of eight doses are administered. In some embodiments, the administration occurs for a total of from about four weeks to about 12 weeks. In some embodiments, the administration occurs for a total of about six weeks. In some embodiments, the administration occurs for a total of about eight weeks. In some embodiments, the administration occurs for a total of about 12 weeks. In some embodiments, the initial dose can be from about 1.5 to about 2.5 fold greater than subsequent doses.

In some embodiments, the dose can be from about 1 mg to about 2000 mg. In some embodiments, the dose can be about 3 mg. In some embodiments, the dose can be about 10 mg. In some embodiments, the dose can be about 30 mg. In some embodiments, the dose can be about 1000 mg. In some embodiments, the dose can be about 2000 mg. In some embodiments, the dose can be about 3 mg given by intravenous infusion daily. In some embodiments, the dose can be about 10 mg given by intravenous infusion daily. In some embodiments, the dose can be about 30 mg given by intravenous infusion three times per week.

A therapeutically effective amount is an amount of an agent that is sufficient to produce a statistically significant, measurable change in tumor size, tumor growth etc. (efficacy measurements are described below herein). Such effective amounts can be gauged in clinical trials as well as animal studies.

An agent can be administered intravenously by injection or by gradual infusion over time. Given an appropriate formulation for a given route, for example, agents useful in the methods and compositions described herein can be administered intravenously, intranasally, by inhalation, intraperitoneally, intramuscularly, subcutaneously, intracavity, and can be delivered by peristaltic means, if desired, or by other means known by those skilled in the art. It is preferred that the compounds used herein are administered orally, intravenously or intramuscularly to a patient having cancer. Local administration directly to a tumor mass is also specifically contemplated.

Therapeutic compositions containing at least one agent can be conventionally administered in a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

In some embodiments, the methods further comprise administering the pharmaceutical composition described herein along with one or more additional chemotherapeutic agents, biologics, drugs, or treatments as part of a combinatorial therapy. In some such embodiments, the chemotherapeutic agent biologic, drug, or treatment is selected from the group consisting of: radiation therapy, surgery, antibody reagents, and/or small molecules.

In some embodiments of the methods described herein, the methods further comprise administering one or more chemotherapeutic agents to the subject being administered the pharmaceutical composition described herein. Non-limiting examples of chemotherapeutic agents can include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall; dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb®); inhibitors of PKC-alpha, Raf, H-Ras, EGFR (e.g., erlotinib)(Tarceva®)) and VEGF-A that reduce cell proliferation and pharmaceutically acceptable salts, acids or derivatives of any one of the above.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins, such as small molecule toxins or enzymatically active toxins of bacterial, fungal, plant or animal origin, including fragments and/or variants thereof.

As used herein, the terms "chemotherapy" or "chemotherapeutic agent" refer to any chemical agent with therapeutic usefulness in the treatment of diseases characterized by abnormal cell growth. Such diseases include tumors, neoplasms and cancer as well as diseases characterized by hyperplastic growth. Chemotherapeutic agents as used herein encompass both chemical and biological agents. These agents function to inhibit a cellular activity upon which the cancer cell depends for continued survival. Categories of chemotherapeutic agents include alkylating/alkaloid agents, antimetabolites, hormones or hormone analogs, and miscellaneous antineoplastic drugs. Most, if not all of these agents are directly toxic to cancer cells and do not require immune stimulation. In one embodiment, a chemotherapeutic agent is an agent of use in treating neoplasms such as solid tumors. In one embodiment, a chemotherapeutic agent is a radioactive molecule. One of skill in the art can readily identify a chemotherapeutic agent of use (e.g., Chapter 86 in HARRISON'S PRINCIPLES OF INTERNAL MEDICINE, $14^{th}$ edition (2001); Chapter 17 in ABELOFF'S CLINICAL ONCOLOGY, $2^{nd}$ edition (2000). The bispecific and multispecific polypeptide agents described herein can be used in conjunction with additional chemotherapeutic agents.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

In some embodiments, the methods described herein can further comprise administering an additional immunotherapy to the subject. As used herein, "immunotherapy" refers to a diverse set of therapeutic strategies designed to induce the patient's own immune system to fight the tumor, and include, but are not limited to, intravesical BCG immunotherapy for superficial bladder cancer, vaccines to generate specific immune responses, such as for malignant melanoma and renal cell carcinoma, the use of Sipuleucel-T for prostate cancer, in which dendritic cells from the patient are loaded with prostatic acid phosphatase peptides to induce a specific immune response against prostate-derived cells, administration of cytokines, growth factors and/or signaling molecules that stimulate one or more immune cell type (e.g., interleukins), ex vivo expansion and/or stimulation of lymphocytes and/or dendritic cell specific for a tumor antigen prior to reintroduction to the patient, imiquimod, adoptive cell transfer, and/or the methods described, e.g., in International Publication WO 2003/063792 and U.S. Pat. No. 8,329,660. In some embodiments, the immunotherapy stimulates NK responses. In other embodiments, the immunotherapy is an adoptive cell transfer approach, i.e., adoptive immunotherapy.

In some embodiments, the methods described herein can further comprise administering an additional antibody, antibody reagent, antigen-binding portion thereof, or T cell comprising a CAR to the subject. In some embodiments, the methods described herein can further comprise administering cytokine to the subject. Antibody- and cytokine-based therapies are known in the art and can include, by way of non-limiting example, alemtuzumab; bevacizumab; brentuximab vedotin; cetuximab; gemtuzumab; ibritumomab tiuxetan; ipilimumab; ofatumumab; pantibumumab; rituximab; tositumomab; trastuzumab; interleukin-2, and interferon-alpha.

The efficacy of a given treatment for, e.g., cancer, can be determined by the skilled clinician. However, a treatment is considered "effective treatment," as the term is used herein, if any one or all of the signs or symptoms of e.g., a tumor are altered in a beneficial manner or other clinically accepted symptoms are improved, or even ameliorated, e.g., by at least 10% following treatment with an agent as described herein. Efficacy can also be measured by a failure of an individual to worsen as assessed by hospitalization or need for medical interventions (i.e., progression of the disease is halted). Methods of measuring these indicators are known to those of skill in the art and/or described herein.

An effective amount for the treatment of a disease means that amount which, when administered to a mammal in need thereof, is sufficient to result in effective treatment as that term is defined herein, for that disease. Efficacy of an agent can be determined by assessing physical indicators of, for example cancer, e.g., tumor size, tumor mass, tumor density, angiogenesis, tumor growth rate, etc.

CHI3L1 and PD-1 Levels in Subjects

In one aspect, described herein is a method of detecting, prognosing, and/or diagnosing cancer, the method comprising detecting or measuring the level of CHI3L1 and/or PD-1 or PD-L1 in a sample obtained from a subject by contacting the sample with a bispecific antibody, antibody reagent or antigen-binding portion thereof as described herein, wherein an increase in CHI3L1 and PD-1 or PD-L1 levels relative to a reference level indicates the subject has cancer, is at increased risk of developing cancer.

Recent reports have indicated that the sensitivity of PD-L1 expression as biomarker for immune checkpoint inhibitors (ICIs) such as PD-1 in patients with cancer is modest and successful therapeutic outcomes are observed in patients with low or no PD-L1 expression levels (Paz-Ares, et al., 2018; Hellmann, et al., 2019; Schoenfeld, et al., 2020). Accordingly, in an alternative aspect, method of detecting, prognosing, and/or diagnosing cancer, the method comprising detecting or measuring the level of CHI3L1 in a sample obtained from a subject by contacting the sample with a bispecific antibody, antibody reagent or antigen-binding portion thereof as described herein, wherein an increase in CHI3L1 levels relative to a reference level indicates the subject has cancer, is at increased risk of developing cancer.

In some embodiments of any of the aspects described herein, a subject administered a composition described herein can be a subject determined to have elevated levels of CHI3L1 and/or PD-1 or PD-L1. In some embodiments, the elevated levels of CHI3L1 and PD-1 or PD-L1 are the level of circulating CHI3L1 and PD-1 or PD-L1. In some embodiments of any of the aspects described herein, a subject administered a composition described herein can be a subject determined to have cancer cells which are CHI3L1+/PD-1+.

In some embodiments of any of the aspects described herein, the method comprising administering a composition as described herein can further comprise a first step of identifying a subject having elevated levels of CHI3L1 and/or PD-1 or PD-L1. In some embodiments, the elevated levels of CHI3L1 and/or PD-1 or PD-L1 are the levels of circulating CHI3L1 and/or PD-1 or PD-L1. In some embodiments of any of the aspects described herein, the method comprising administering a composition as described herein can further comprise a first step of identifying a subject having cancer cells which are CHI3L1+/PD-1+ or CHI3L1+/PD-L1+.

In one aspect, described herein is an assay comprising contacting a test sample obtained from the subject with an antibody, antibody reagent, or antigen-binding portion thereof as described herein, and detecting the presence or intensity of a signal which indicates the presence or level of CHI3L1 and PD-1 in the sample; wherein an increase in CHI3L1 and PD-1 levels relative to a reference levels indicates the subject has a higher risk of having or developing cancer.

In one aspect, described herein is a method of identifying a subject in need of treatment for cancer, the method comprising: contacting a test sample obtained from the subject with a bispecific antibody, antibody reagent, or antigen-binding portion thereof as described herein, detecting the presence or intensity of a signal which indicates the presence or level of CHI3L1 and/or PD-1 or PD-L1 in the sample; and identifying the subject as being in need of treatment for cancer when the expression level CHI3L1 and/or PD-1 or PD-L1 is increased relative to a reference level.

In one aspect, described herein is a method of determining if a subject is likely to respond to treatment with anti-CHI3L1/anti-PD-1 therapy, e.g., an anti-CHI3L1/anti-PD-1 bispecific antibody, antibody reagent, or antigen binding portion thereof, or T cell comprising a bispecific CAR that binds CHI3L1 and PD-1 or PD-L1, the method comprising: contacting a test sample obtained from the subject with an antibody, antibody reagent, or antigen-binding portion thereof as described herein, detecting the presence or intensity of a signal which indicates the presence or level of CHI3L1 and PD-1 or PD-L1 in the sample; determining that the subject is likely to respond to treatment with anti-CHI3L1/anti-PD-1 therapy when the levels of CHI3L1 and PD-1 or PD-L1 are increased relative to a reference level; and determining that the subject is not likely to respond to treatment with anti-CHI3L1/anti-PD-1 when the levels of CHI3L1 and PD-1 or PD-L1 are not increased relative to a reference level.

In one aspect, described herein is a method of treatment for cancer comprising; contacting a test sample obtained from the subject with an antibody, antibody reagent, or antigen-binding portion thereof as described herein; detecting the presence or intensity of a signal which indicates the presence or level of CHI3L1 and PD-1 in the sample; and treating the subject with an anti-CHI3L1/anti-PD-1 bispecific antibody therapy when the levels of CHI3L1 and PD-1 are increased relative to a reference level. In one aspect, described herein is a method of treating cancer comprising; administering a therapeutically effective amount of an anti-CHI3L1/anti-PD-1 bispecific antibody therapy to a subject determined to be in need of treatment for cancer and further determined to have levels of CHI3L1 and PD-1 that are increased relative to a reference level, wherein the anti-CHI3L1/anti-PD-1 therapy comprises an antibody, antibody reagent, antigen-binding portion thereof, or T cell comprising a bispecific CAR that recognizes CHI3L1 and PD-1; nucleic acid; cell; or composition as described herein.

In some embodiments, the expression level of CHI3L1 can be measured by determining the level of an expression product of the CHI3L1 gene, e.g., a CHI3L1 RNA transcript or a CHI3L1 polypeptide and the expression level of PD-1 can be measured by determining the level of an expression product of the PD-1 gene, e.g., a PD-1 RNA transcript or a PD-1 polypeptide. Such molecules can be isolated, derived, or amplified from a biological sample, such as a biofluid. In some embodiments, a detectable signal is generated by the antibody or antigen-binding portion thereof when a CHI3L1 molecule or a PD-1 molecule is present. In some embodiments, the antibody or antigen-binding portion thereof is detectably labeled or capable of generating a detectable signal. In some embodiments, the level of the CHI3L1 or PD-1 is determined using a method selected from the group consisting of: Western blot; immunoprecipitation; enzyme-linked immunosorbent assay (ELISA); radioimmunological assay (RIA); sandwich assay; fluorescence in situ hybridization (FISH); immunohistological staining; radioimmunometric assay; immunofluorescence assay; mass spectroscopy; FACS; and immunoelectrophoresis assay. In some embodiments, the antibody or antigen-binding portion thereof is detectably labeled or generates a detectable signal. In some embodiments, the expression level of CHI3L1 or PD-1 is normalized relative to the expression level of one or more reference genes or reference proteins. In some embodiments, the reference level of CHI3L1 or PD-1 is the expression level of CHI3L1 or PD-1 in a prior sample obtained from the subject.

In some embodiments, the level of CHI3L1 or PD-1 can be the level of CHI3L1 or PD-1 polypeptide. Detection of CHI3L1 or PD-1 polypeptides can be according to any method known in the art. Immunological methods to detect CHI3L1 or PD-1 polypeptides in accordance with the present technology include, but are not limited to, antibody techniques such as immunohistochemistry, immunocytochemistry, flow cytometry, fluorescence-activated cell sorting (FACS), immunoblotting, radioimmunoassays, western blotting, immunoprecipitation, enzyme-linked immunosorbant assays (ELISA), and derivative techniques that make use of antibody reagents as described herein.

Immunochemical methods require the use of an antibody reagent specific for the target molecule (e.g., the antigen or in the embodiments described herein, a CHI3L1 or PD-1 polypeptide. In some embodiments, the assays, methods, and/or systems described herein can comprise: an anti-CHI3L1 or an anti-PD-1 antibody reagent. In some embodiments, the antibody reagent can be detectably labeled. In some embodiments, the antibody reagent can be attached to a solid support (e.g., bound to a solid support). In some embodiments, the solid support can comprise a particle (including, but not limited to an agarose or latex bead or particle or a magnetic particle), a bead, a nanoparticle, a polymer, a substrate, a slide, a coverslip, a plate, a dish, a well, a membrane, and/or a grating. The solid support can include many different materials including, but not limited to, polymers, plastics, resins, polysaccharides, silicon or silica based materials, carbon, metals, inorganic glasses, and membranes.

In one embodiment, an assay, method, and/or system as described herein can comprise an ELISA. In an exemplary embodiment, a first antibody reagent can be immobilized on a solid support (usually a polystyrene micro titer plate). The solid support can be contacted with a sample obtained from a subject, and the antibody reagent will bind ("capture") antigens for which it is specific (e.g., CHI3L1 or PD-1). The solid support can then be contacted with a second labeled antibody reagent (e.g., a detection antibody reagent). The detection antibody reagent can, e.g., comprise a detectable signal, be covalently linked to an enzyme, or can itself be detected by a secondary antibody which is linked to an enzyme through bio-conjugation. The presence of a signal indicates that both the first antibody reagent immobilized on the support and the second "detection" antibody reagent have bound to an antigen, i.e., the presence of a signal indicated the presence of a CHI3L1 or PD-1 molecule. Between each step the plate is typically washed with a mild detergent solution to remove any proteins or antibodies that are not specifically bound. After the final wash step the plate is developed by adding an enzymatic substrate to produce a visible signal, which indicates the quantity of CHI3L1 or PD-1 polypeptides in the sample. Older ELISAs utilize chromogenic substrates, though newer assays employ fluorogenic substrates with much higher sensitivity. There are other different forms of ELISA, which are well known to those skilled in the art.

In one embodiment, the assays, systems, and methods described herein can comprise a lateral flow immunoassay test (LFIA), also known as the immunochromatographic assay, or strip test to measure or determine the level of CHI3L1 or PD-1 polypeptide in a sample. LFIAs are a simple device intended to detect the presence (or absence) of CHI3L1 or PD-1 in a sample. There are currently many LFIA tests used for medical diagnostics either for home testing, point of care testing, or laboratory use. LFIA tests are a form of immunoassay in which the test sample flows along a solid substrate via capillary action. After the sample is applied to the test strip it encounters a colored antibody reagent which mixes with the sample, and if bound to a portion of the sample, transits the substrate encountering lines or zones which have been pretreated with a second antibody reagent. Depending upon the level of CHI3L1 or PD-1 present in the sample the colored antibody reagent can become bound at the test line or zone. LFIAs are essentially immunoassays adapted to operate along a single axis to suit the test strip format or a dipstick format. Strip tests are extremely versatile and can be easily modified by one skilled in the art for detecting an enormous range of antigens from fluid samples such as urine, blood, water samples etc. Strip tests are also known as dip stick test, the name bearing from the literal action of "dipping" the test strip into a fluid sample to be tested. LFIA strip test are easy to use, require minimum training and can easily be included as components of point-of-care test (POCT) diagnostics to be used on site in the field. LFIA tests can be operated as either competitive or sandwich assays. Sandwich LFIAs are similar to sandwich ELISA. The sample first encounters colored particles which are labeled with antibody reagents specific for a target (e.g., a CHI3L1- or PD-1-specific antibody reagent). The test line will also contain antibody reagents (e.g., a CHI3L1- or PD-1-specific antibody reagent). The test line will show as a colored band in positive samples. In some embodiments, the lateral flow immunoassay can be a double antibody sandwich assay, a competitive assay, a quantitative assay or variations thereof. There are a number of variations on lateral flow technology. It is also possible to apply multiple capture zones to create a multiplex test.

A typical test strip consists of the following components: (1) sample application area comprising an absorbent pad (i.e., the matrix or material) onto which the test sample is applied; (2) conjugate or reagent pad—this contains antibody reagent(s) specific to the target which can be conjugated to colored particles (usually colloidal gold particles, or latex microspheres); (3) test results area comprising a reaction membrane—typically a hydrophobic nitrocellulose or cellulose acetate membrane onto which antibody reagents are immobilized in a line across the membrane as a capture zone or test line (a control zone may also be present, containing antibodies specific for the antibody reagents conjugated to the particles or microspheres); and (4) optional wick or waste reservoir—a further absorbent pad designed to draw the sample across the reaction membrane by capillary action and collect it. The components of the strip are usually fixed to an inert backing material and may be presented in a simple dipstick format or within a plastic casing with a sample port and reaction window showing the capture and control zones. While not strictly necessary, most tests will incorporate a second line which contains an antibody that picks up free latex/gold in order to confirm the test has operated correctly.

The use of "dip sticks" or LFIA test strips and other solid supports has been described in the art in the context of an immunoassay for a number of antigen biomarkers. U.S. Pat. Nos. 4,943,522; 6,485,982; 6,187,598; 5,770,460; 5,622, 871; 6,565,808, U.S. patent application Ser. Nos. 10/278, 676; 09/579,673 and 10/717,082, which are incorporated herein by reference in their entirety, are non-limiting examples of such lateral flow test devices. Three U.S. patents (U.S. Pat. No. 4,444,880, issued to H. Tom; U.S. Pat. No. 4,305,924, issued to R. N. Piasio; and U.S. Pat. No.

4,135,884, issued to J. T. Shen) describe the use of "dip stick" technology to detect soluble antigens via immunochemical assays. The apparatuses and methods of these three patents broadly describe a first component fixed to a solid surface on a "dip stick" which is exposed to a solution containing a soluble antigen that binds to the component fixed upon the "dip stick," prior to detection of the component-antigen complex upon the stick. It is within the skill of one in the art to modify the teaching of these "dip stick" technologies as necessary for the detection of CHI3L1 or PD-1 polypeptides. In some embodiments, the dip stick (or LFIA) can be suitable for use with urine samples. In some embodiments, a dip stick can be suitable for use with blood samples.

Immunochemistry is a family of techniques based on the use of a specific antibody, wherein antibodies are used to specifically target molecules inside or on the surface of cells. In some embodiments, immunohistochemistry ("IHC") and immunocytochemistry ("ICC") techniques can be used to detect or measure the levels of CHI3L1 or PD-1 polypeptide. IHC is the application of immunochemistry to tissue sections, whereas ICC is the application of immunochemistry to cells or tissue imprints after they have undergone specific cytological preparations such as, for example, liquid-based preparations. In some instances, signal amplification may be integrated into the particular protocol, wherein a secondary antibody, that includes a label, follows the application of an antibody reagent specific for platelets or leukocytes. Typically, for immunohistochemistry, tissue obtained from a subject and fixed by a suitable fixing agent such as alcohol, acetone, and paraformaldehyde, is sectioned and reacted with an antibody. Conventional methods for immunohistochemistry are described in Buchwalow and Bocker (Eds) "Immunohistochemistry: Basics and Methods" Springer (2010): Lin and Prichard "Handbook of Practical Immunohistochemistry" Springer (2011); which are incorporated by reference herein in their entireties. In some embodiments, immunocytochemistry may be utilized where, in general, tissue or cells obtained from a subject are fixed by a suitable fixing agent such as alcohol, acetone, and paraformaldehyde, to which is reacted an antibody. Methods of immunocytological staining of human samples is known to those of skill in the art and described, for example, in IMMUNOCYTOCHEMISTRY: A PRACTICAL GUIDE FOR BIOMEDICAL RESEARCH" (2009); which is incorporated by reference herein in its entirety.

In some embodiments, one or more of the antibody reagents described herein can comprise a detectable label and/or comprise the ability to generate a detectable signal (e.g., by catalyzing a reaction converting a compound to a detectable product). Detectable labels can comprise, for example, a light-absorbing dye, a fluorescent dye, or a radioactive label. Detectable labels, methods of detecting them, and methods of incorporating them into an antibody reagent are well known in the art.

In some embodiments, detectable labels can include labels that can be detected by spectroscopic, photochemical, biochemical, immunochemical, electromagnetic, radiochemical, or chemical means, such as fluorescence, chemifluoresence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or non-covalent means to the antibody reagent. Alternatively, a detectable label can be linked such as by directly labeling a molecule that achieves binding to the antibody reagent via a ligand-receptor binding pair arrangement or other such specific recognition molecules. Detectable labels can include, but are not limited to radio-isotopes, bioluminescent compounds, chromophores, anti-bodies, chemiluminescent compounds, fluorescent com-pounds, metal chelates, and enzymes.

In other embodiments, the detection antibody is labeled with a fluorescent compound. When the fluorescently labeled antibody is exposed to light of the proper wave-length, its presence can then be detected due to fluorescence. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodimine isothiocynate (TRITC)), biotin, phycoeryth-rin, AMCA, CyDyes™, 6-carboxyfhiorescein (commonly known by the abbreviations FAM and F), 6-carboxy-2',4', 7',4,7-hexachlorofiuorescein (HEX), 6-carboxy-4',5'-di-chloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhod-amine 110; cyanine dyes, e.g., Cy3, Cy5 and Cy7 dyes; coumarins, e.g., umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc.; BODIPY dyes and quinoline dyes.

In some embodiments, a detectable label can be a radio-label including, but not limited to $^3H$, $^{125}I$, $^{35}S$, $^{14}C$, $^{32}P$, and $^{33}P$.

In some embodiments, a detectable label can be an enzyme including, but not limited to horseradish peroxidase and alkaline phosphatase. An enzymatic label can produce, for example, a chemiluminescent signal, a color signal, or a fluorescent signal. Enzymes contemplated for use to detect-ably label an antibody reagent include, but are not limited to, malate dehydrogenase, staphylococcal nuclease, delta-V-steroid isomerase, yeast alcohol dehydrogenase, alpha-glyc-erophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamy-lase and acetylcholinesterase.

In some embodiments, a detectable label is a chemilumi-nescent label, including, but not limited to lucigenin, lumi-nol, luciferin, isoluminol, theromatic acridinium ester, imi-dazole, acridinium salt and oxalate ester.

In some embodiments, a detectable label can be a spectral colorimetric label including, but not limited to colloidal gold or colored glass or plastic (e.g., polystyrene, polypropylene, and latex) beads.

In some embodiments, antibodies can also be labeled with a detectable tag, such as c-Myc, HA, VSV-G, HSV, FLAG, V5, HIS, or biotin. Other detection systems can also be used, for example, a biotin-streptavidin system. In this system, the antibodies immunoreactive (i.e., specific for) with the bio-marker of interest is biotinylated. Quantity of biotinylated antibody bound to the biomarker is determined using a streptavidin-peroxidase conjugate and a chromagenic sub-strate. Such streptavidin peroxidase detection kits are com-mercially available, e.g., from DAKO; Carpinteria, Calif.

An antibody reagent can also be detectably labeled using fluorescence emitting metals such as $^{152}Eu$, or others of the lanthanide series. These metals can be attached to the antibody reagent using such metal chelating groups as diethylenetriaminepentaacetic acid (DTPA) or ethylenedi-aminetetraacetic acid (EDTA).

The assays and methods as described herein can relate to determining if a subject has increased levels of CHI3L1 and PD-1 relative to a reference level. In some embodiments, the reference levels of CHI3L1 and PD-1 can be the levels of CHI3L1 and PD-1 in a healthy subject not having, or not diagnosed as having, e.g., cancer. In some embodiments, the reference level can be the level in a sample of similar cell type, sample type, sample processing, and/or obtained from a subject of similar age, sex and other demographic param-eters as the sample/subject for which the level of CHI3L1 and PD-1 are to be determined. In some embodiments, the test sample and control reference sample are of the same type, that is, obtained from the same biological source, and comprising the same composition, e.g., the same number and type of cells and/or type of sample material. Accord-ingly, in some embodiments, the level of CHI3L1 and PD-1 which are increased can vary as demographic factors such as age, gender, genotype, environmental factors, and individual medical histories vary. In some embodiments, the reference levels can comprise the level of CHI3L1 and PD-1 (e.g., CHI3L1 and PD-1 polypeptide) in a sample of the same type taken from a subject not exhibiting any signs or symptoms of, e.g., cancer. In some embodiments, the reference expres-sion levels of CHI3L1 and PD-1 can be the expression level of CHI3L1 and PD-1 in a prior sample obtained from the subject. This permits a direct analysis of any change in levels in that individual.

In some embodiments, levels of CHI3L1 and PD-1 can be increased relative to reference levels if the level of CHI3L1 and PD-1 are at least 1.25× the reference levels, e.g., at least 1.25×, at least 1.5×, at least 2×, at least 3×, at least 4×, at least 5×, at least 6×, or greater of the reference levels. In some embodiments, the expression levels of CHI3L1 and PD-1 can be normalized relative to the expression level of one or more reference genes or reference proteins. In some embodiments, the expression levels of CHI3L1 and PD-1 can be normalized relative to a reference value.

In some embodiments, the expression level of no more than 20 other genes is determined. In some embodiments, the expression level of no more than 10 other genes is determined.

The term "sample" or "test sample" as used herein denotes a sample taken or isolated from an organism, e.g., a urine sample from a subject. Exemplary biological samples include, but are not limited to, a biofluid sample; serum; plasma; urine; saliva; and/or tumor sample, etc. The term also includes a mixture of the above-mentioned samples. The term "test sample" also includes untreated or pretreated (or pre-processed) biological samples. In some embodi-ments, a test sample can comprise cells from a subject. As used herein, the term "biofluid" refers to any fluid obtained from a biological source and includes, but is not limited to, blood, urine, and bodily secretions.

The test sample can be obtained by removing a sample from a subject, but can also be accomplished by using a previously isolated sample (e.g., isolated at a prior timepoint and isolated by the same or another person). In addition, the test sample can be freshly collected or a previously collected sample.

In some embodiments, the test sample can be an untreated test sample. As used herein, the phrase "untreated test sample" refers to a test sample that has not had any prior sample pre-treatment except for dilution and/or suspension in a solution. Exemplary methods for treating a test sample include, but are not limited to, centrifugation, filtration, sonication, homogenization, heating, freezing and thawing, and combinations thereof. In some embodiments, the test sample can be a frozen test sample, e.g., a frozen tissue. The frozen sample can be thawed before employing methods, assays and systems described herein. After thawing, a frozen sample can be centrifuged before being subjected to methods, assays and systems described herein. In some embodiments, the test sample is a clarified test sample, for example, prepared by centrifugation and collection of a supernatant comprising the clarified test sample. In some embodiments, a test sample can be a pre-processed test sample, for example, supernatant or filtrate resulting from a treatment selected from the group consisting of centrifugation, filtration, thawing, purification, and any combinations thereof. In some embodiments, the test sample can be treated with a chemical and/or biological reagent. Chemical and/or biological reagents can be employed to protect and/or maintain the stability of the sample, including biomolecules (e.g., nucleic acid and protein) therein, during processing. One exemplary reagent is a protease inhibitor, which is generally used to protect or maintain the stability of protein during processing. The skilled artisan is well aware of methods and processes appropriate for pre-processing of biological samples required for determination of the level of CHI3L1 as described herein.

In some embodiments, the methods, assays, and systems described herein can further comprise a step of obtaining a test sample from a subject. In some embodiments, the subject can be a human subject.

In some embodiments, the methods, assays, and systems described herein can comprise creating a report based on the levels of CHI3L1 and PD-1. In some embodiments, the report denotes raw values for CHI3L1 and PD-1 in the test sample (plus, optionally, the levels of CHI3L1 and PD-1 in a reference sample) or it indicates a percentage or fold increase in CHI3L1 and PD-1 levels as compared to reference levels, and/or provides a signal that the subject is at risk of having, or not having cancer.

As used herein "at risk of having" refers to at least a 2-fold greater likelihood of having a particular condition as compared to a subject that did not have elevated and/or increased levels of CHI3L1 and PD-1, e.g., a 2-fold, or 2.5-fold, or 3-fold, or 4-fold, or greater risk.

In some embodiments, the assay or method can further comprise the step of administering an anti-CHI3L1/anti-PD-1 therapy. In some embodiments, the anti-CHI3L1/anti-PD-1 therapy comprises an isolated bispecific antibody, antibody reagent, antigen-binding portion thereof, or CAR or CAR T cell; nucleic acid; cell; or composition as described herein.

In one aspect of any of any of the embodiments, described herein is an antibody, antibody reagent, or antigen-binding portion thereof as described herein conjugated to or coupled to a detectable label.

In one aspect of any of any of the embodiments, described herein is a solid support comprising a bispecific antibody, antibody reagent, antigen-binding fragment thereof as described herein. In some embodiments of any of the aspects, the bispecific antibody, antibody reagent or antigen-binding fragment thereof is detectably labeled. In some embodiments of any of the aspects, the solid support comprises a particle, a bead, a polymer, or a substrate.

In one aspect of any of the embodiments, described herein is a molecular complex comprising at least one bispecific antibody, antibody reagent, antigen-binding fragment thereof, or CAR of as described herein bound to an CHI3L1 polypeptide and a PD-1 polypeptide.

In one aspect, described herein is a kit comprising a composition as described herein, e.g., a composition comprising a bispecific antibody, antibody reagent, antigen-binding portion thereof, or CAR as described herein. A kit is any manufacture (e.g., a package or container) comprising at least one reagent, e.g., a bispecific antibody, the manufacture being promoted, distributed, or sold as a unit for performing the methods described herein. In some embodiments of any of the aspects, the bispecific antibody, antibody reagent, antigen-binding fragment thereof as described herein is immobilized on a solid support. In some embodiments of any of the aspects, the solid support comprises a particle, a bead, a polymer, or a substrate. In some embodiments of any of the aspects, the antibody, antibody reagent or antigen-binding fragment thereof is detectably labeled.

The kits described herein can optionally comprise additional components useful for performing the methods described herein. By way of example, the kit can comprise fluids (e.g., buffers) suitable for composition comprising a bispecific antibody, antigen-binding portion thereof, or CAR as described herein, an instructional material which describes performance of a method as described herein, and the like. A kit can further comprise devices and/or reagents for delivery of the composition as described herein. Additionally, the kit may comprise an instruction leaflet and/or may provide information as to the relevance of the obtained results.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting. Although methods and materials similar or equivalent to those described herein can be used in the practice or testing of this disclosure, suitable methods and materials are described below.

EXAMPLES

The invention now being generally described, it will be more readily understood by reference to the following examples which are included merely for purposes of illustration of certain aspects and embodiments of the present invention, and are not intended to limit the invention.

Example 1

Generation and Characterization of CHI3L1xPD1 Bispecific Antibodies (FRGxPD1-SCFv)

Figure 1:
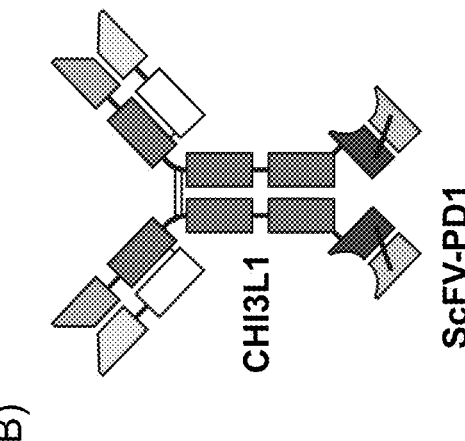
FIG. 1 provides a schematic illustration of CHI3L1xPD1 bispecific antibody structure. The platforms used to generate bispecific antibodies are illustrated in FIG. 1A: CHI3L1-LCxScFv-HC-PD1-ScFv-LC-PD1 (CHI3L1-LC-PD1)
Figure 1:
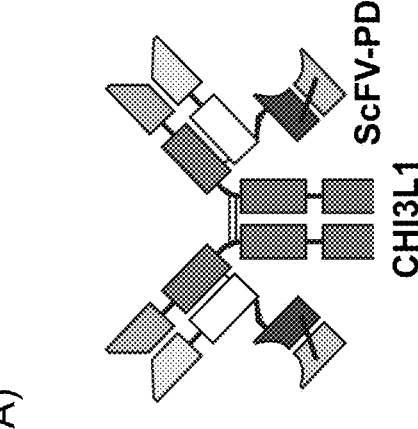

To generate bispecific antibodies that detects and neutralizes CHI3L1 and PD1, we used the backbone of the anti-human CHI3L1 antibody (called "FRG") recently developed in our laboratory and described in U.S. Pat. No. 10,253,111. The PD1 single chain variable fragment (scFv-PD1) was generated based on the sequence information obtained from public domain with minor modification. The ScFv-PD1 was attached to either the Light Chain or Heavy Chain of the CHI3L1 antibody with a linker, as illustrated in FIG. 1. The amino acid sequences of ScFv-PD1 and linkers are provided in Table 2. The constructs of the bivalent CHI3L1xPD1 antibodies were confirmed by DNA sequence analysis.

The CHI3L1xPD1 constructs were transfected individually into the HEK-293T adherent cells. The binding affinities of the bispecific antibodies for CHI3L1 and PD-1 were evaluated by competitive ELISA and compared to the binding of the individual antibody moieties.

Figure 2:
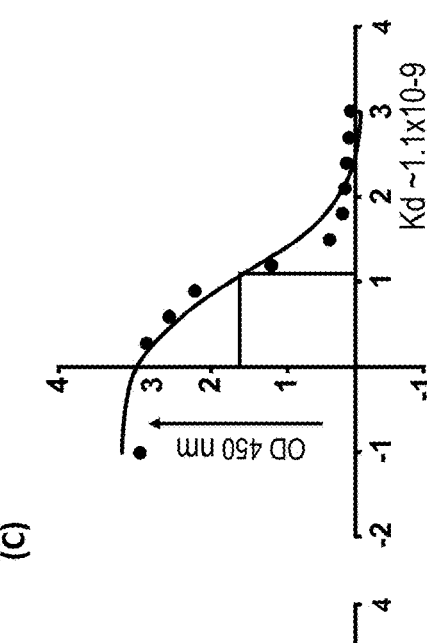
FIG. 2 shows the binding affinities of CHI3L1xPD1 bispecific antibodies. The affinity of CHI3L1-LC-PD1 antibody was evaluated by competitive ELISA assay.
Figure 2:
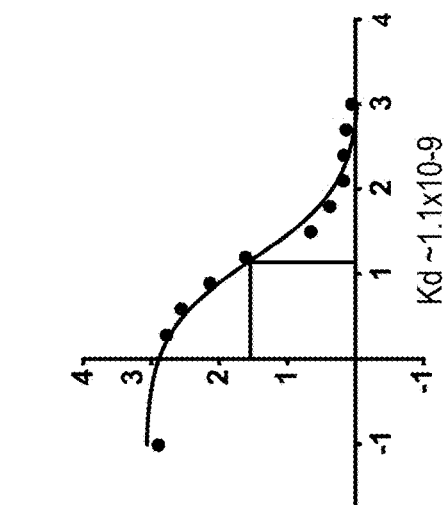
Figure 2:
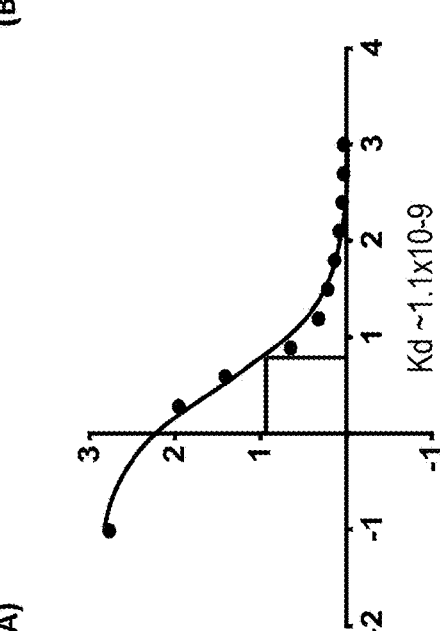

As shown in FIG. 2, the secreted bispecific antibody in the supernatant was able to detect both recombinant human (rh) CHI3L1 and rhPD1. These studies demonstrated that the bispecific antibodies and individual antibody moieties have similar levels of affinity against rhCHI3L1 and rhPD1 (with $K_D \cong 1 \times 10^{-9}$ M) and similar limits of detection (LOD; 2 ng/ml). Protein-A columns was used for further antibody purification.

In summary, we have successfully generated and characterized bispecific antibodies that react to both rhCHI3L1 and rhPD1 with high affinity (see FIG. 1 and FIG. 2). Two different approaches were used to generate these bispecific antibodies as illustrated in FIG. 1. Using these platforms, we generated CHI3L1-LC-PD1 and CHI3L1-HC-PD bispecific (bivalent) antibodies that each detected both human CHI3L1 and human PD1. The affinities of CHI3L1-LC-PD1 antibody (evaluated by competitive ELISA assays) for both rhCHI311 and rhPD1 were estimated to be $K_D \approx 1 \times 10^{-9}$ M with a limit of detection (LOD) is 2 ng/ml. There were no significant differences in the binding affinity to rhCHI3L1 or rhPD1 between CHI3L1-LC-PD1 and CHI3L1-HC-PD1 antibodies (FIG. 2 and data not shown).

Example 2

Characterization of T Cell-U87 Binding and the Antitumoral Cytotoxic Activity of Bispecific CHI3L1xPD1 Antibodies The ability of Jurkat cells to bind to U87 cells and the antitumoral cytotoxic activity of bispecific CHI3L1xPD1 antibodies were assessed using an in vitro co-culture system that included U87 glioblastoma cells (ATCC #HTB-14) and Jurkat T cells (ATCC #TIB152). Human glioblastoma (U87) cells were grown in complete DMEM medium. Jurkat (T cells) were activated by stimulation with $\alpha$-CD3/$\alpha$-CD28 antibodies (5 µg/ml) in RPMI complete medium in 5% CO2 and air for 2 hours. The Jurkat cells were then centrifuged, washed, and resuspended with fresh complete RPMI medium. The U87 and Jurkat cells were cultured at a 1:6 ratio in the complete RPMI medium.

The responses in these co-cultures were evaluated in the presence of an IgG isotype control, anti-PD1 alone, anti-CHI3L1 alone, anti-CHI3I1 and anti-PD-1 in combination (5 µg/ml each) or the bispecific antibody described above. Overall, there were five treatment groups: (i) Isotype IgG control, (ii) $\alpha$-PD1, (iii) $\alpha$-CHI3L1, (iv) $\alpha$-CHI3L1+$\alpha$-PD1, and (v) bispecific $\alpha$-CHI3L1xPD1. The co-cultured cells were incubated for 6-12 hours in 5% CO2 and air. T cell-U87 cell binding was assessed by microscopy, and cell death was assessed using TUNEL staining and LDH release cytotoxicity assays as described below.

A. Quantitation of Jurkat Cell Attachment to U87 Cells

Jurkat T cells were activated with anti-($\alpha$)-human CD3 and $\alpha$-CD28 antibodies (5 µg/ml each incubated for 2 hours in 5% CO2 and air at 37° C.) and co-cultured with U87 glioblastoma cells with the isotype control or the other antibodies noted above. CellBrite cytoplasmic membrane dyes were used for fluorescent labelling of U87 (Red) and Jurkat T cells (Green). The number of Jurkat T cells per U87 cell was counted using fluorescent microscopy (×20 of original magnification) and averaged over 10 randomly chosen microscopic fields.

Figure 3:
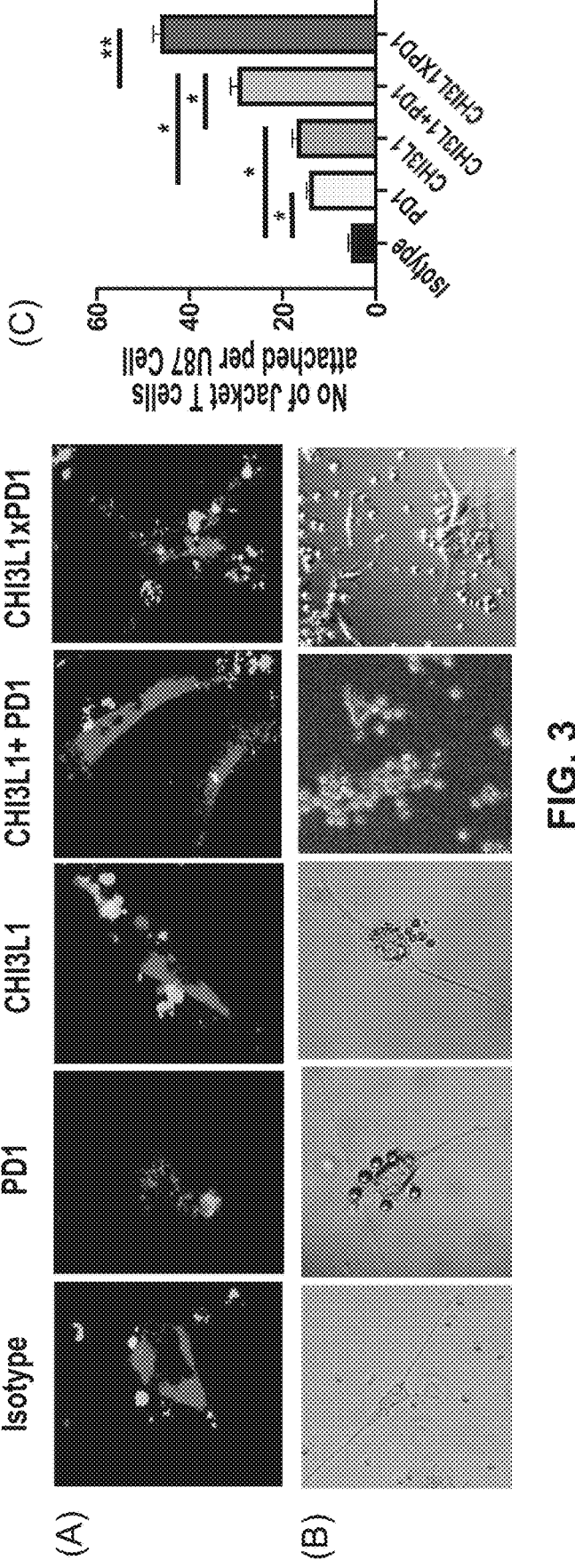
FIG. 3 shows that bispecific CHI3L1xPD1 antibody prominently enhanced the attachment of Jurkat T cells to U87 glioblastoma cells in a co-culture system. Jurkat T cells were activated with anti-human CD3/CD28 treatment (5 μg/ml each, 2 hour incubation in 5% $CO_2$ and air at 37° C.) then co-cultured with U87 glioblastoma cells. Cultures were done with isotype control antibodies and with antibodies that were specific for PD-1, CHI3L1, CHI31L1+ PD-1 and bispecific CHI3L1xPD-1.

As shown in FIG. 3, treatment with bispecific CHI3L1xPD1 antibodies prominently enhanced Jurkat T cell attachment to U87 cells. Importantly, the effects of the bispecific antibodies were significantly more prominent than the effects of treatment with $\alpha$-CHI3L1 or $\alpha$-PD1 individually or treatment with a combination of $\alpha$-CHI3L1 and $\alpha$-PD1.

B. Tunel Assay Quatification of Apoptotic U87 Cell Death

Terminal deoxynucleotidyl transferase mediated dUTP nick end labeling for the in situ assessment of cell death was performed two different ways:

(i) The co-culture treated cells in different chambers were fixed and permealized and stained with fluorescein propidium iodide (red dye) and Cyto (green dye). The cells which fluoresce red are the dead cells and the green are the live cells. The number of live and dead U87 cells were counted using fluorescent microscopy (×20 of original magnification) and averaged over 10 randomly chosen microscopic fields.

(ii) Terminal deoxynucleotidyltransferase-mediated dUTP nick end labeling for the in situ assessment of cell death. In selected studies, TUNEL positive staining was assessed using brightfield microscopy. The dead or apoptotic cells stained blue and the live cells stained with nuclear fast red. The number of live and dead U87 cells were counted using fluorescent and regular microscopy (×20 of original magnification) and averaged over 10 randomly chosen microscopic fields.

Figure 4:
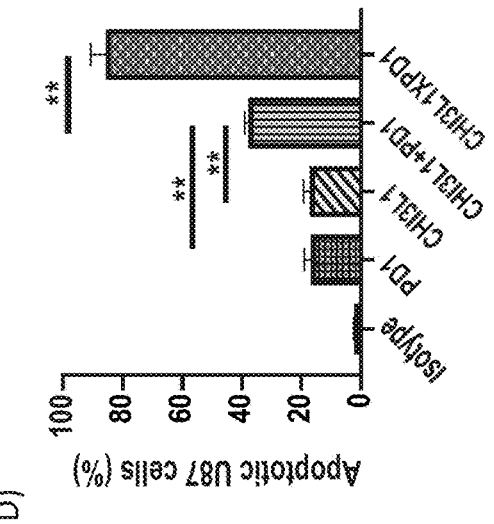
FIG. 4 shows that CHI3L1xPD1 bispecific antibody treatment enhanced U87 glioblastoma cell death response in U87-Jurkat T cell co-cultures. Jurkat T cells were activated with anti-CD3/CD28 treatment (5 μg/ml each for 2 hrs 5% in $CO_2$ (5%) and air at 37° C.) and then co-cultured with U87 glioblastoma cells. Cultures were undertaken with isotype control antibodies and with antibodies that were specific for PD-1, CHI3L1, CHI31L1+PD-1 and bispecific CHI3L1xPD-1.
Figure 4:
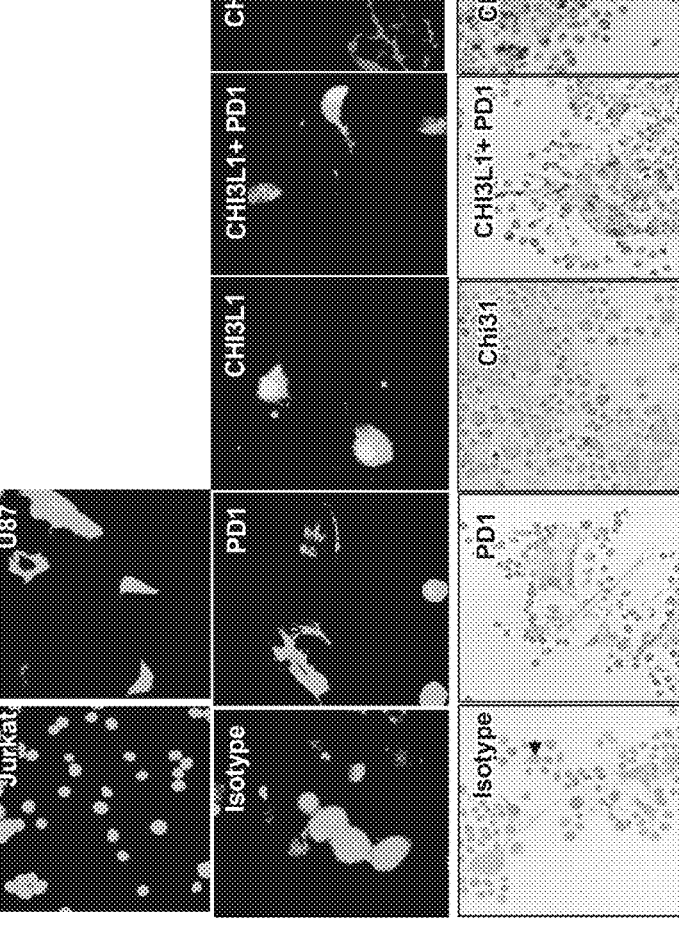

As shown in FIG. 4, treatment with bispecific CHI3L1xPD1 antibody prominently enhanced the ability of Jurkat T cell to induce cytotoxic/apoptotic responses in U87 cells. Importantly, the effects of the bispecific antibodies were significantly more prominent than the effects of treatment with $\alpha$-CHI3L1 or $\alpha$-PD1 individually or treatment with a combination of $\alpha$-CHI3L1 and $\alpha$-PD1.

C. Quantitation of Granzyme and Perforin Accumulation

Granzyme and perforin are the major cytotoxic enzymes secreted by various activated cytotoxic T cells including Jurkat cells. The levels of expression of these cytotoxic enzymes were measured in the cocultured cells using double label immunohistochemistry using antibodies against granzyme (FIG. 5) or perforin (FIG. 6) (red colors) and phalloidin actin filaments (green color). The number of granzyme+ or perforin+cells were counted using fluorescent microscopy (×20 of original magnification) and averaged over 10 randomly chosen microscopic fields.

Figure 5:
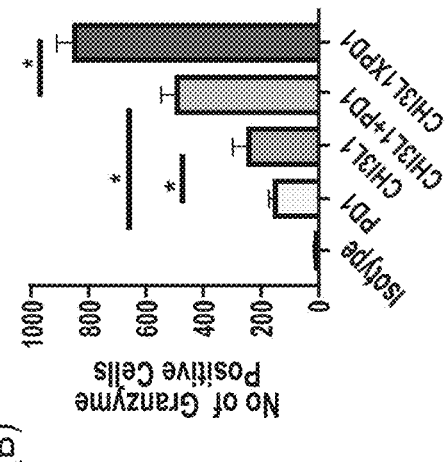
FIG. 5 shows that bispecific CHI3L1xPD1 antibody treatment enhanced the accumulation of granzyme in Jurkat T cells in co-culture with U87 glioblastoma cells. Jurkat T cells were activated with anti-human CD3/CD28 treatment (5 μg/ml each, 2 hour incubation, 5% $CO_2$ and air at 37° C.) then co-cultured with U87 glioblastoma cells. Cultures were done with isotype control antibodies and with antibodies that were specific for PD-1, CHI3L1, CHI31L1+PD-1 and bispecific CHI3L1xPD-1. After 6 hrs of incubation with IgG2b isotype control and indicated antibodies (5 mg/ml, each), fluorescent images were captured (FIG. 5A). Double immunohistochemical staining of the cells was accomplished with a-Granzyme and a-Phalloidin antibodies.
Figure 5:
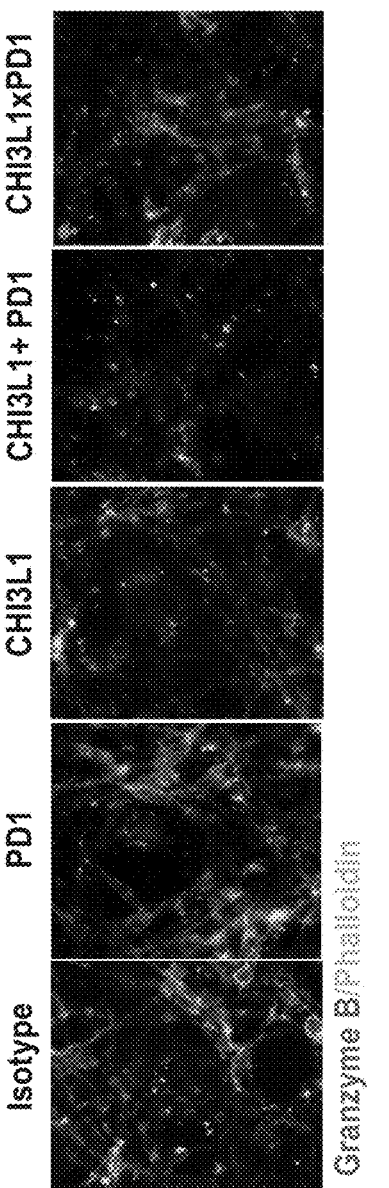
Figure 6:
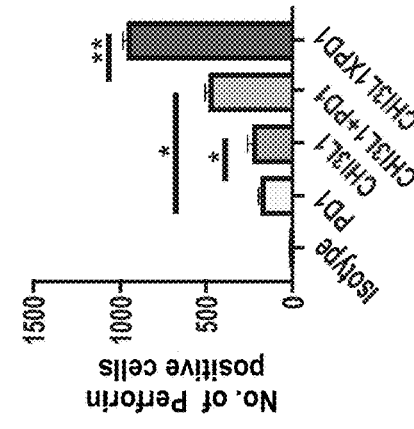
FIG. 6 shows that CHI3L1xPD1 bispecific antibody treatment enhanced the accumulation of perforin in Jurkat T cells in co-culture with U87 glioblastoma cells. Jurkat T cells were activated with anti-human a-CD3/a-CD28 treatment (5 μg/ml each, 2 hour incubation, in 5% $CO_2$ (5%) and air at 37° C.). Cultures were done with isotype control antibodies and with antibodies that were specific for PD-1, CHI3L1, CHI31L1+PD-1 and bispecific CHI3L1xPD-1. After 6 hrs of incubation with IgG2b isotype control and indicated antibodies (5 mg/ml, each), images were captured (FIG. 6A). Double immunohistochemical staining of the cells was accomplished with anti-Perforin and ant-Phalloidin antibodies.
Figure 6:
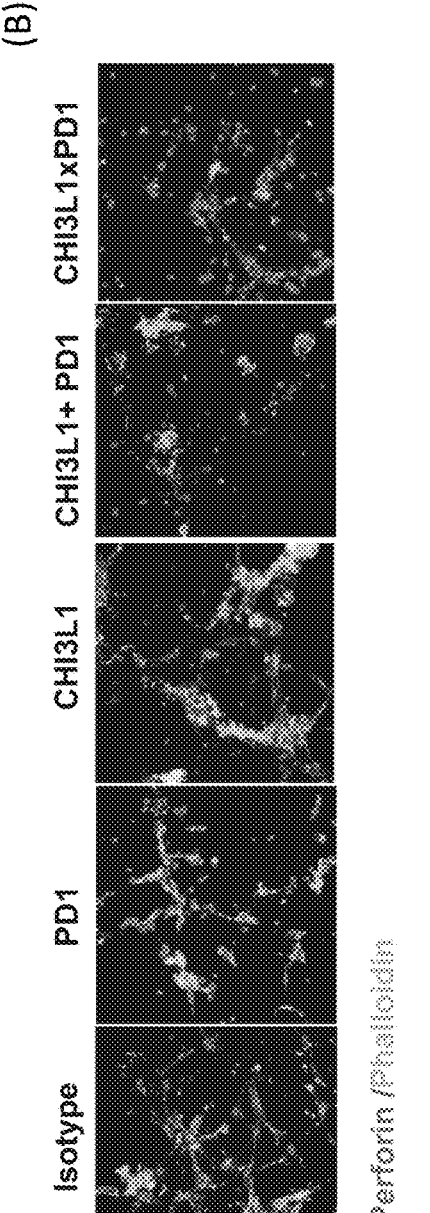

As shown in FIG. 5 and FIG. 6, treatment with bispecific CHI3L1xPD1 antibodies prominently enhanced the accumulation of granzyme and perforin in Jurkat T cells that are in co-culture with U87 cells. Importantly, the effects of the bispecific antibodies were significantly more prominent than the effects of treatment with α-CHI3L1 or α-PD1 individually or treatment with a combination of α-CHI3L1 and α-PD1.

These results suggest that the bispecific CHI3L1xPD1 antibody enhances the cytotoxic effects of T cells in a synergistic manner.

D. LDH Release Cytotoxicity Assay

Lactate dehydrogenase (LDH) is released into the culture medium following loss of membrane integrity from cytotoxic insults. Thus, LDH release was used as an indicator of cell death. This was assessed using a coupled two-step reaction. In the first step of the reaction, LDH catalyzes the reduction of $NAD^+$ to NADH and $H^+$ by oxidation of lactate to pyruvate. In the second step, diaphorase uses the newly-formed NADH and $H^+$ to catalyze the reduction of a tetrazolium salt (INT) to highly-colored formazan which absorbs strongly at 490-520 nm.

The % cytotoxicity levels were determined with a commercial assay kit (Pierce LDH Cytotoxicity Assay Kit) using the protocols provided by the manufacturer. In these experiments, cells were co-cultured in the presence and absence of the antibodies noted above. The LDH in the medium was assessed after overnight incubation. These values were compared to the following controls: (a) complete medium control without cells to determine LDH background activity present in sera used for media supplementation; (b) serum-free media; (c) LDH activity controls (water); and (d) the maximum LDH activity released by cells treated with lysis buffer. In these assays % cytotoxicity was calculated as noted below.

$$\% \text{ Cytotoxicity} = \frac{\text{Compound-treated } LDH \text{ activity} - \text{Spontaneous } LDH \text{ activity}}{\text{Maximum } LDH \text{ activity} - \text{Spontaneous } LDH \text{ activity}} \times 100$$

Figure 7:
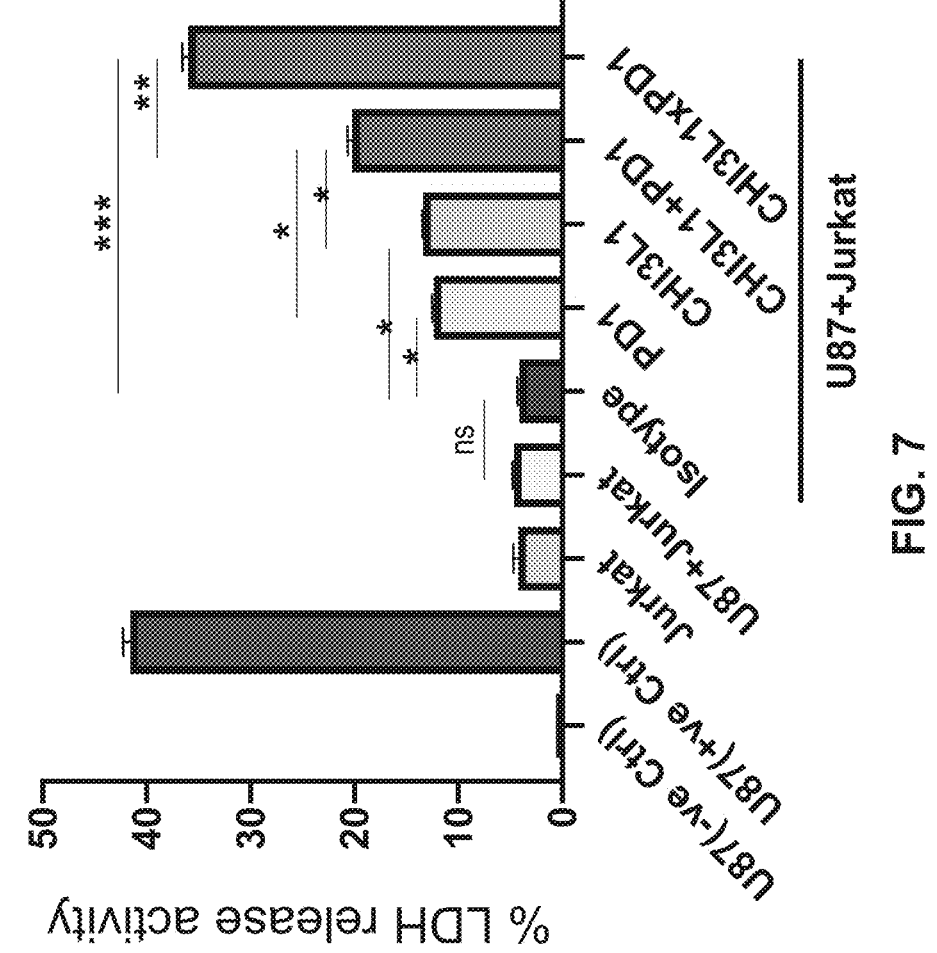
FIG. 7 shows that bispecific CHI3L1xPD1 antibody treatment enhanced U87 cell LDH release in Jurkat-U87 co-cultures. Jurkat T cells were activated with anti-human CD3/CD28 treatment (5 μg/ml each, 2 hour incubation, 5% $CO_2$ and air at 37° C.). Cultures were done with isotype control antibodies and with antibodies that were specific for PD-1, CHI3L1, CHI31L1+PD-1 and bispecific CHI3L1xPD-1. After 6 hrs of incubation with IgG control and indicated antibodies (5 mg/ml, each), LDH activity was measured by assay kit (Pierce LDH Cytotoxicity Assay Kit). ns, not significant, *p<0.05, p<0.01, *p<0.001 by t-test. The LDH released by U87cells in co-culture were compared to the levels in U87 cells alone (-ve control), total LDH in U87 treated with lysis buffer (+ve control) and LDH released by Jurkat cells treated with lysis buffer (Jurkat).

As shown in FIG. 7, treatment with bispecific CHI3L1xPD1 antibody prominently enhanced the ability of Jurkat T cell to induce LDH release and cell cytotoxicity responses in U87 cells. Importantly, the effects of the bispecific antibodies were significantly more prominent than the effects of treatment with α-CHI3L1 or α-PD1 individually or treatment with a combination of α-CHI3L1 and α-PD1.

The synergistic effects of the bispecific CHI3L1xPD1 antibody are further illustrated in FIG. 8. The antitumor effects of the FRGxPD-1 bispecific antibody were evaluated in a co-culture system containing Jurkat cells and A375 human melanoma cells. Jurkat cells were activated by pre-treatment with anti-CD3 and anti-CD28 (1 µg/mL each and incubated for 2 hrs in 5% $CO_2$ and air at 37° C.). The Jurkat cells were then co-cultured with A357 human melanoma cells for 24 hours. These co-cultures were undertaken in the presence of the following antibodies: isotype control antibody (5 µg/mL), anti-PD-1 or anti-CHI3L1 (FRG) alone (5 µg/mL), or in combination (2.5 µg/mL each), and the bispecific FRGxPD-1 antibody (5 µg/mL). Column A provides a representative demonstration and quantitation of apoptotic tumor cell death using in situ cell detection kit-fluorescein dUTP. TUNEL (+) cells stain green. Columns B-D provides a representative demonstration and quantification of Jurkat T cell expression of CD8 (Column B), perforin (Column C) and granzyme (Column D). Tumor cells are green and positive staining Jurkat cells are yellow-orange. Column E provides a representative demonstration and quantification of tumor cell PTEN. Tumor cells are green and PTEN is yellow-orange. Row F provides the quantification of the evaluations in Columns A-E. The % of TUNEL+tumor cells (Column A), % of Jurkat cells expressing CD8 (Column B), perforin (Column C) and granzyme (Column D) and % of tumor cells expressing PTEN (Column E) are illustrated. These evaluations were done using fluorescent microscopy (×20 of original magnification). In these quantifications, 10 randomly selected fields were evaluated. The data in FIG. 8 shows that bispecific CHI3L1xPD1 antibody treatment induced synergistic CTL-mediated tumor cell death responses and tumor cell PTEN expression.

In summary, the newly developed bispecific CHI3L1xPD1 antibodies generated enhanced T cell and U87 cell binding and enhanced the cytotoxic effects on U87 tumor cells compared to α-CHI3L1 and α-PD1 antibodies treatment alone or in combination. These results suggest that the bispecific CHI3L1xPD1 antibodies of the present invention will be more effective therapeutics than α-CHI3L1 or α-PD1 antibodies, alone or in combination, in the treatment of tumors in which CHI3L1 and its receptors and PD1 and its ligands (PD-L1, PD-L2) are dysregulated.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain, using no more than routine experimentation, many equivalents to the specific embodiments described herein. Such equivalents are intended to be encompassed by the following claims.

REFERENCES

ABELOFF'S CLINICAL ONCOLOGY, $2^{nd}$ Edition (2000) Baltzer, L. and Berkery, R. (eds.) Churchill Livingstone, Inc; Perry, et al., Chapter 17, "Chemotherapy."

ABELOFF'S CLINICAL ONCOLOGY, $5^{th}$ Edition, (2013). Niederhuber, J., et al. (eds.) Elsevier; Chapters 28-29, "Therapeutic Targeting of Cancer Cells: Era of Molecularly Targeted Agents and Cancer Pharmacology" (ISBN: 9781455728657).

Ansell, S. M., et al. (2015). "PD-1 blockade with nivolumab in relapsed or refractory Hodgkin's lymphoma." N. Engl. J. Med. 372:311-319.

BASIC METHODS IN MOLECULAR BIOLOGY, (2012). Davis et al. (eds.) Elsevier Science Publishing, Inc., New York, USA (ISBN 044460149X).

BIOCHEMISTRY, $2^{nd}$ edition, (1975). Lehninger, A. L. (ed.), Worth Publishers, New York at pp. 73-75.

Byrd, J. C., et al. (2014). "Entering the era of targeted therapy for chronic lymphocytic leukemia: impact on the practicing clinician." J. Clin. Oncol. 32: 3039-3047.

Chothia, C. et al. (1987). "Canonical structures for the hypervariable regions of immunoglobulins." J. Mol. Biol. 196: 901-917.

Chothia, C. et al. (1989). "Conformations of immunoglobulin hypervariable regions." Nature 342: 877-883 (1989).

CURRENT PROTOCOLS IN IMMUNOLOGY (CPI), (2003). Coligan, J. E., et al. (eds.) John Wiley and Sons, Inc. (ISBN 0471142735, 9780471142737).

CURRENT PROTOCOLS IN MOLECULAR BIOLOGY (CPMB), (2014). Ausubel, F. M. (ed.), John Wiley and Sons (ISBN 047150338X, 9780471503385).

CURRENT PROTOCOLS IN PROTEIN SCIENCE (CPPS), (2005). Coligan, J. E. (ed.), John Wiley and Sons, Inc.

Garon, E. B., et al. (2015). "Pembrolizumab for the treatment of non-small-cell lung cancer." N. Engl. J. Med. 372:2018-2028.

HANDBOOK OF PRACTICAL IMMUNOHISTOCHEMISTRY, (2011). Lin, F., et al. (eds.), Published by Springer.

HARRISON'S PRINCIPLES OF INTERNAL MEDICINE, $18^{th}$ edition, (2011). Longo, D. L. et al. (eds.), published by McGraw-Hill Professional Publishing; Slapak and Kufe, "Principles of Cancer Therapy," Chapter 85.

Hellmann, M. D., et al. (2019). "Nivolumab plus Ipilimumab in Advanced Non-Small-Cell Lung Cancer." N. Engl. J. Med. 381:2020-2031.

Herbst R. S., et al. (2014). "Predictive correlates of response to the anti-PD-L1 antibody MPDL3280A in cancer patients." Nature. 515:563-567.

Hoyos, V., et al. (2012). "Genetic modification of human T lymphocytes for the treatment of hematologic malignancies." Haematologica 97:1622-1631.

Ikeda, Y. and Taira, K. (2006). "Ligand-targeted delivery of therapeutic siRNA." Pharmaceutical Res. 23:1631-1640.

IMMUNOCYTOCHEMISTRY: A PRACTICAL GUIDE FOR BIOMEDICAL RESEARCH, (2009); Burry, R. W. (ed.); published by Springer (ISBN 978-1-4419-1304-3).

IMMUNOHISTOCHEMISTRY: BASICS AND METHODS, (2010). Buchwalow, I. B. and Backer, W. (eds); published by Springer (ISBN-10: 3642046088).

IMMUNOLOGY, (2006). Luttmann, W. et al. (eds.) published by Elsevier (ISBN: 9780120885442).

International Patent Publication WO 2003/063792; Kuchroo, V. K., et al., "Compositions and methods related to TIM-3, a TH1-specific cell surface molecule." Published: Aug. 7, 2003.

International Patent Publication WO 2019/060675; Chupp, G. and Cohn, L., "Anti-YKL40 antibodies and methods of use." Published: Mar. 28, 2019.

JANEWAY'S IMMUNOBIOLOGY, (2014). Murphy, K., et al. (eds.), published by Taylor & Francis Limited, (ISBN 0815345305, 9780815345305).

Kabat, E. A., et al. (1987 and 1991). SEQUENCES OF PROTEINS OF IMMUNOLOGICAL INTEREST. Fifth Edition, U.S. Department of Health and Human Services, NIH Publication No. 91 3242.

Kim, S. H., et al. (2008). "Local and systemic delivery of VEGF siRNA using polyelectrolyte complex micelles for effective treatment of cancer." Journal of Controlled Release 129(2):107-116

LABORATORY METHODS IN ENZYMOLOGY: DNA, $1^{st}$ edition, (2013). Lorsch, J. (ed.) Elsevier (ISBN 0124199542).

Larkin, J., et al. (2015). "Combined nivolumab and ipilimumab or monotherapy in untreated melanoma." N. Engl. J. Med. 373:23-34.

LEWIN'S GENES XI, $11^{th}$ edition, (2014). Krebs, J. E., et al. (eds.), published by Jones & Bartlett Publishers (ISBN-1449659055).

Lorenze, C., et al. (2004). "Steroid and lipid conjugates of siRNAs to enhance cellular uptake and gene silencing in liver cells." Bioorg. Med. Chem. Lett. 14: 4975-4977

MacCallum, R. M., et al. (1996). "Antibody-antigen interactions: contact analysis and binding site topography." J. Mol. Biol. 262(5):732-745.

Maher, J. and Wilkie, S. (2009). "CAR Mechanics: Driving T Cells into the MUC of Cancer." Cancer Res 69: 4559-4562.

Maus, M. V., et al. (2014). "Antibody-modified T cells: CARs take the front seat for hematologic malignancies." Blood 123: 2624-2635.

McNamara, J. O., et al. (2006). "Cell type-specific delivery of siRNAs with aptamer-siRNA chimeras." Nat. Biotechnol. 24:1005-1015

MOLECULAR BIOLOGY AND BIOTECHNOLOGY: A COMPREHENSIVE DESK REFERENCE, (1995). Robert A. Meyers (ed.), published by VCH Publishers, Inc. (ISBN 1-56081-569-8).

MOLECULAR CLONING: A LABORATORY MANUAL, $4^{th}$ edition, (2012). Green M. R. and Sambrook, J., Cold Spring Harbor Laboratory Press, Cold Spring Harbor, N.Y., USA (ISBN 1936113414).

Nghiem, P. T., et al. (2016). "PD-1 blockade with Pembrolizumab in advanced Merkel-cell carcinoma." N. Engl. J. Med. 374:2542-2552.

Padlan, E. A., et al. (1995). "Identification of specificity-determining residues in antibodies." FASEB J. 9:133-139.

Paz-Ares, L., et al. (2018). "Pembrolizumab plus Chemotherapy for Squamous Non-Small-Cell Lung Cancer." N. Engl. J. Med. 379:2040-2051.

PHYSICIANS' CANCER CHEMOTHERAPY DRUG MANUAL, (2018). Chu, E. and DeVita Jr., V. T. (eds.), published by Jones & Bartlett Learning (ISBN: 9781284187328).

Postow, M. A., et al. (2015). "Nivolumab and ipilimumab versus ipilimumab in untreated melanoma." N. Engl. J. Med. 372:2006-2017.

Powles, T., et al. (2014). "MPDL3280A (anti-PD-L1) treatment leads to clinical activity in metastatic bladder cancer." Nature. 515:558-562.

Reardon, D. A., et al. (2014). "Immunotherapy advances for glioblastoma." Neuro-Oncology 16: 1441-1458.

Ribas, A., et al. (2016). "Association of Pembrolizumab with tumor response and survival among patients with advanced melanoma." JAMA. 315:1600-1609.

Robert, C., et al. (2015a). "Nivolumab in previously untreated melanoma without BRAF mutation." N. Engl. J. Med. 372:320-330.

Robert, C., et al. (2015b). "Pembrolizumab versus ipilimumab in advanced melanoma. N. Engl. J. Med. 372: 2521-2532.

Rockwood, D. N., et al. (2011). "*Materials fabrication from Bombyx mori silk fibroin.*" Nature Protocols 6: 1612-1631.

Schoenfeld, A. J., et al. (2020). "*Clinical and molecular correlates of PD-L1 expression in patients with lung adenocarcinomas.*" Annals of Oncology 31(5): 599-608.

Soutschek, J., et al. (2004). "*Therapeutic silencing of an endogenous gene by systemic administration of modified siRNAs.*" Nature 432: 173-178.

Tamada, K., et al. (2012). "*Redirecting Gene-Modified T Cells toward Various Cancer Types Using Tagged Antibodies.*" Clin Cancer Res 18: 6436-6445.

THE CANCER CHEMOTHERAPY HANDBOOK, 4$^{th}$ edition (2003). Fischer, D. S. et al. (eds.) Mosby-Year Book, St. Louis (ISBN-10: 0801668824).

THE ENCYCLOPEDIA OF MOLECULAR CELL BIOLOGY AND MOLECULAR MEDICINE, (1999-2012) Porter, R. S., et al. (eds.), published by Blackwell Science Ltd., (ISBN 9783527600908).

THE MERCK MANUAL OF DIAGNOSIS AND THERAPY, 19$^{th}$ Edition, (2011). published by Merck Sharp & Dohme Corp., (ISBN 978-0-911910-19-3).

Topalian S. L., et al., (2012). "*Safety, activity, and immune correlates of anti-PD-1 antibody in cancer.*" N. Engl. J. Med. 366:2443-2454.

U.S. Pat. No. 5,585,089; Queen, C. L. et al., "*Humanized immunoglobulins.*" Issued: Dec. 17, 1996.

U.S. Pat. No. 6,824,989. Eisinger, D. et al., "*Recombinant monoclonal antibody to phosphotyrosine-containing proteins.*" Issued: Nov. 30, 2004.

U.S. Pat. No. 6,835,823; Le, J. et al. "*Anti-TNF antibodies and peptides of human tumor necrosis factor.*" Issued: Dec. 28, 2004.

U.S. Pat. No. 7,427,605; Davis, M. E. et al., "*Inhibitors of ribonucleotide reductase subunit 2 and uses thereof.*" Issued: Sep. 23, 2008.

U.S. Pat. No. 8,172,901; Altman, G. H. et al., "*Prosthetic device and method of manufacturing the same.*" Issued: May 8, 2012.

U.S. Pat. No. 8,329,660; Kuchroo; V. K., et al., "*Tim-3 ligands and methods thereof.*" Issued: Dec. 11, 2012.

U.S. Pat. No. 10,155,037; Abdiche Y. N., et al.; "*Anti-PD-1 antibodies and methods of use thereof.*" Issued: Dec. 18, 2018.

U.S. Pat. No. 10,221,244; Wong, B., et al.; "*Anti-CSF1R antibody and anti PD-1 antibody combination therapy for cancer.*" Issued: Mar. 5, 2019.

U.S. Pat. No. 10,239,942; Amirina, N., et al.; "*Anti-PD-1 antibodies.*" Issued: Mar. 26, 2019.

U.S. Pat. No. 10,280,224; Wang C.-i., et al.; "*Anti-PD-1 antibodies.*" Issued: May 7, 2019.

U.S. Pat. No. 10,316,089, Baruah, H., et al.; "*PD-1 antibodies.*" Issued: Jun. 11, 2019.

U.S. Pat. No. 10,323,091; van Dijk, M., et al.; "*Anti-PD-1 antibodies and methods of use thereof.*" Issued: Jun. 18, 2019.

U.S. Pat. No. 10,344,090; Yuan, J., et al.; "*PD-1 antibody, antigen-binding fragment thereof, and medical application thereof.*" Issued: Jul. 9, 2019.

U.S. Pat. No. 10,253,111; Elias, J. A. et al., "*Methods and compositions relating to anti-CHI3L1 antibody reagents.*" Issued: Apr. 9, 2019.

U.S. Published Application No. 2011/0009960; Altman, G. H. et al., "*Prosthetic fabric structure.*" Published: Jan. 13, 2011.

U.S. Published Application No. 2011/0123550; Shibayama, S. et al., "*Use of an efficacy marker for optimizing therapeutic efficacy of an anti-human PD-1 antibody on cancers.*" Published: May 26, 2011.

U.S. Published Application No. 2011/0167602; Altman, G. H. et al., "*Immunoneutral silk fiber-based medical devices.*" Published: Jul. 14, 2011.

U.S. Published Application No. 2012/0296352; Altman, G. H. et al., "*Sericin extracted fabrics.*" Published: Nov. 22, 2012.

U.S. Published Application No. 2016/0376367; Yuan, J. et al., "*PD-1 antibody, an antigen-binding fragment thereof, and medical application thereof.*" Published: Dec. 29, 2016.

U.S. Published Application No. 2017/0210806; Liu J., "*Anti-PD-1 antibody and use thereof.*" Published: Jul. 27, 2017.

U.S. Published Application No. 2019/0062457; Elias, J. A., "*Methods and compositions relating to Anti-CHI3L1 antibody reagents.*" Published: Jul. 28, 2019.

Weber, J. S., et al. (2015). "*Nivolumab versus chemotherapy in patients with advanced melanoma who progressed after anti-CTLA-4 treatment (CheckMate 037): a randomised, controlled, open-label, phase 3 trial.*" Lancet Oncol. 16:375-384.

Wolchok, J. D., et al. (2013). "*Nivolumab plus ipilimumab in advanced melanoma.*" N. Engl. J. Med. 369:122-133.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

---

We claim:

1. A bispecific antibody that detects and neutralizes chitinase 3-like-1 (CHI3L1) and programmed death receptor 1 (PD-1), wherein the bispecific antibody comprises an antigen-binding portion of an anti-human PD-1 antibody and an antigen-binding portion of an anti-human CHI3L1 antibody, wherein the antigen-binding portion of the anti-human PD-1 antibody comprises the amino acid sequence of SEQ ID NO: 35, wherein the antigen-binding portion of the anti-human CHI3L1 antibody comprises the complementarity determining regions (CDRs) of:

(a) a light chain CDR1 having the amino acid sequence of SEQ ID NO: 4;

(b) a light chain CDR2 having the amino acid sequence of SEQ ID NO: 5;

(c) a light chain CDR3 having the amino acid sequence of SEQ ID NO: 6;

(d) a heavy chain CDR1 having the amino acid sequence of SEQ ID NO: 1;

(e) a heavy chain CDR2 having the amino acid sequence of SEQ ID NO: 2;

(f) a heavy chain CDR3 having the amino acid sequence of SEQ ID NO: 3, and wherein 1) An anti-human PD-1 single chain variable fragment (ScFv-PD1) is attached to a backbone of the anti-human CHI3L1 antibody, or 2) an anti-human CHI3L1 single chain variable fragment (ScFv-CHI3L1) is attached to a backbone of the anti-human PD-1 antibody.

2. The bispecific antibody of claim 1, wherein the ScFv-PD1 is attached to the CHI3L1 antibody heavy chain (CHI3L1-HC-PD1).

3. The bispecific antibody of claim 1, wherein the ScFv-PD1 is attached to the CHI3L1 antibody light chain (CHI3L1-LC-PD1).

4. The bispecific antibody of claim 2, wherein the CHI3L1 antibody heavy chain has the amino acid sequence of SEQ ID NO: 13.

5. The bispecific antibody of claim 3, wherein the CHI3L1 antibody light chain has the amino acid sequence of SEQ ID NO: 14.

6. The bispecific antibody of claim 1, wherein the bispecific antibody enhances Jurkat T cell attachment to U87 cells.

7. The bispecific antibody of claim 6, wherein the bispecific antibody enhances the ability of Jurkat T cells to induce cytotoxic/apoptotic responses in U87 cells.

8. The bispecific antibody of claim 6, wherein the bispecific antibody enhances the accumulation of granzyme and perforin in Jurkat T cells that are in co-culture with U87 cells.

9. The bispecific antibody of claim 6, wherein the bispecific antibody enhances the ability of Jurkat T cells to induce lactate dehydrogenase (LDH) release and cell cytotoxicity responses in U87 cells.

10. A pharmaceutical composition comprising the bispecific antibody of claim 1 and a pharmaceutically acceptable carrier.

11. The pharmaceutical composition of claim 10, further comprising a chemotherapeutic agent.

12. A method of treating cancer in a subject in need thereof, the method comprising administering to the subject a therapeutically-effective amount of the bispecific antibody of claim 1 or a pharmaceutical composition of claim 10.

13. The method of claim 12, wherein the cancer is a malignant cancer.

14. The method of claim 12, wherein the cancer is a primary cancer or a metastatic cancer.

15. The method of claim 12, wherein the cancer is selected from the group consisting of: pancreatic cancer, prostate cancer, colon cancer, rectal cancer, ovarian cancer, kidney cancer, breast cancer, glioblastoma, melanoma, malignant melanoma, and lung cancer.

16. The method of claim 12, wherein the subject is determined to have an elevated level of CHI3L1.

17. The method of claim 16, wherein the level of CHI3L1 is circulating CHI3L1.

18. The method of claim 12, wherein the cancer expresses PD-L1.

* * * * *

SEQUENCE LISTING

```
<160> NUMBER OF SEQ ID NOS: 37

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
```

-continued

```
        peptide

<400> SEQUENCE: 1

Gly Tyr Thr Phe Thr Asn Tyr Gly
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 2

Ile Asn Thr Tyr Thr Gly Glu Pro
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 3

Ala Arg Leu Gly Tyr Gly Lys Phe Tyr Val Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 4

Gln Ser Leu Val His Ser Asn Gly Asn Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 5

Lys Val Ser
1

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
        peptide

<400> SEQUENCE: 6

Ser Gln Ser Thr His Val Thr Trp Thr
1               5

<210> SEQ ID NO 7
```

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gggtatacct tcacaaacta tgga                                          24

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
ataaatacct acactggaga gcca                                          24

<210> SEQ ID NO 9
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gcaagattgg gatatggtaa attctatgtt atggactac                          39

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagagccttg tacacagtaa tggaaacacc tat                                33

<210> SEQ ID NO 11
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 aaagtttcc                                                            9

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
tctcaaagta cacatgttac gtggacg                                       27

<210> SEQ ID NO 13
<211> LENGTH: 120
```

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Arg Asn Glu Asp Met Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120
```

<210> SEQ ID NO 14
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Thr Trp Thr Phe Gly Gly Gly Thr Lys Leu Glu Ile Lys
            100                 105                 110
```

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

```
Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
```

-continued

```
                20              25              30

Gly Met Asn Trp Val Arg Gln Ala Pro Gly Gln Gly Leu Glu Trp Met
        35              40              45

Gly Trp Ile Asn Thr Tyr Thr Gly Glu Pro Thr Tyr Ala Asp Asp Phe
    50              55              60

Lys Gly Arg Phe Val Phe Ser Leu Asp Thr Ser Val Ser Thr Ala Tyr
65              70              75              80

Leu Gln Ile Ser Ser Leu Lys Ala Glu Asp Thr Ser Val Tyr Phe Cys
                85              90              95

Ala Arg Leu Gly Tyr Gly Lys Phe Tyr Val Met Asp Tyr Trp Gly Gln
            100             105             110

Gly Thr Ser Val Thr Val Ser Ser
        115             120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gln Ile Gln Leu Val Gln Ser Gly Ser Glu Leu Lys Lys Pro Gly Ala
1               5               10              15

Ser Val Lys Ile Ser Cys Lys Ala Ser Gly Tyr Thr Phe Thr Asn Tyr
            20              25              30

Gly Met Asn Trp Val Arg Gln Ala Pro Gly Gln Gly Leu Glu Trp Met
        35              40              45

Gly Trp Ile Asn Thr Tyr Thr Gly Glu Pro Thr Tyr Ala Gln Gly Phe
    50              55              60

Thr Gly Arg Phe Val Phe Ser Leu Asp Thr Ser Val Ser Thr Ala Tyr
65              70              75              80

Leu Gln Ile Ser Ser Leu Lys Ala Glu Asp Thr Ser Val Tyr Phe Cys
                85              90              95

Ala Arg Leu Gly Tyr Gly Lys Phe Tyr Val Met Asp Tyr Trp Gly Gln
            100             105             110

Gly Thr Ser Val Thr Val Ser Ser
        115             120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Ile Gln Leu Val Gln Ser Gly Pro Glu Leu Lys Lys Pro Gly Ala
1               5               10              15

Ser Val Lys Ile Ser Cys Lys Ala Ser Gly Tyr Thr Phe Thr Asn Tyr
            20              25              30

Gly Met Asn Trp Val Arg Gln Ala Pro Gly Gln Gly Leu Lys Trp Met
        35              40              45

Gly Trp Ile Asn Thr Tyr Thr Gly Glu Pro Thr Tyr Ala Asp Asp Phe
    50              55              60

Thr Gly Arg Phe Val Phe Ser Leu Asp Thr Ser Val Ser Thr Ala Tyr
```

```
65                  70                  75                  80

Leu Gln Ile Ser Ser Leu Lys Ala Glu Asp Thr Ser Val Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ile Gln Leu Val Gln Ser Gly Ser Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ser Val Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Ile Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
```

-continued

```
          115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ile Gln Leu Val Gln Ser Gly Pro Glu Leu Lys Lys Pro Gly Ala
1               5                   10                  15

Ser Val Lys Ile Ser Cys Lys Ala Ser Gly Tyr Thr Phe Thr Ser Tyr
            20                  25                  30

Ala Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ser Val Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Ile Gln Leu Val Gln Ser Gly His Glu Val Lys Gln Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Pro Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Ala Ser Thr Ala Tyr
65                  70                  75                  80

Leu Gln Ile Ser Ser Leu Lys Ala Glu Asp Met Ser Met Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 22

```
Gln Ile Gln Leu Val Gln Ser Gly His Glu Val Lys Gln Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Pro Gln Ala Pro Gly Gln Gly Leu Glu Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Ala Ser Thr Ala Tyr
65                  70                  75                  80

Leu Gln Ile Ser Ser Leu Lys Ala Glu Asp Met Ser Met Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120
```

<210> SEQ ID NO 23
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gln Ile Gln Leu Val Gln Ser Gly His Glu Val Lys Gln Pro Gly Ala
1               5                   10                  15

Ser Val Lys Ile Ser Cys Lys Ala Ser Gly Tyr Thr Phe Thr Asn Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Ala Ser Thr Ala Tyr
65                  70                  75                  80

Leu Gln Ile Ser Ser Leu Lys Ala Glu Asp Met Ser Met Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120
```

<210> SEQ ID NO 24
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Gln Ile Gln Leu Val Gln Ser Gly Pro Glu Val Lys Gln Pro Gly Ala
1               5                   10                  15

Ser Val Lys Ile Ser Cys Lys Ala Ser Gly Tyr Thr Phe Thr Asn Tyr
            20                  25                  30
```

```
Gly Met Asn Trp Val Pro Gln Ala Pro Gly Gln Gly Leu Lys Trp Met
        35                  40                  45

Gly Trp Ile Asn Thr Tyr Thr Gly Glu Pro Thr Tyr Ala Asp Asp Phe
    50                  55                  60

Thr Gly Arg Phe Val Phe Ser Leu Asp Thr Ser Ala Ser Thr Ala Tyr
65                  70                  75                  80

Leu Gln Ile Ser Ser Leu Lys Ala Glu Asp Met Ser Met Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 25
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Ile Gln Leu Val Gln Ser Gly Pro Glu Val Lys Gln Pro Gly Ala
1               5                   10                  15

Ser Val Lys Ile Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
        35                  40                  45

Gly Trp Ile Asn Thr Tyr Thr Gly Glu Pro Thr Tyr Ala Gln Gly Phe
    50                  55                  60

Thr Gly Arg Phe Val Phe Ser Leu Asp Thr Ser Ala Ser Thr Ala Tyr
65                  70                  75                  80

Leu Gln Ile Ser Ser Leu Lys Ala Glu Asp Met Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 26
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ile Gln Leu Val Gln Ser Gly Pro Glu Val Lys Gln Pro Gly Ala
1               5                   10                  15

Ser Val Lys Ile Ser Cys Lys Ala Ser Gly Tyr Ser Phe Thr Thr Tyr
                20                  25                  30

Gly Met Asn Trp Val Lys Gln Ala Pro Gly Gln Gly Leu Glu Trp Met
        35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Ala Ser Thr Ala Tyr
65                  70                  75                  80
```

-continued

```
Leu Gln Ile Ser Ser Leu Lys Ala Glu Asp Met Ser Thr Tyr Phe Cys
                85                  90                  95

Ala Arg Leu Gly Tyr Gly Lys Phe Tyr Val Met Asp Tyr Trp Gly Gln
            100                 105                 110

Gly Thr Ser Val Thr Val Ser Ser
        115                 120

<210> SEQ ID NO 27
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu Asn Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Thr Trp Thr Phe Gly Gly Gly Thr Lys Leu Glu Ile Lys
            100                 105                 110

<210> SEQ ID NO 28
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Thr Trp Thr Phe Gly Gly Gly Thr Lys Leu Glu Ile Lys
            100                 105                 110

<210> SEQ ID NO 29
<211> LENGTH: 112
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 29

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Thr Trp Thr Phe Gly Gly Gly Thr Lys Leu Glu Ile Lys
            100                 105                 110

<210> SEQ ID NO 30
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Thr Trp Thr Phe Gly Gly Gly Thr Lys Leu Glu Ile Lys
            100                 105                 110

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45
```

```
Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Thr Trp Thr Phe Gly Gly Gly Thr Lys Leu Glu Ile Lys
            100                 105                 110
```

<210> SEQ ID NO 32
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Thr Trp Thr Phe Gly Gly Gly Thr Lys Leu Glu Ile Lys
            100                 105                 110
```

<210> SEQ ID NO 33
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Leu Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Thr Trp Thr Phe Gly Gly Gly Thr Lys Leu Glu Ile Lys
            100                 105                 110
```

<210> SEQ ID NO 34
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Thr Trp Thr Phe Gly Gly Gly Thr Lys Leu Glu Ile Lys
            100                 105                 110

<210> SEQ ID NO 35
<211> LENGTH: 269
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Val Glu Gly Gly Ser Gly Gly Ser Gly Gly Ser Gly Gly Ser Gly Gly
1               5                   10                  15

Val Asp Gln Val Gln Leu Val Gln Ser Gly Ala Glu Val Lys Lys Pro
            20                  25                  30

Gly Ala Ser Val Lys Val Ser Cys Lys Ala Ser Gly Tyr Thr Phe Thr
        35                  40                  45

Asn Tyr Tyr Met Tyr Trp Val Arg Gln Ala Pro Gly Gln Gly Leu Glu
    50                  55                  60

Trp Met Gly Gly Ile Asn Pro Ser Asn Gly Gly Thr Asn Phe Asn Glu
65                  70                  75                  80

Lys Phe Lys Asn Arg Val Thr Leu Thr Thr Asp Ser Ser Thr Thr Thr
                85                  90                  95

Ala Tyr Met Glu Leu Lys Ser Leu Gln Phe Asp Asp Thr Ala Val Tyr
            100                 105                 110

Tyr Cys Ala Arg Arg Asp Tyr Arg Phe Asp Met Gly Phe Asp Tyr Trp
            115                 120                 125

Gly Gln Gly Thr Leu Val Thr Val Ser Ser Gly Gly Gly Gly Ser Gly
    130                 135                 140

Gly Gly Gly Ser Gly Gly Gly Gly Ser Gly Gly Gly Gly Ser Glu Ile
145                 150                 155                 160

Val Leu Thr Gln Ser Pro Gly Thr Leu Ser Leu Ser Pro Gly Glu Arg
                165                 170                 175

Ala Thr Leu Ser Cys Arg Ala Ser Lys Gly Val Ser Thr Ser Gly Tyr
            180                 185                 190

Ser Tyr Leu His Trp Tyr Gln Gln Lys Pro Gly Gln Ala Pro Arg Leu
        195                 200                 205
```

-continued

```
Leu Ile Tyr Leu Ala Ser Tyr Leu Glu Ser Gly Val Pro Asp Arg Phe
    210                 215                 220

Ser Gly Ser Gly Ser Gly Thr Asp Phe Thr Leu Thr Ile Ser Arg Leu
225                 230                 235                 240

Glu Pro Glu Asp Phe Ala Val Tyr Tyr Cys Gln His Ser Arg Asp Leu
                245                 250                 255

Pro Leu Thr Phe Gly Gly Gly Thr Lys Val Glu Ile Lys
                260                 265

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Gly Gly Gly Ser
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 37

His His His His His His
1               5
```